US008107589B2

(12) United States Patent
Sakurai et al.

(10) Patent No.: US 8,107,589 B2
(45) Date of Patent: Jan. 31, 2012

(54) RADIOTHERAPEUTIC SYSTEM AND RADIOTHERAPEUTIC DOSE DISTRIBUTION MEASURING METHOD

(75) Inventors: Yasuo Sakurai, Otawara (JP); Shigeharu Ohyu, Yaita (JP); Kyojiro Nambu, Nasushiobara (JP); Motoji Haragashira, Utsunomiya (JP); Masahiro Kumakura, Otawara (JP); Mariko Shibata, Nasushiobara (JP); Katsuhiko Fujimoto, Saitama (JP); Yoichi Takada, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 329 days.

(21) Appl. No.: 12/336,919

(22) Filed: Dec. 17, 2008

(65) Prior Publication Data

US 2009/0161818 A1    Jun. 25, 2009

(30) Foreign Application Priority Data

Dec. 21, 2007  (JP) ................. 2007-331108
Feb. 6, 2008   (JP) ................. 2008-026733
Feb. 14, 2008  (JP) ................. 2008-033361
Feb. 14, 2008  (JP) ................. 2008-033362

(51) Int. Cl.
*A61N 5/10*          (2006.01)
(52) U.S. Cl. ................. 378/65; 378/7; 378/147
(58) Field of Classification Search .......... 378/65, 378/7, 147; 250/363.1
See application file for complete search history.

(56) References Cited

U.S. PATENT DOCUMENTS

| 2005/0058240 A1* | 3/2005 | Claus ........................ 378/22 |
| 2005/0072930 A1* | 4/2005 | Hoffman et al. ............ 250/368 |
| 2005/0243963 A1* | 11/2005 | Ghelmansarai et al. ...... 378/7 |
| 2007/0071169 A1 | 3/2007 | Yeo et al. |

FOREIGN PATENT DOCUMENTS

| JP | 5-146426 | 6/1993 |
| WO | 2007/031898 A1 | 3/2007 |

OTHER PUBLICATIONS

U.S. Appl. No. 12/349,680, filed Jan. 7, 2009, Sakurai, et al.
W. J. C. Van Elmpt, et al., "Experimental Verification of a Portal Dose Prediction Model", Medical Physics, vol. 32, No. 9, XP012075453, Aug. 22, 2005, pp. 2805-2818.
Geneviéve Jarry, et al., "Patient-Specific Dosimetry of Conventional and Intensity Modulated Radiation Therapy Using a Novel Full Monte Carlo Phase Space Reconstruction Method from Electronic Portal Images", Physics in Medicine and Biology, vol. 52, No. 8, XP020113292, Apr. 21, 2007, pp. 2277-2299.

* cited by examiner

*Primary Examiner* — Hoon Song
*Assistant Examiner* — Mona M Sanei
(74) *Attorney, Agent, or Firm* — Oblon, Spivak, McClelland, Maier & Neustadt, L.L.P.

(57) ABSTRACT

A detector having a collimator in a position at a specific angle with respect to a therapeutic X-ray beam is mounted to selectively detect only scattering radiation in the direction. To three-dimensionally obtain a distribution of places where scattering occurs in a patient body, a detector is rotated during irradiation and scattering radiation is measured from all of directions. After that, a reconstructing process is performed, and a distribution of occurrence of scattering radiation in the subject is three-dimensionally imaged. Since angles and amounts of X-rays scattered by Compton scattering are known theoretically, if scattering radiation at a certain angle can be detected, the number of scattering radiation at other angles can be also estimated. On the basis of the theory, images of distribution of scattering radiation sources are converted to images of distribution of absorption of radiation.

18 Claims, 40 Drawing Sheets

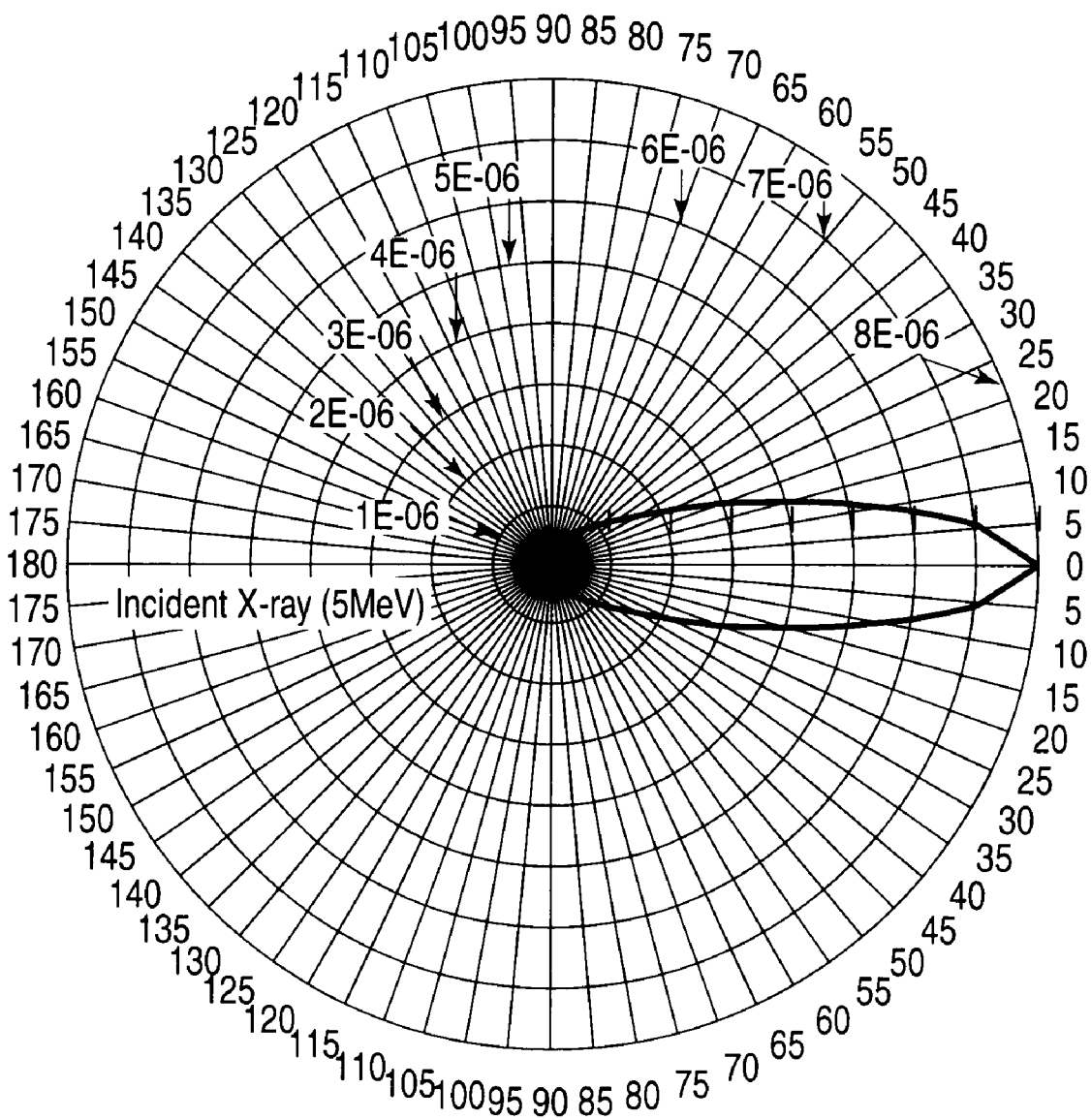
F I G. 9

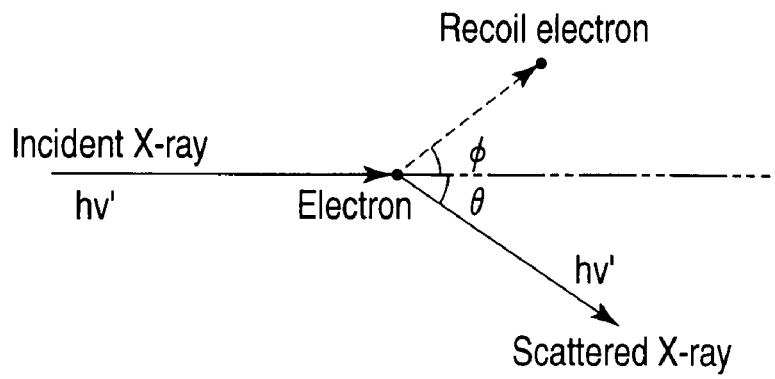
F I G. 1 1
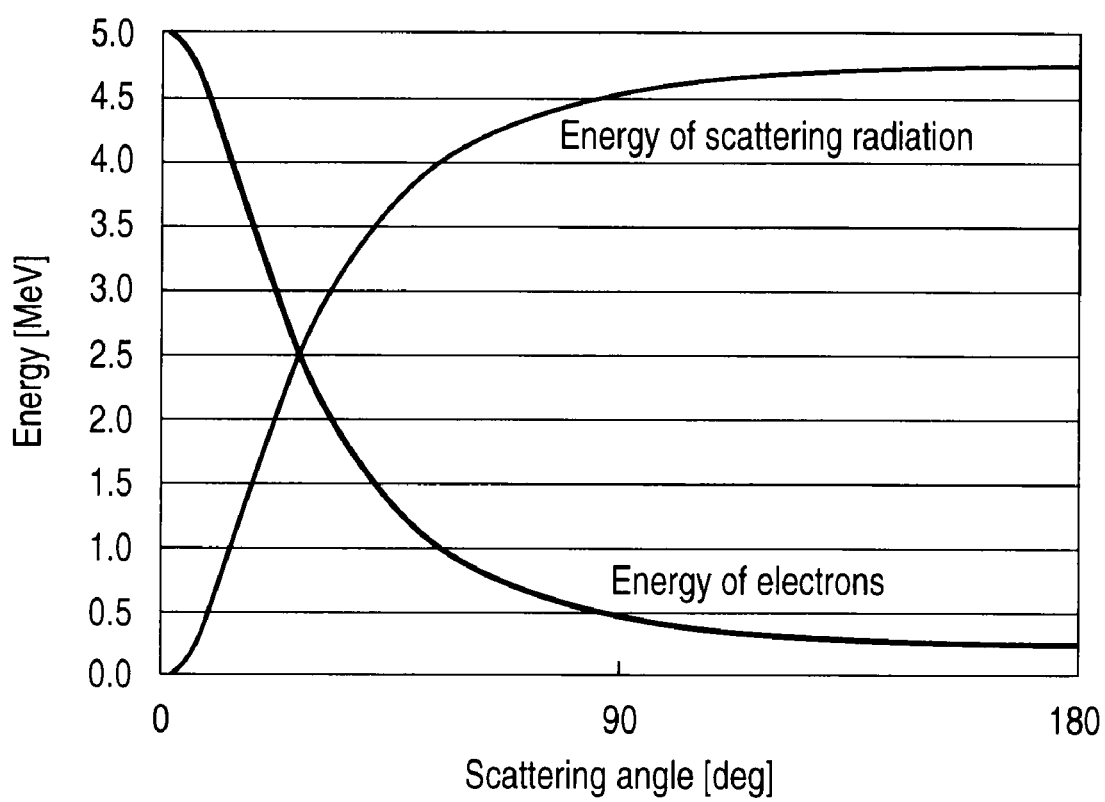
F I G. 1 2

On assumption that water is homogeneous, density of voxel is about 2.3 times as high as actual density, and absorbed dose similarly changes.

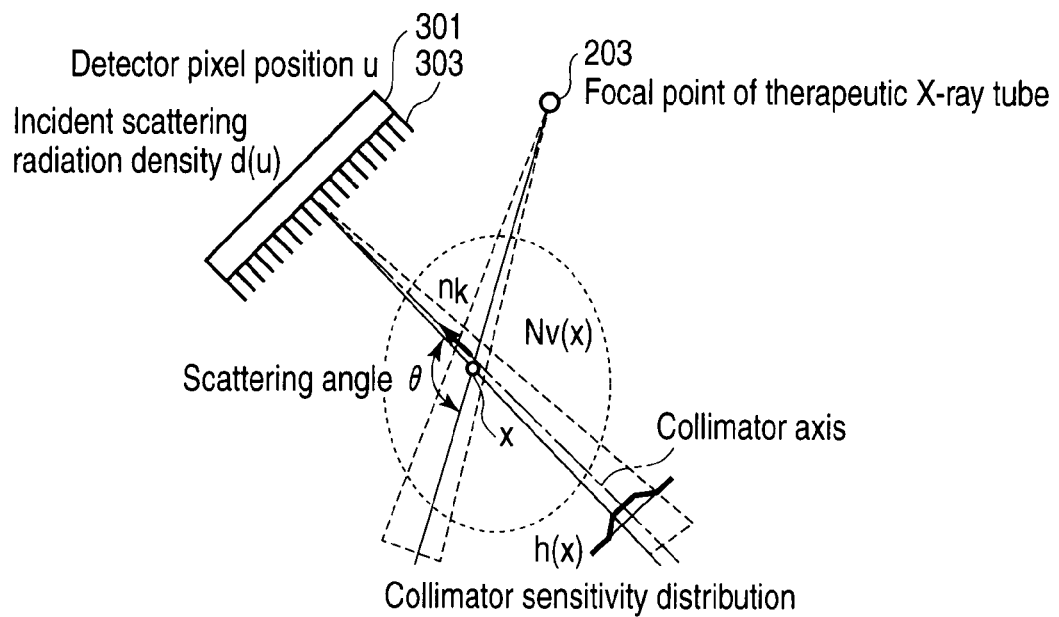
F I G. 3 2 A
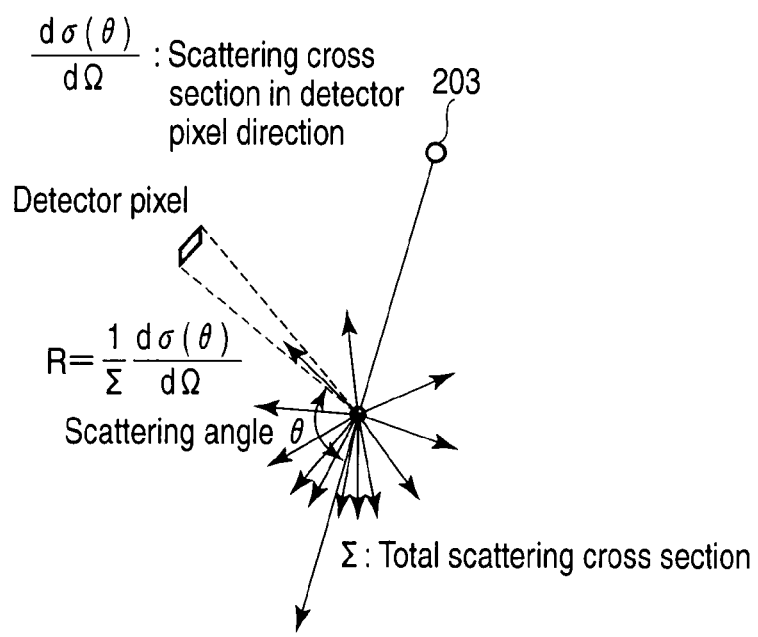
F I G. 3 2 B

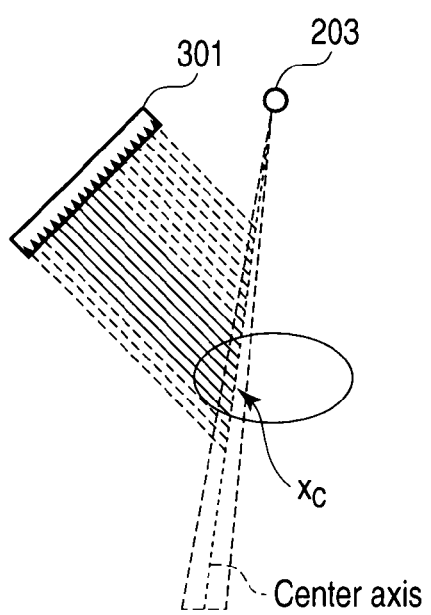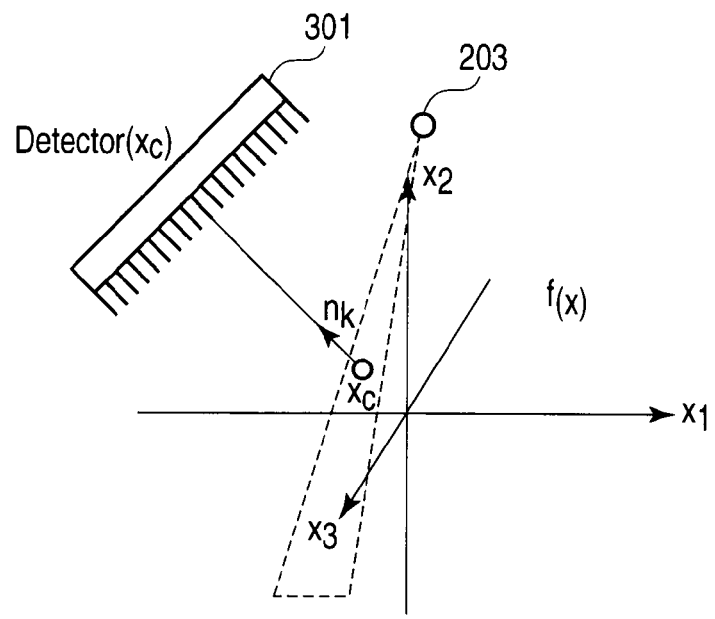
FIG. 35A　　　　　　FIG. 35B
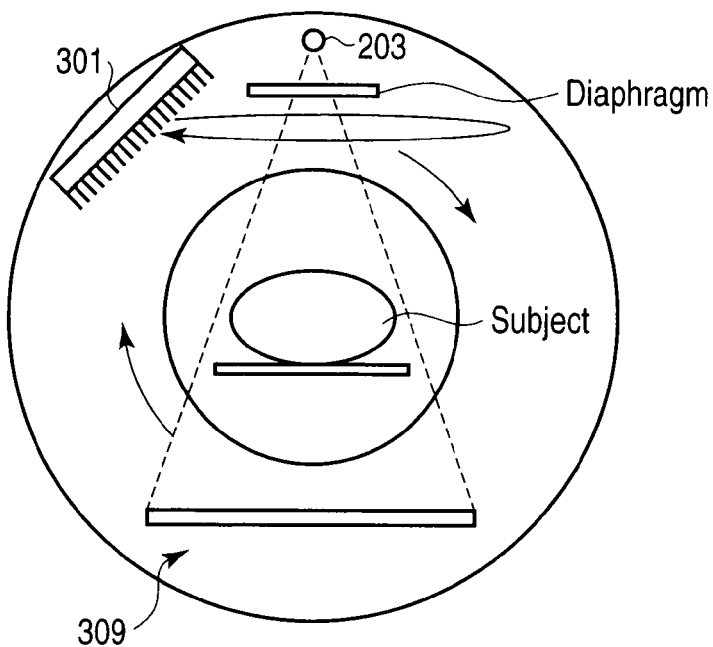
FIG. 36

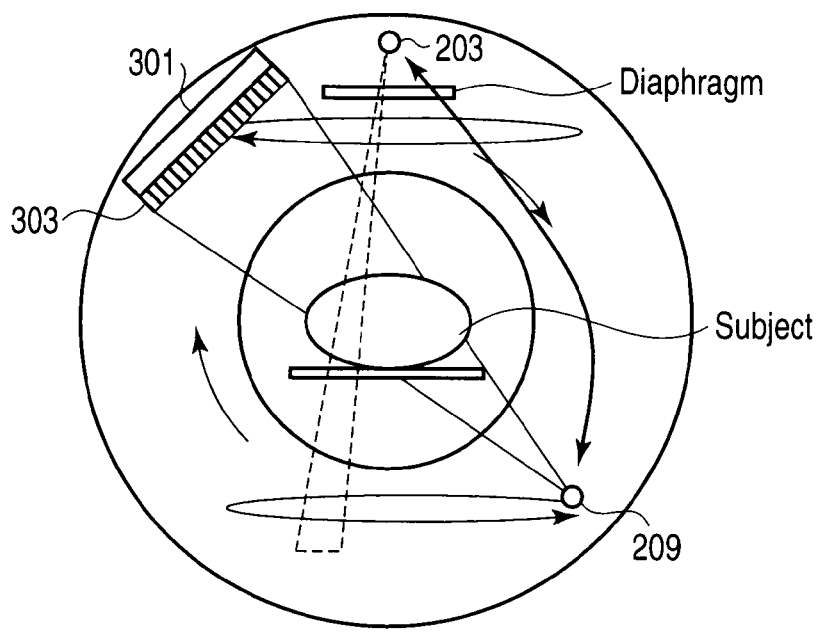
F I G. 37
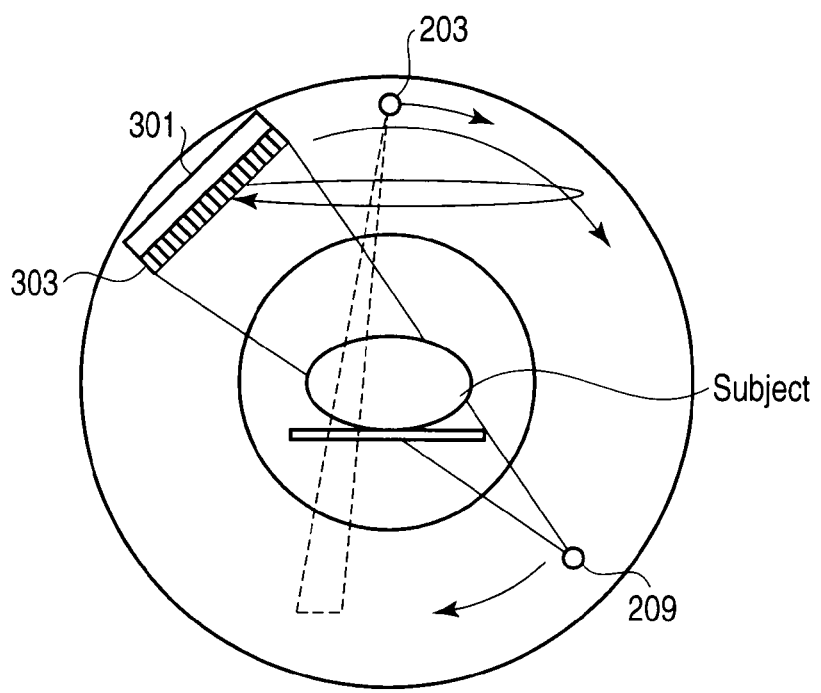
F I G. 38

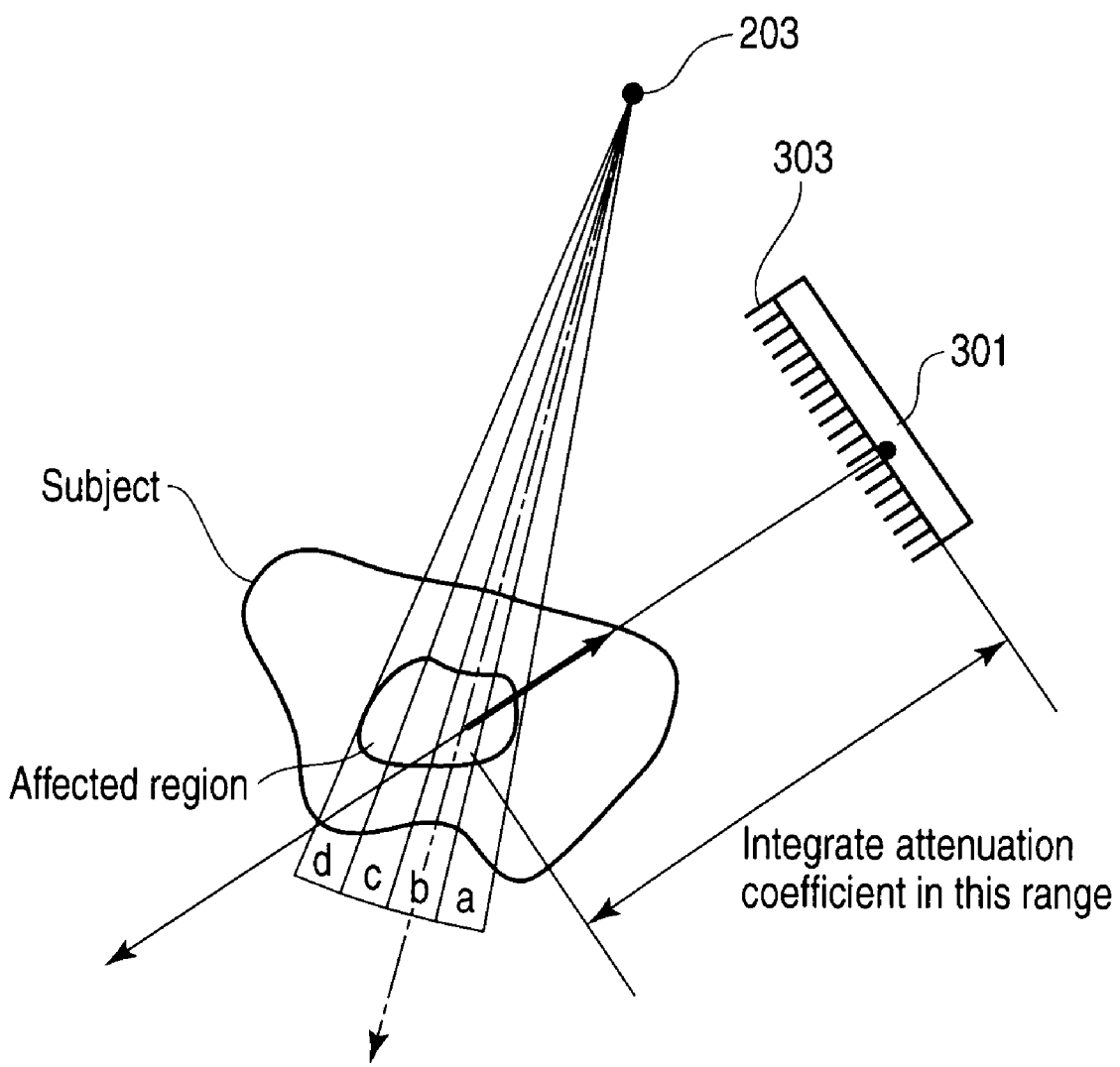
F I G. 39

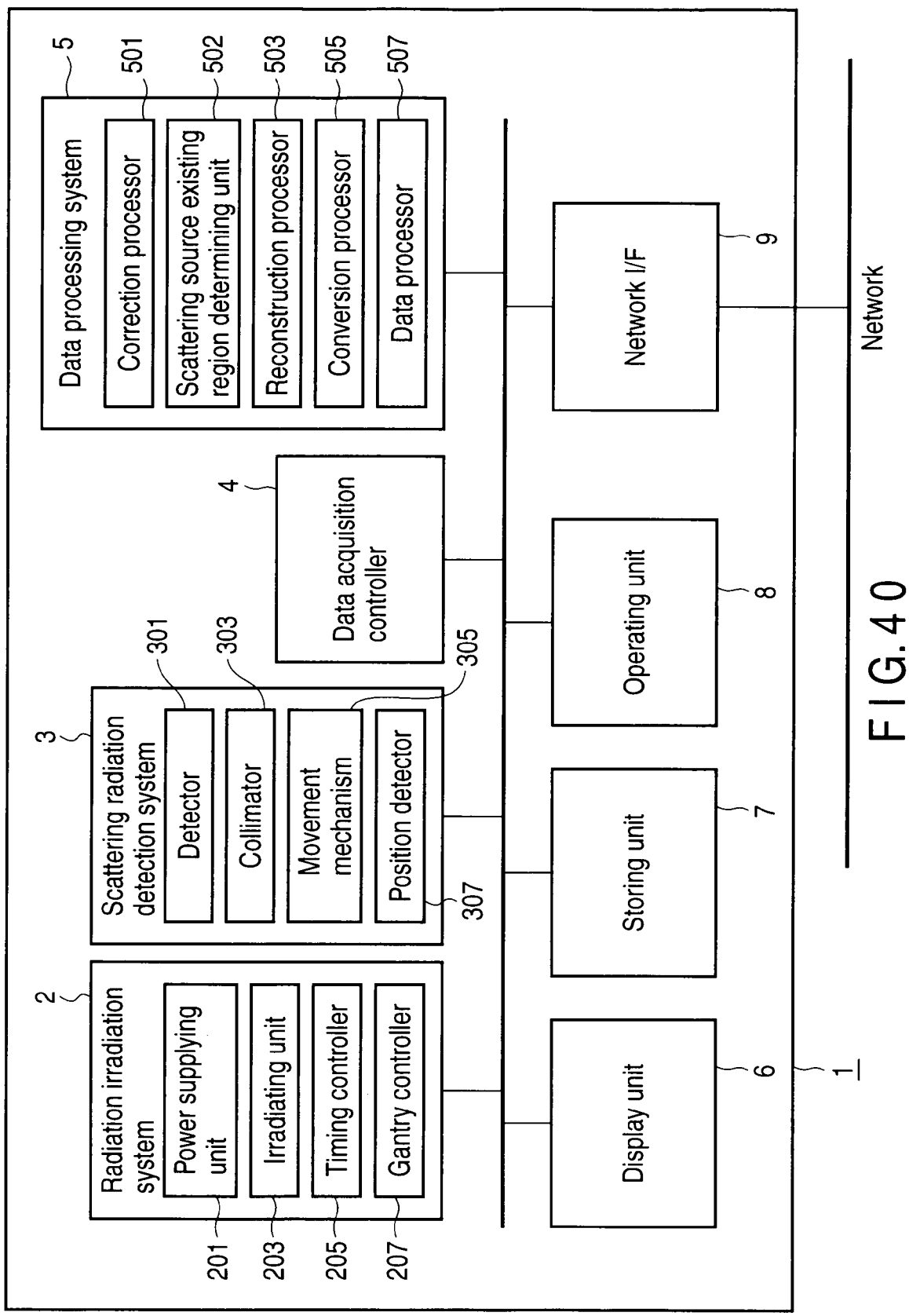
F I G. 40

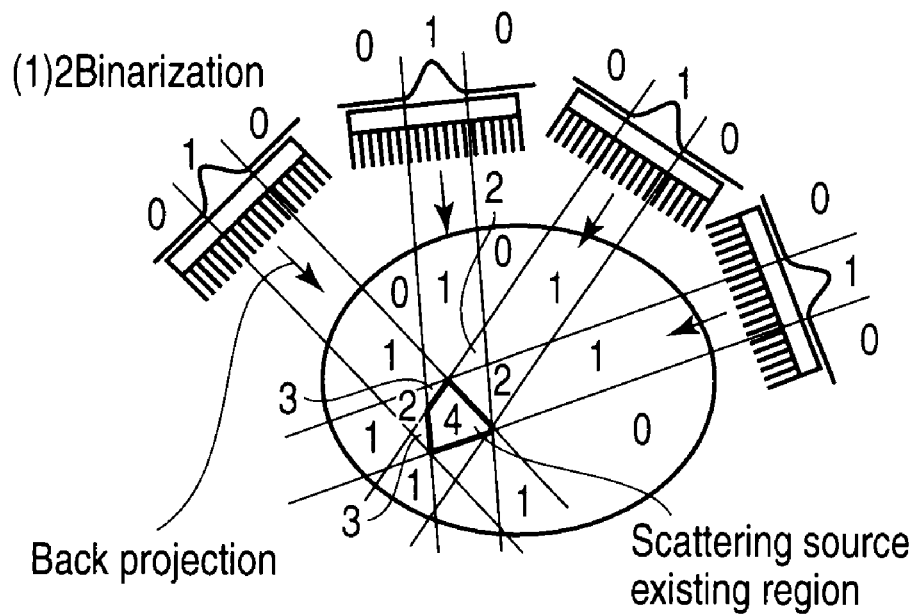
F I G. 4 1 A
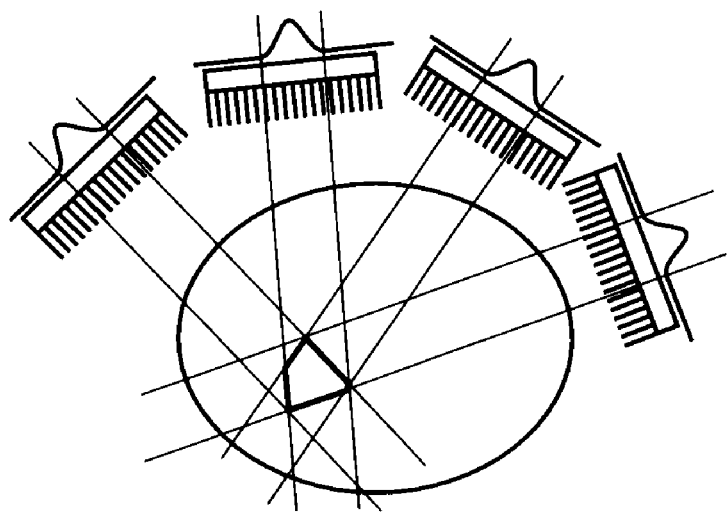
F I G. 4 1 B

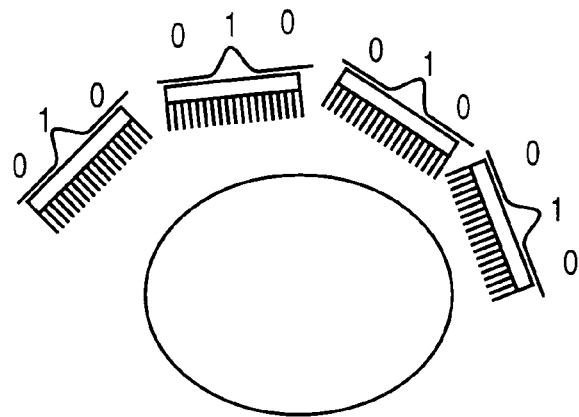
F I G. 4 4 A
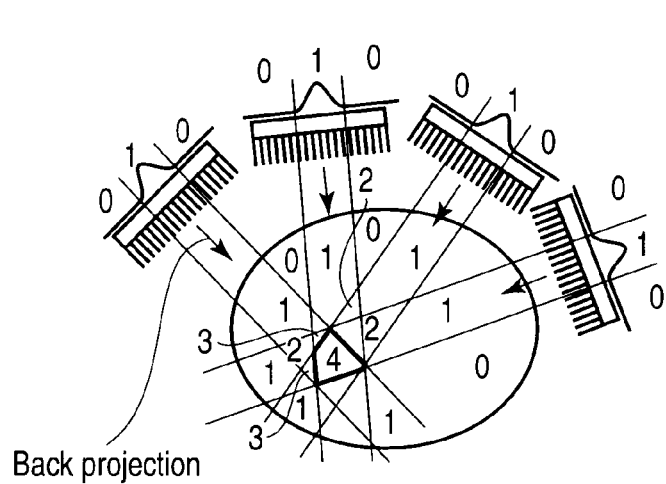
F I G. 4 4 B
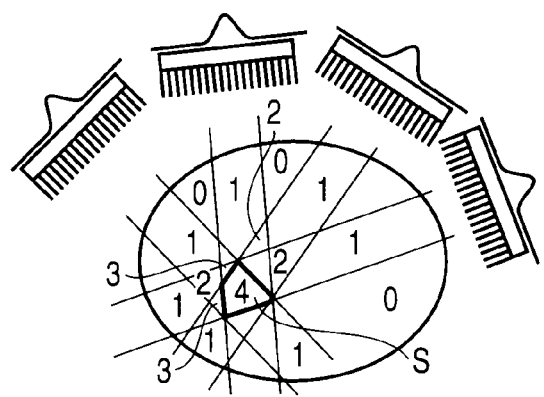
F I G. 4 4 C

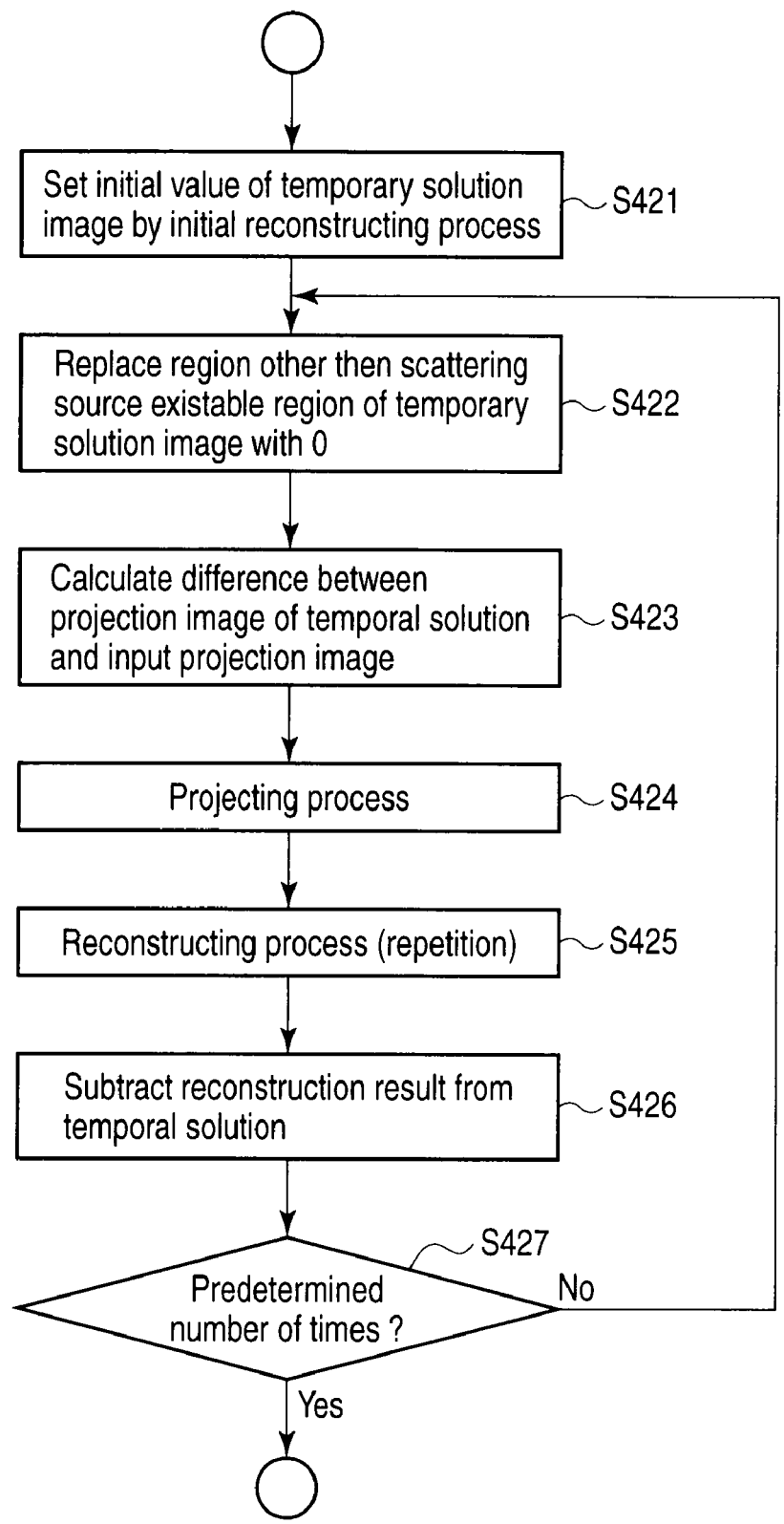
F I G. 4 5

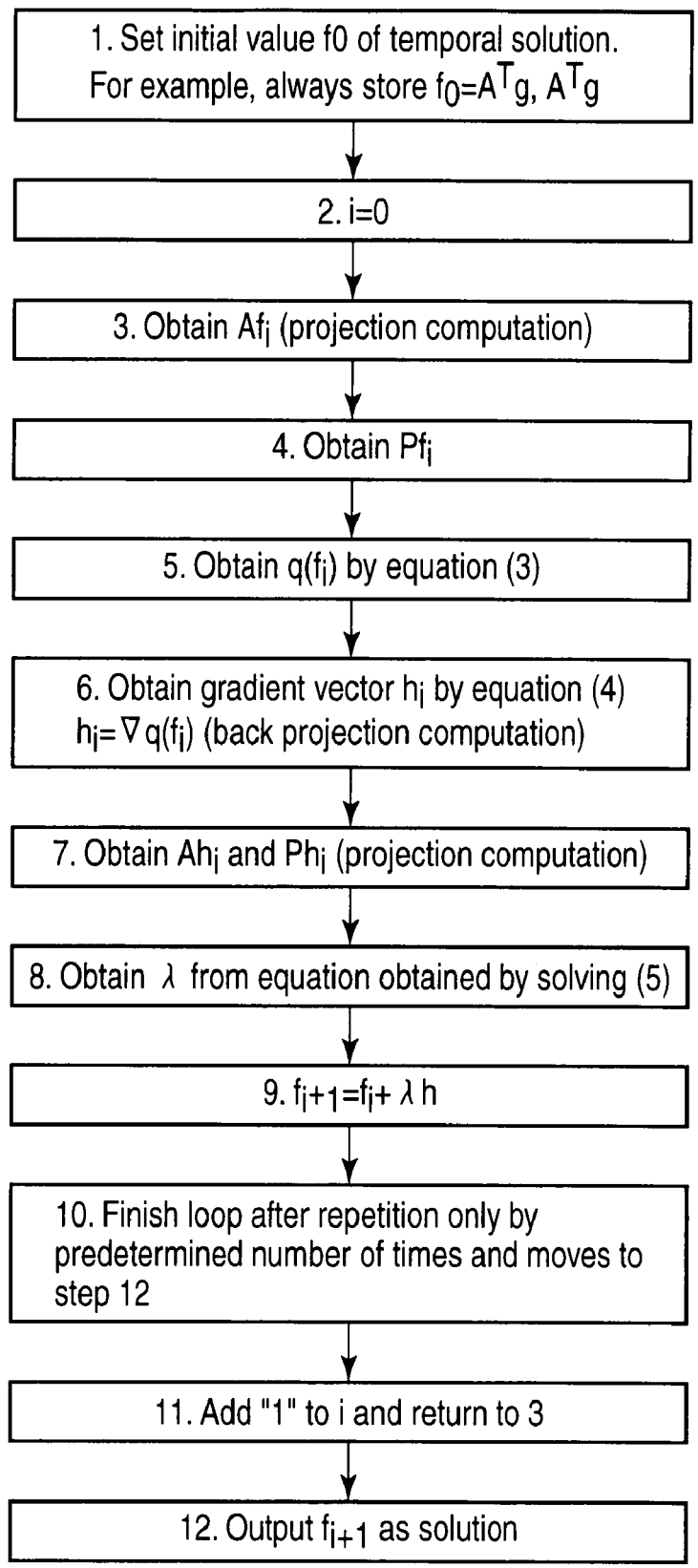
F I G. 4 6

FIG.50A
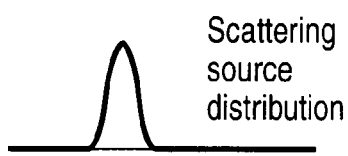
Scattering source distribution
FIG.50C
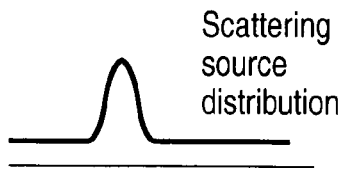
Scattering source distribution
FIG.50B
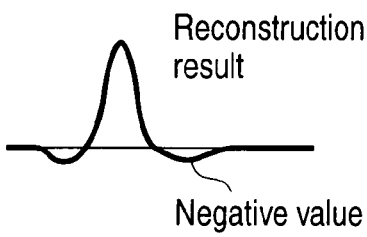
Reconstruction result
Negative value
FIG.50D
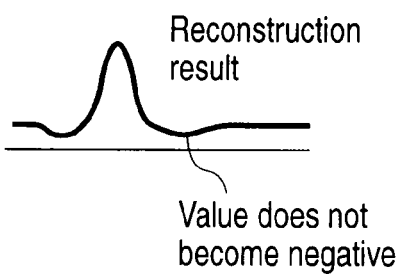
Reconstruction result
Value does not become negative
FIG.51A
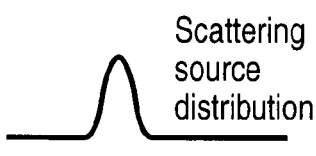
Scattering source distribution
FIG.51B
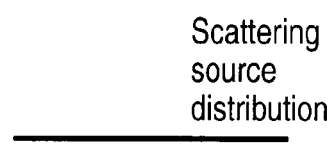
Scattering source distribution
FIG.51C
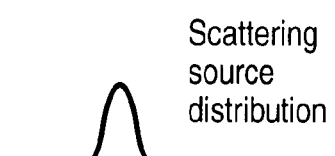
Scattering source distribution
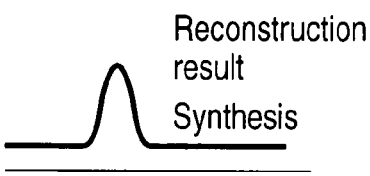
Reconstruction result
Synthesis
Reconstruction result
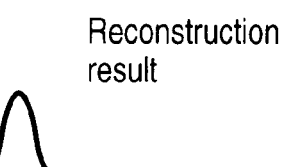
Reconstruction result
FIG.51D          FIG.51E          FIG.51F ND RADIOTHERAPEUTIC SYSTEM AND
RADIOTHERAPEUTIC DOSE DISTRIBUTION
MEASURING METHOD

CROSS-REFERENCE TO RELATED
APPLICATIONS

This application is based upon and claims the benefit of priority from prior Japanese Patent Applications No. 2007-331108, filed Dec. 21, 2007; No. 2008-026733, filed Feb. 6, 2008; No. 2008-033361, filed Feb. 14, 2008; and No. 2008-033362, filed Feb. 14, 2008, the entire contents of all of which are incorporated herein by reference.

BACKGROUND OF THE INVENTION

1. Field of the Invention

The present invention relates to a radiotherapeutic system and a radiotherapeutic dose distribution measuring method, in radiation treatment performed by emitting radiation from the outside of the body of a patient to an affected region (treatment for applying X-rays from the outside of the body of a patient to an affected region), capable of preventing excessive irradiation to an affected area and a normal tissue by measuring an actually irradiated region in the patient and actual dose and providing the result in a predetermined form.

2. Description of the Related Art

In radiation treatment typified by external X-ray radiation therapy, before the treatment, an irradiation plan (the direction and the dose of radiation to an affected region) is made on a patient image. On the basis of the irradiation plan, irradiation to the patient is performed. However, at present, there is no means for confirming whether irradiation is actually performed to the patient with the planned position and dose or not. Even if insufficient irradiation to an affected region or excessive irradiation to a normal tissue occurs, it is not noticed. In some cases, using a phantom and an X-ray detector prior to irradiation, whether planned irradiation can be performed or not is confirmed. However, it is difficult to place a patient in a position according to the irradiation plan, on a bed different from a phantom which is easily portable and whose position can be freely adjusted. The confirmation prior to radiation does not completely assure the planned irradiation to the patient.

A technique of acquiring a cross-sectional image by using scattering radiation is disclosed in Jpn. Pat. Appln. KOKAI Publication No. 5-146426. According to the technique, scattered X-rays in an X-ray subject are detected to obtain a cross-sectional image of the subject. The characteristic of the technique is that a scan is performed with a pencil beam and a three-dimensional scattering radiation image of the subject is reconstructed. That is, the technique assumes only the pencil beam but is not directed to obtain a scattering radiation image of a region through which a beam having a limited width passes (a spatial distribution of dose of a therapeutic beam), which is used in X-ray treatment. Since forward scattering is dominant in the scattering in a subject of a therapeutic beam (a few MeV) having high energy, when a detector is disposed in the incident X-ray direction, it is difficult to distinguish scattering radiation and penetrating radiation from each other. A correcting process is therefore necessary for detection of scattering radiation.

Amid mounting social concern over medical errors, also in radiation treatment, excessive irradiation to a patient was reported and it became an issue. It is predicted that recording of the "fact" of medial acts performed such as a region in a patient and a dose of irradiation is becoming important more and more. In the field of external X-ray radiation therapy, attempts to irradiate an affected region more precisely are being made such as a method of irradiation so as to synchronize and trace motion of a tumor in a patient caused by breathing or the like, a method of collimating a therapeutic X-ray beam in accordance with the shape of a tumor and irradiating the tumor with the beam, and the like. The object of the precise irradiations is to concentrate the dose to an affected region. Therefore, if the therapeutic X-ray beam is off from the irradiation target, normal tissue is considerably damaged. As the irradiation is becoming more precise, it is becoming more important to check if the irradiation is performed as planned.

BRIEF SUMMARY OF THE INVENTION

In view of the circumstances, an object of the present invention is to provide a radiotherapeutic system and a radiotherapeutic dose distribution measuring method, in external X-ray radiation therapy, capable of preventing excessive irradiation to an affected area and a normal tissue by measuring an actually irradiated region in the patient and actual dose and providing the result in a predetermined form.

According to an aspect of the present invention, there is provided a radiotherapeutic system which comprises: a irradiation unit which irradiates a subject with a radiotherapeutic beam; a detection unit which detects scattering radiation from the subject, which occurs on the basis of the radiotherapeutic beam, in a plurality of positions and generates scattering radiation data; a collimator which is arranged on the detection unit and causes the detection unit to detect scattering radiation at a predetermined scattering angle θ; and an image reconstruction unit which reconstructs a radiation dose image indicative of a distribution of radiation dose in the subject on the basis of the detected scattering radiation data in the plurality of positions.

According to another aspect of the present invention, there is provided a radiotherapeutic dose distribution measuring method which comprises: irradiating a subject with a radiotherapeutic beam; detecting scattering radiation from the subject, which occurs on the basis of the radiotherapeutic beam, in a plurality of positions and generates scattering radiation data; and reconstructing a radiation dose image indicative of a distribution of radiation dose in the subject on the basis of the detected scattering radiation data in the plurality of positions.

BRIEF DESCRIPTION OF THE SEVERAL
VIEWS OF THE DRAWING

FIG. 9 is a graph showing the Klein-Nishina formula;

FIG. 11 is a diagram showing a state of Compton scattering;

FIG. 12 is a graph showing the relation between energy of photons after Compton scattering and the scattering angle θ;

Figure 16A:
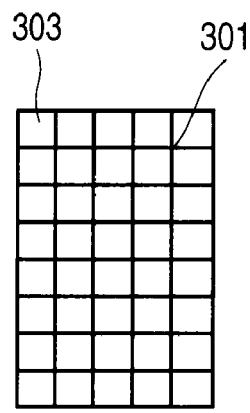
Figure 16B:
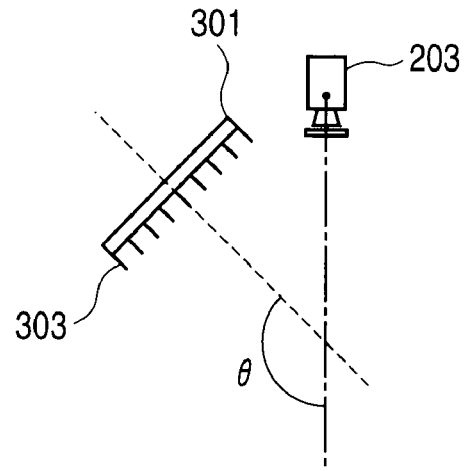
Figure 17:
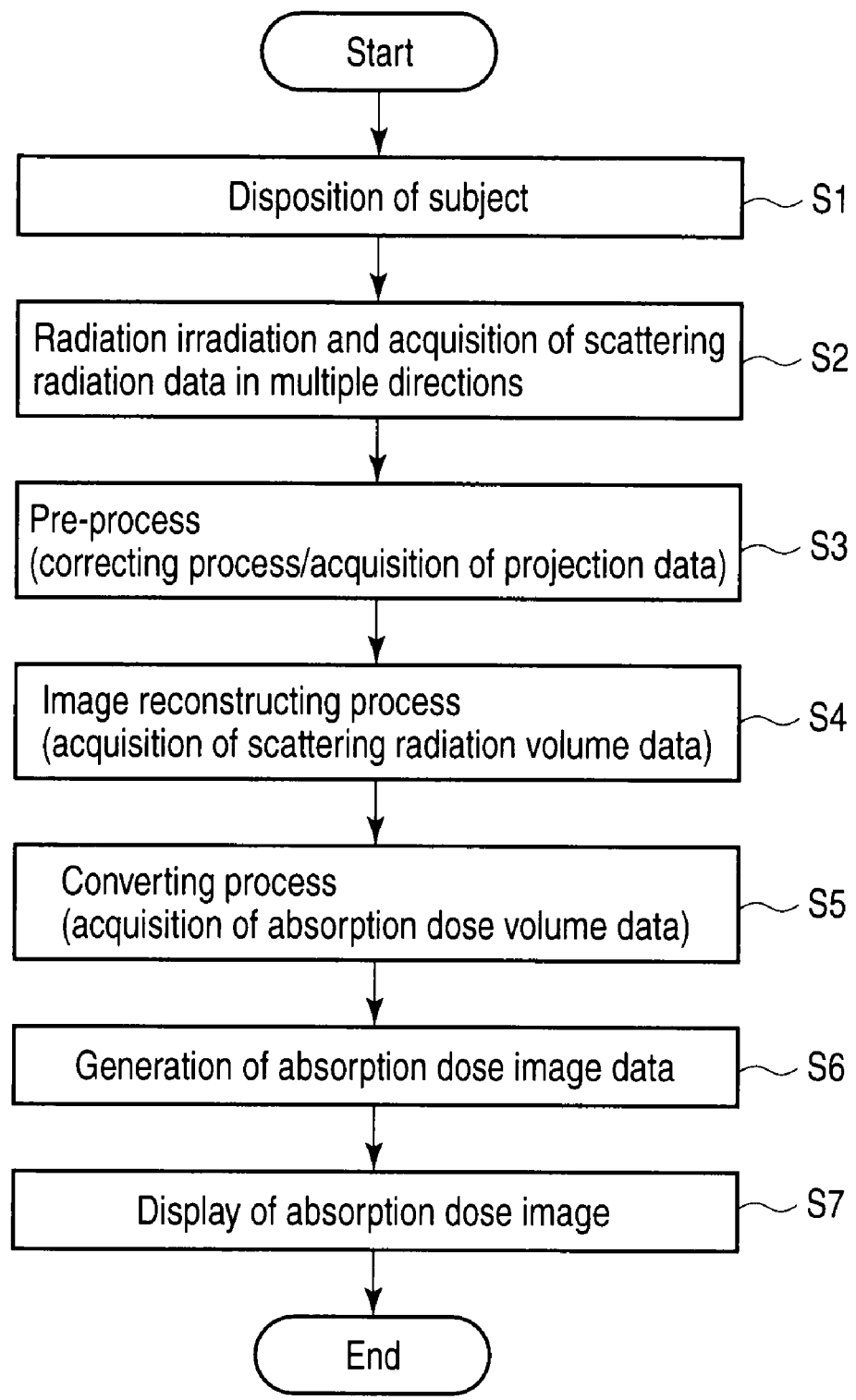
Figure 18:
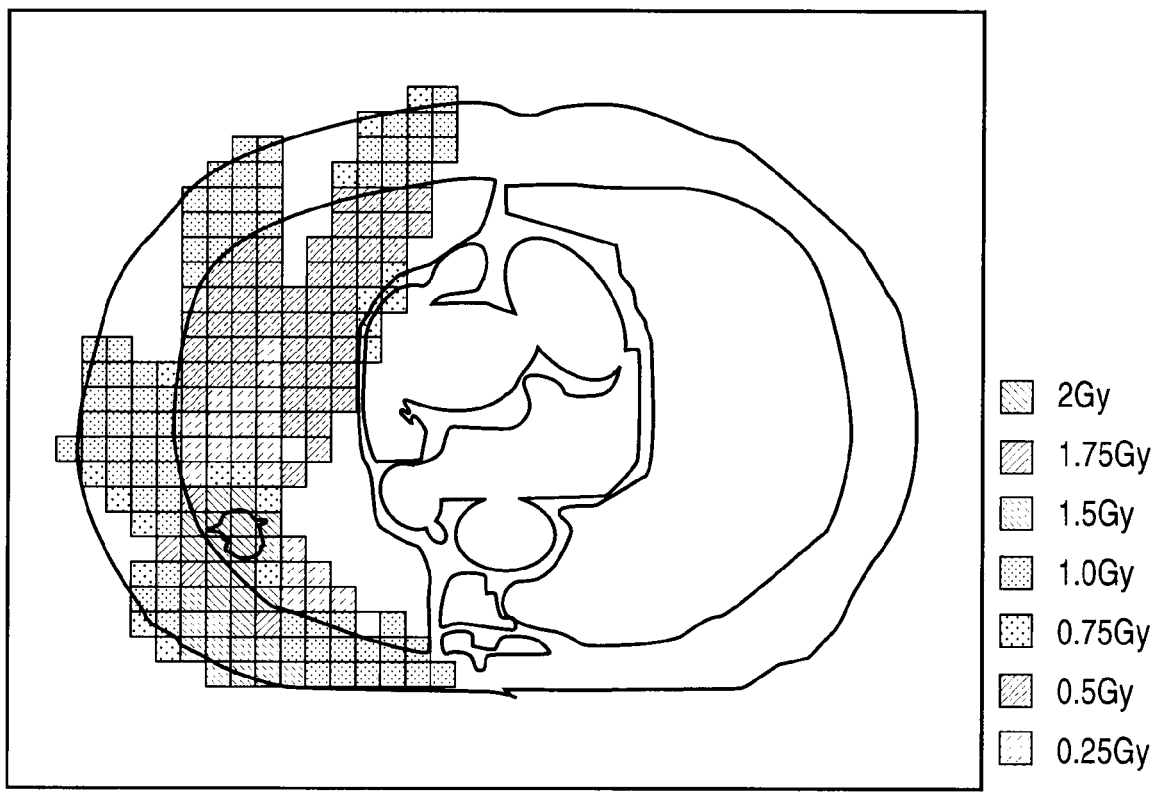
Figure 19:
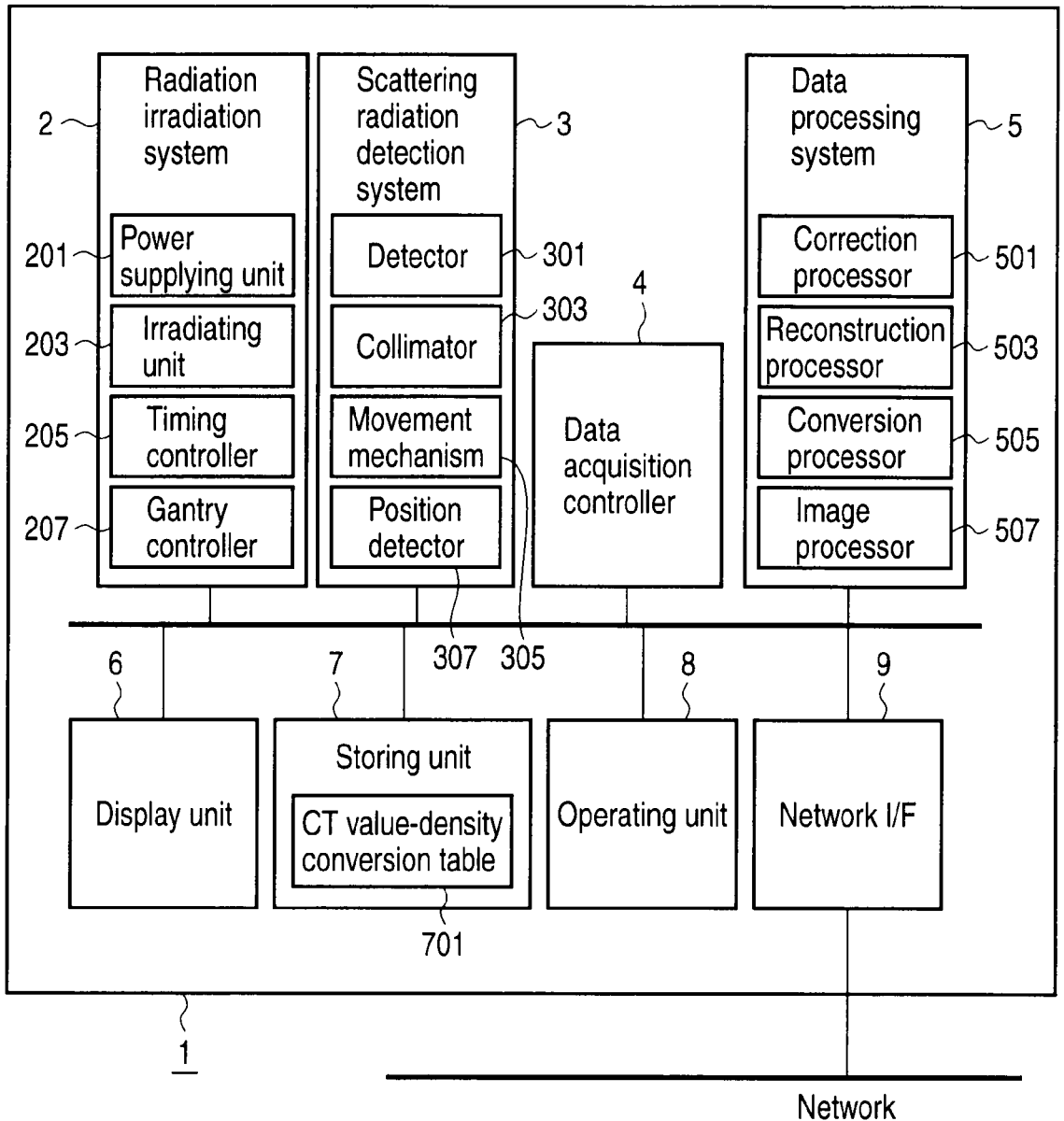
Figure 20:
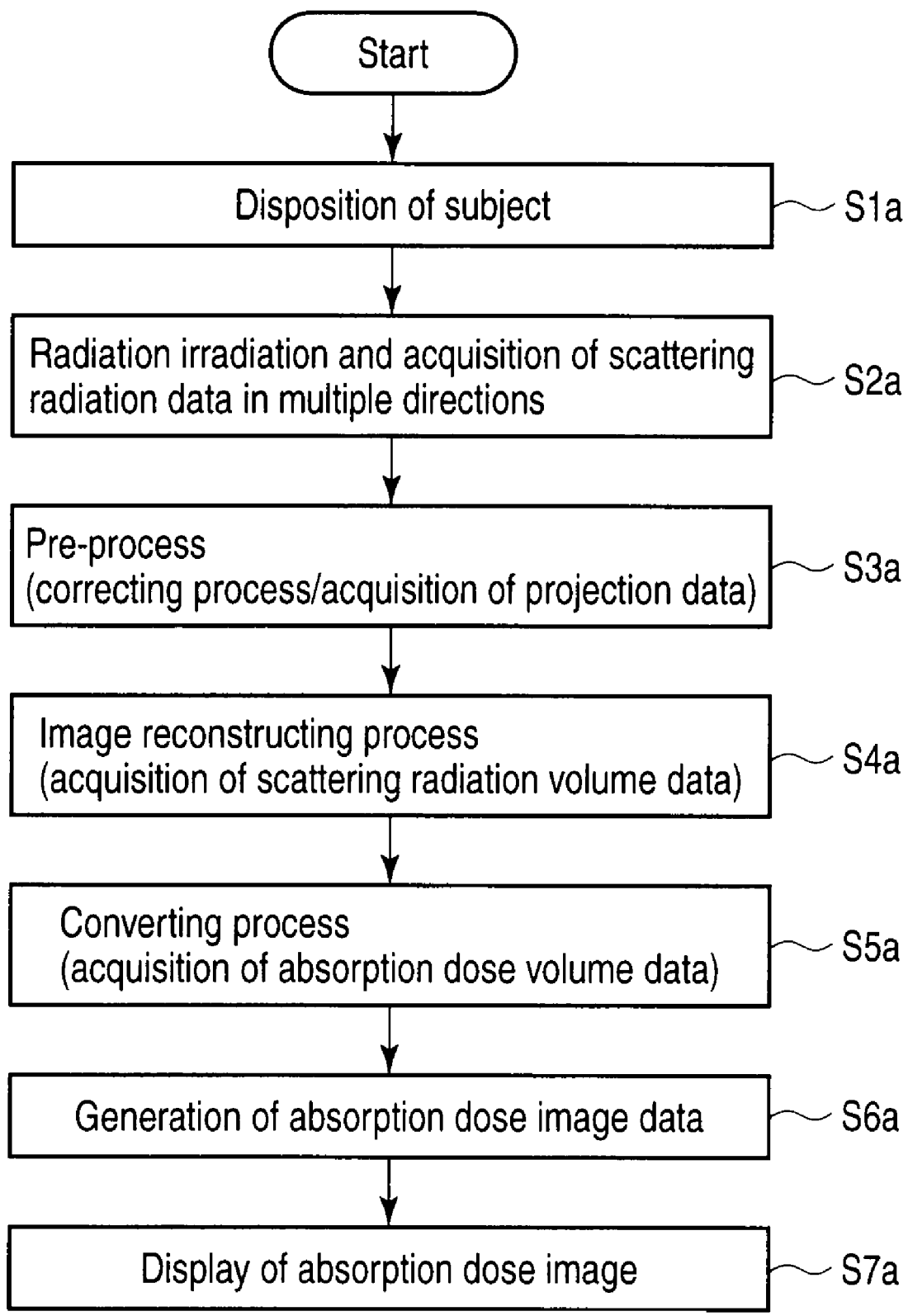
Figure 21:
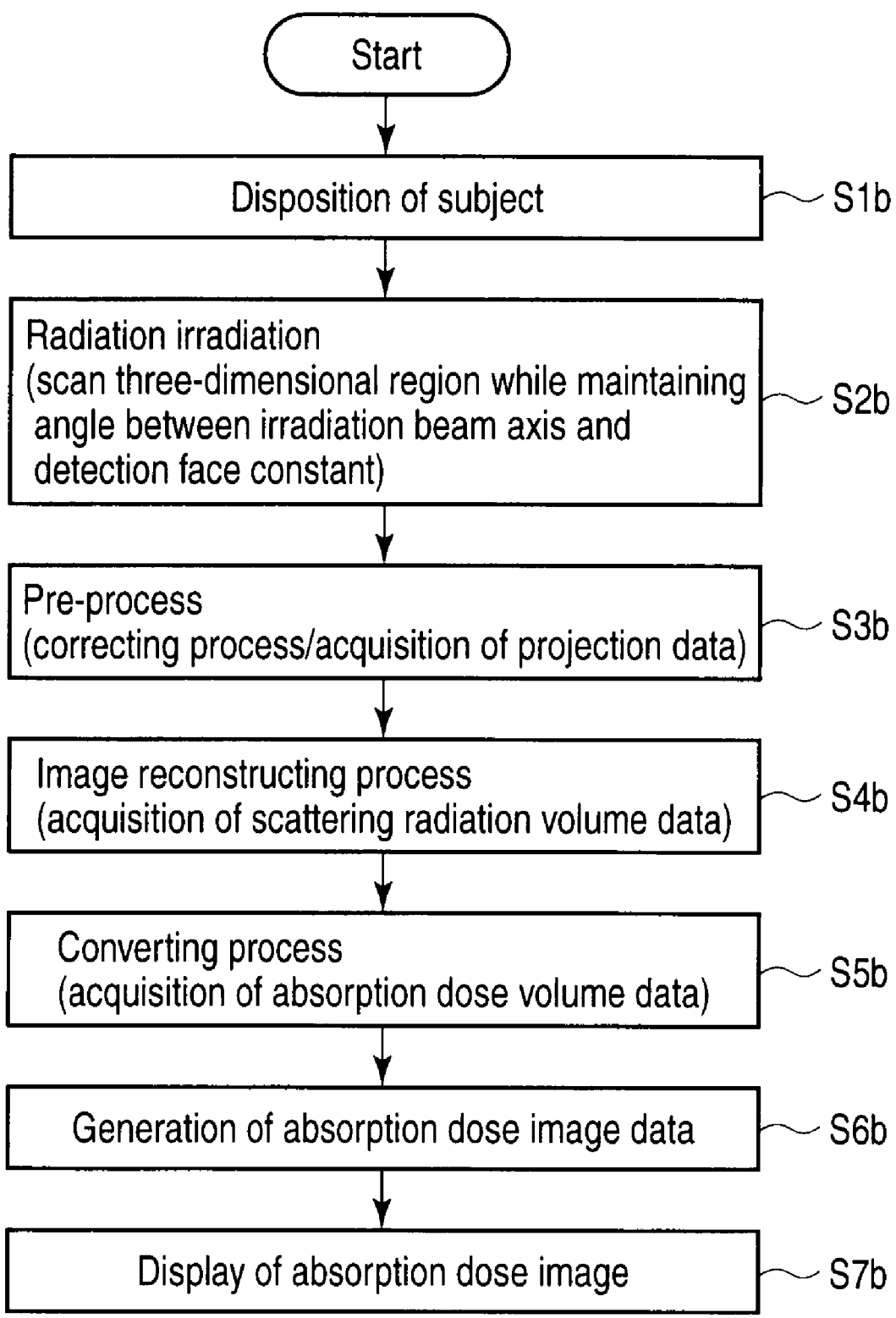
Figure 22:
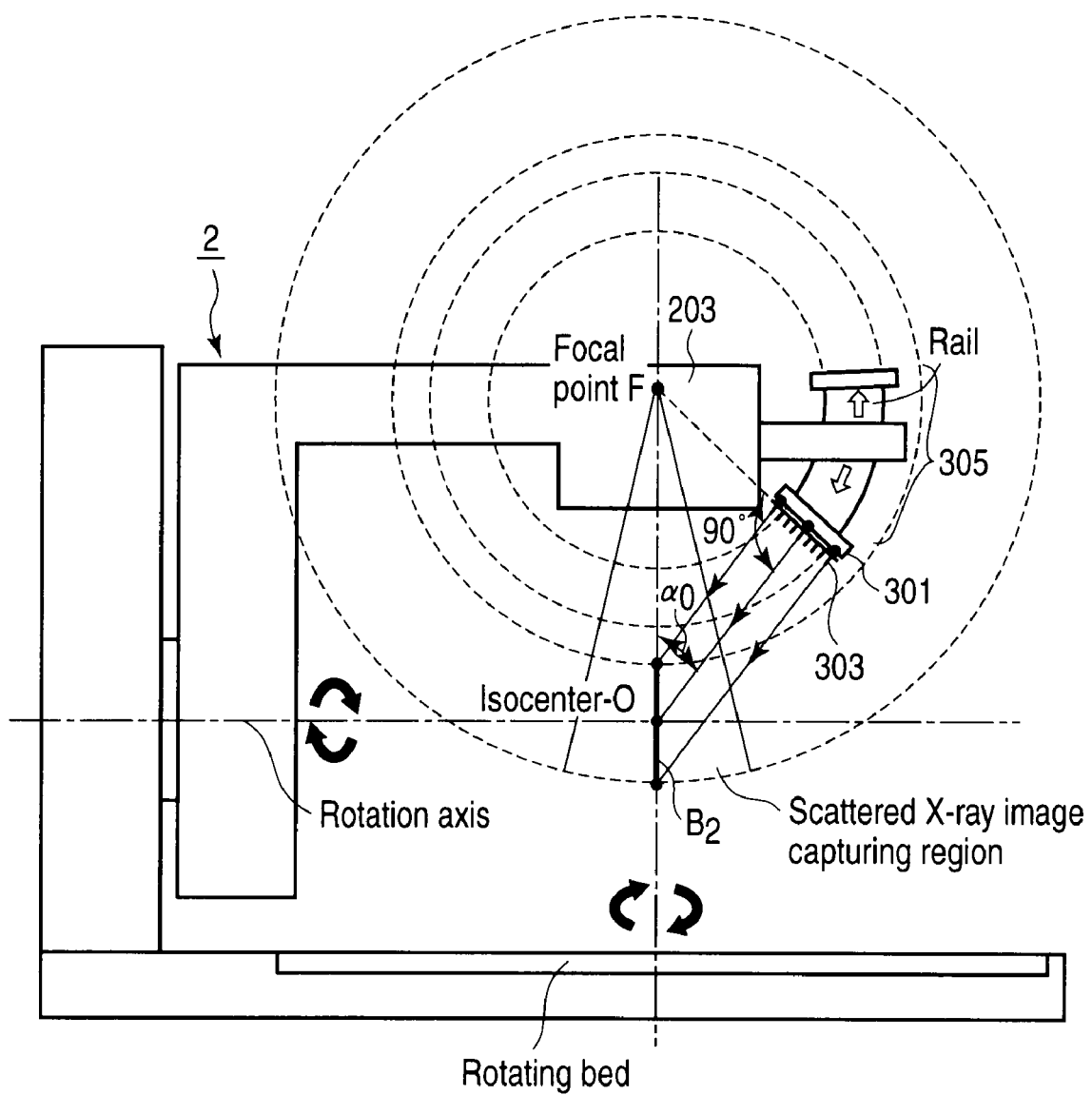
Figure 23:
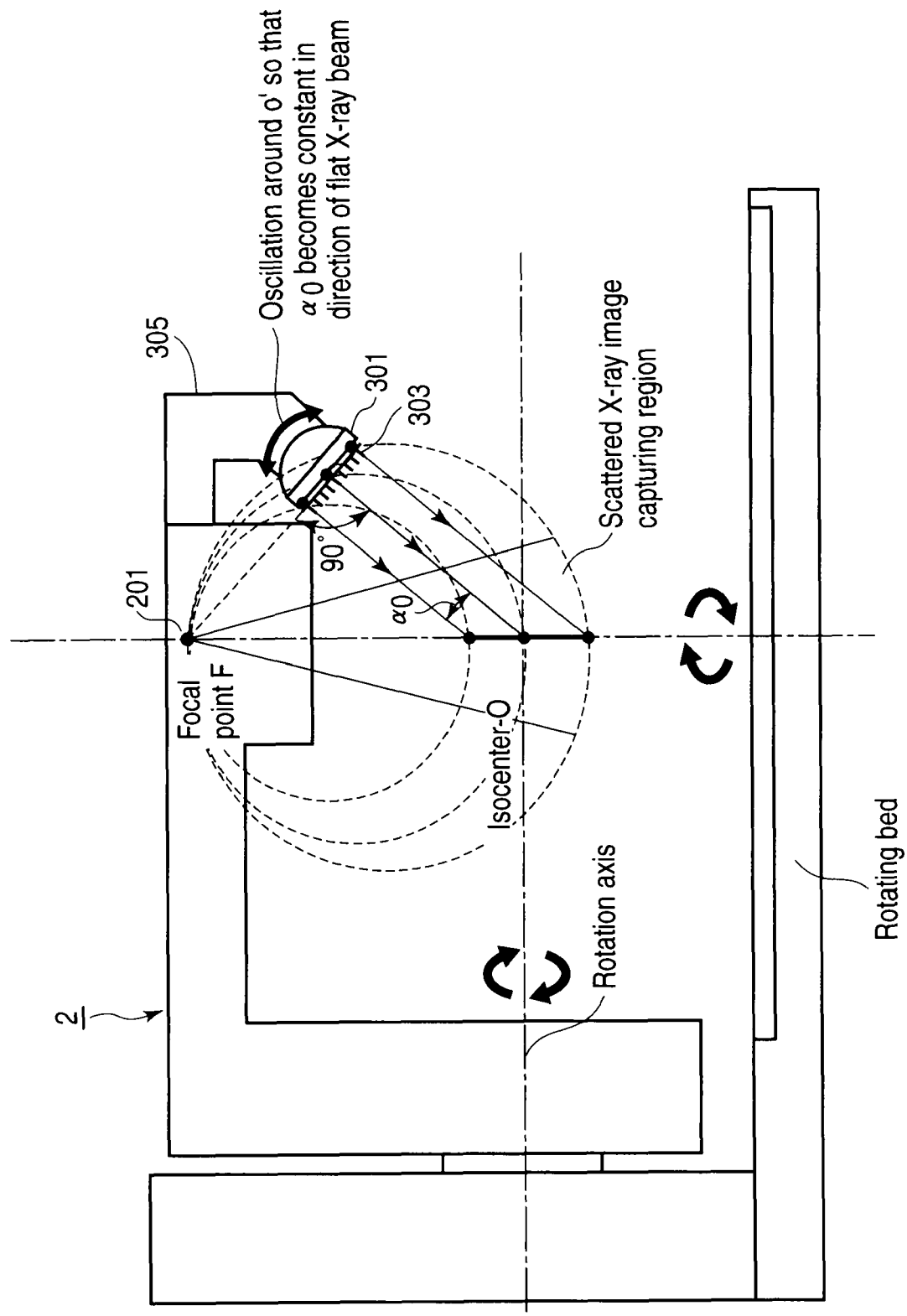
Figure 24:
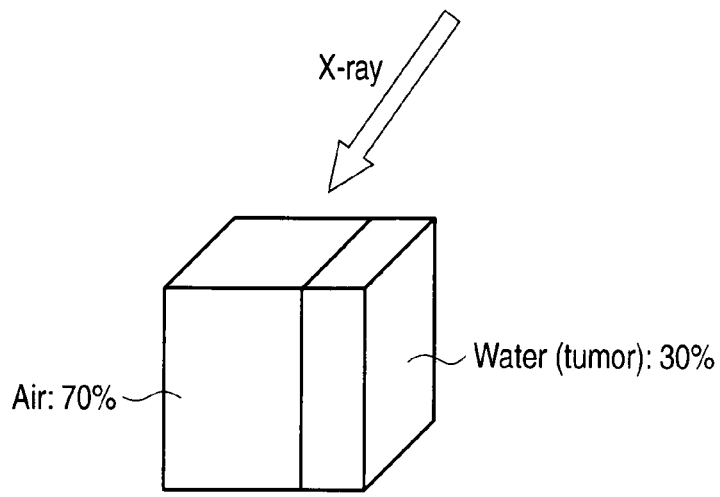
Figure 25:
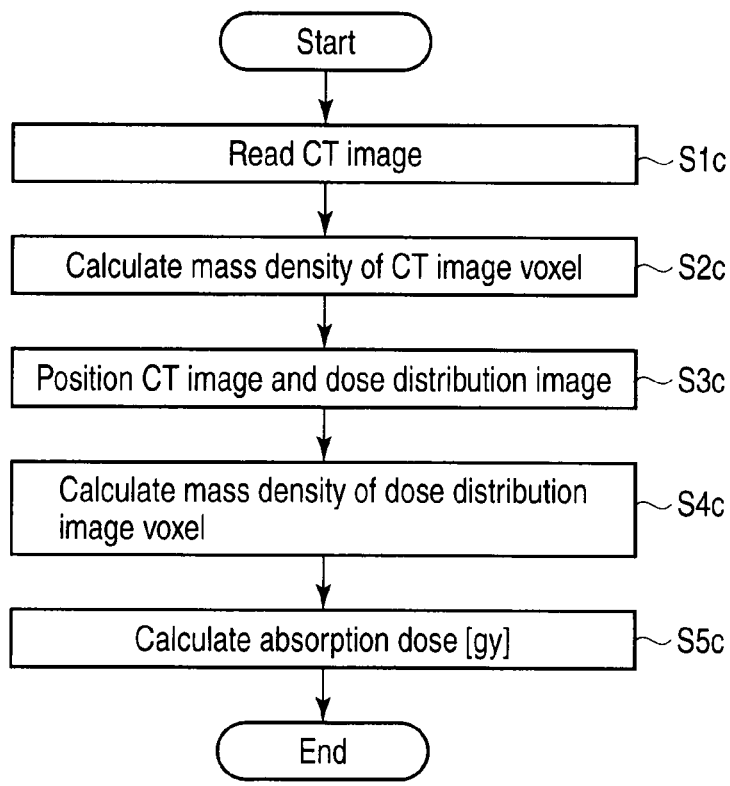
Figure 26:
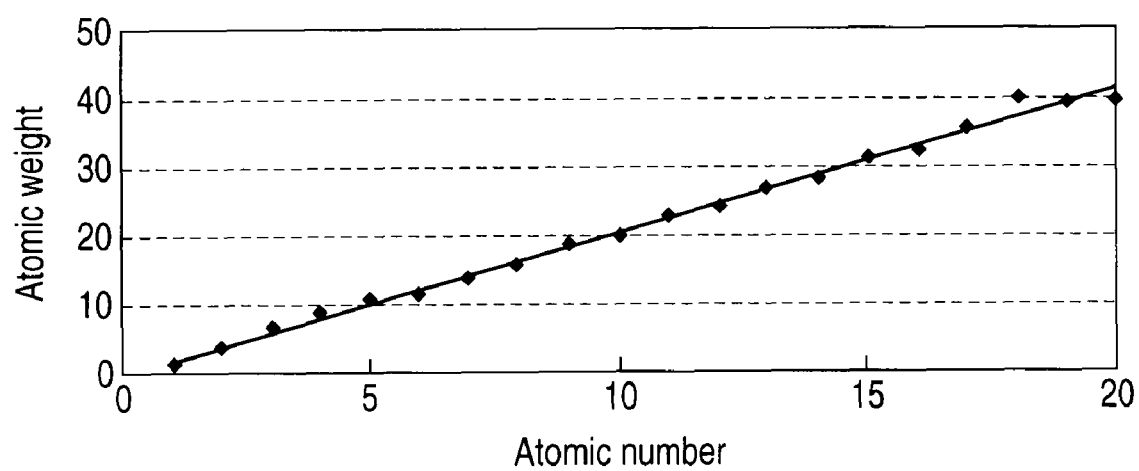
Figure 27:
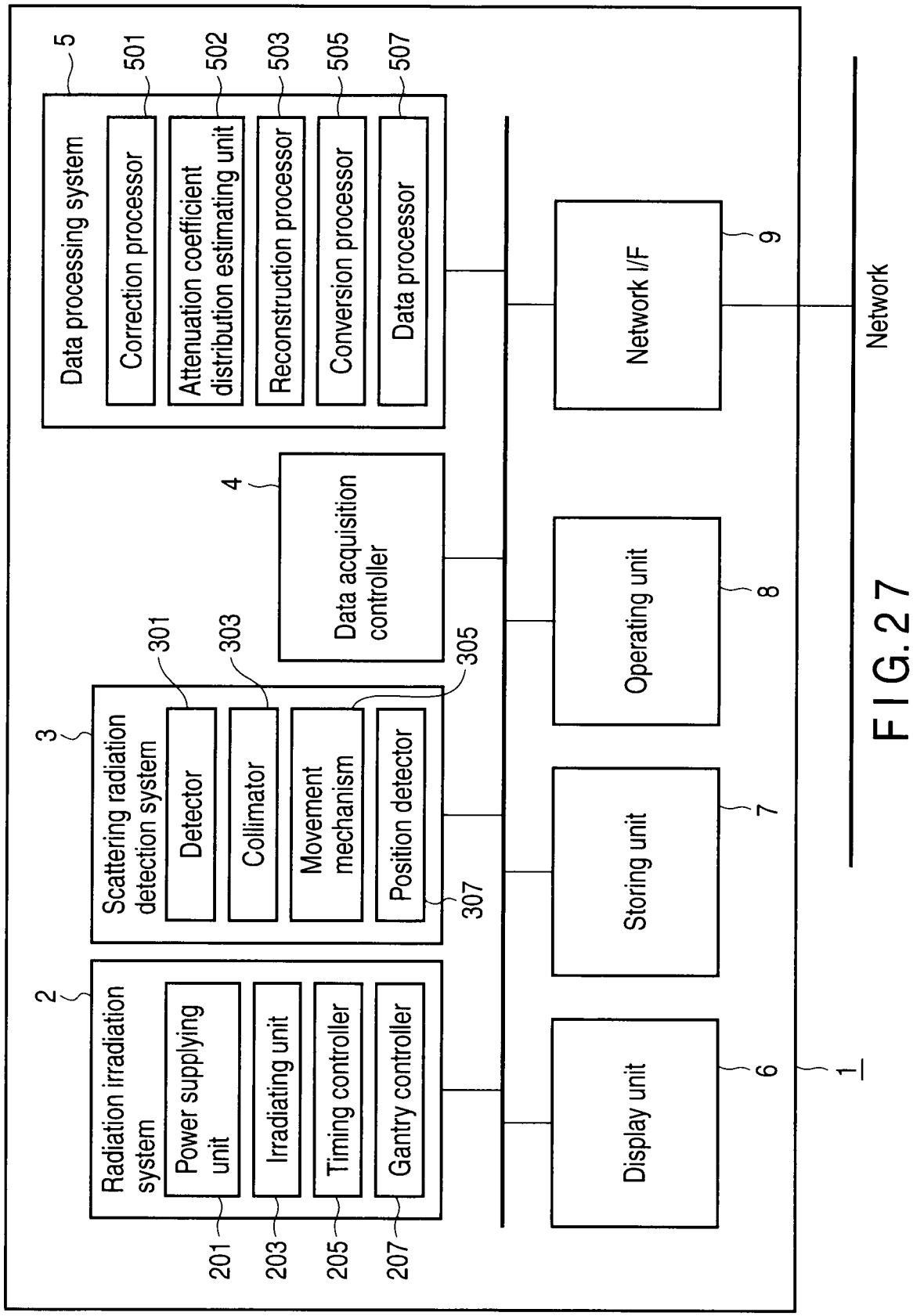
Figure 28:
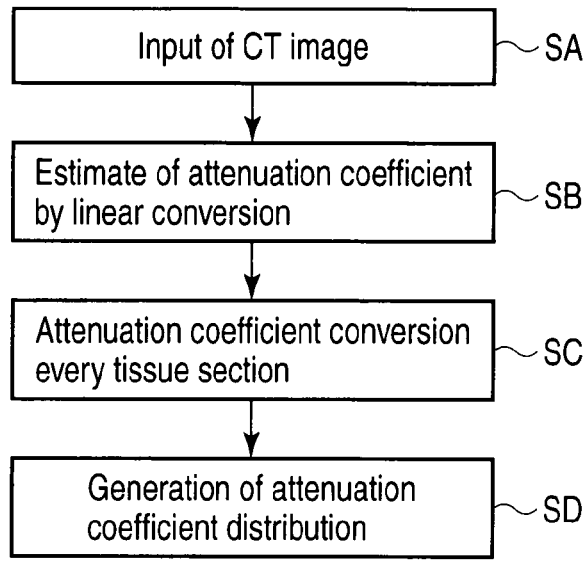
Figure 29:
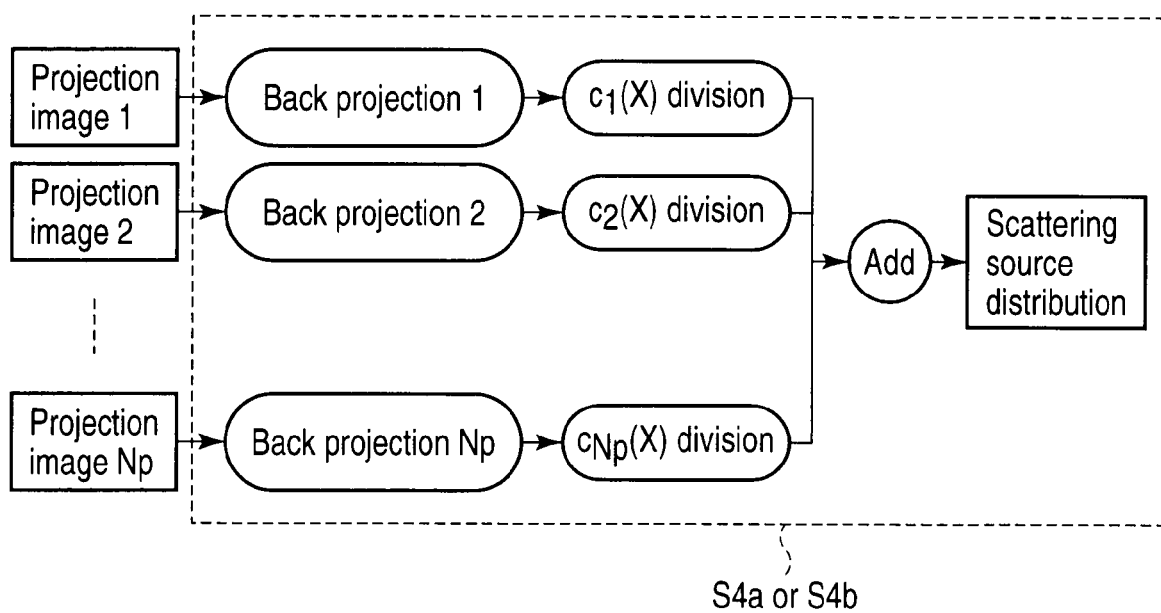
Figure 30:
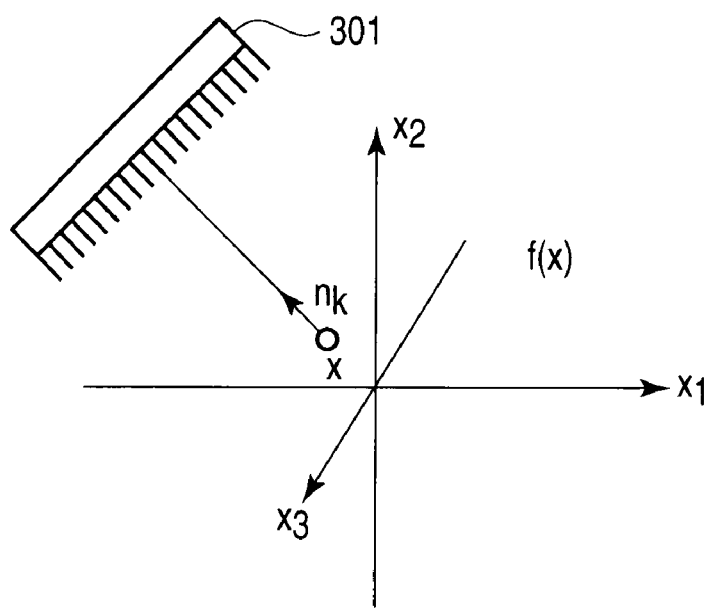
Figure 31:
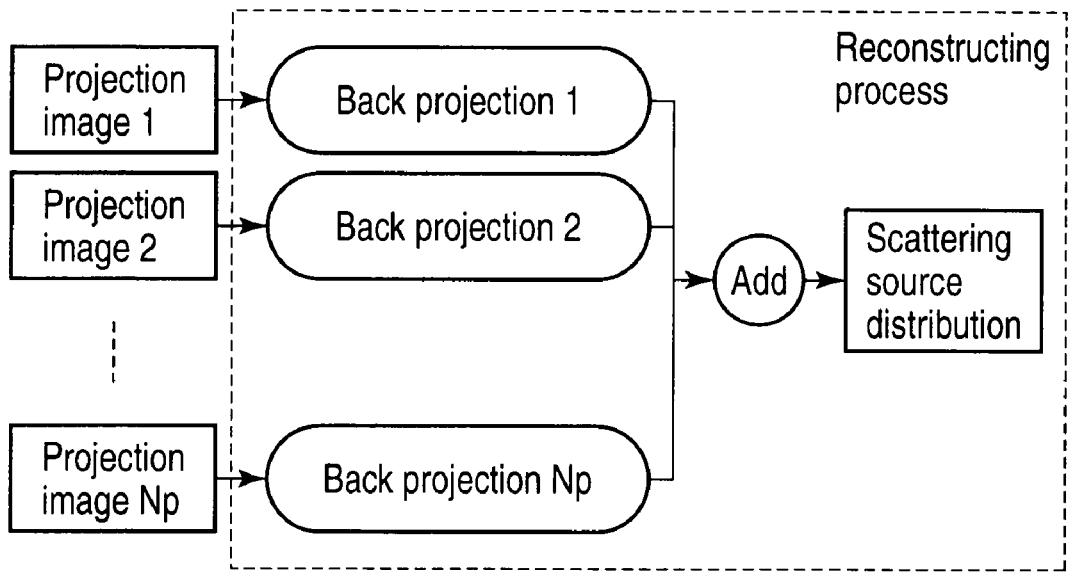
Figure 33:
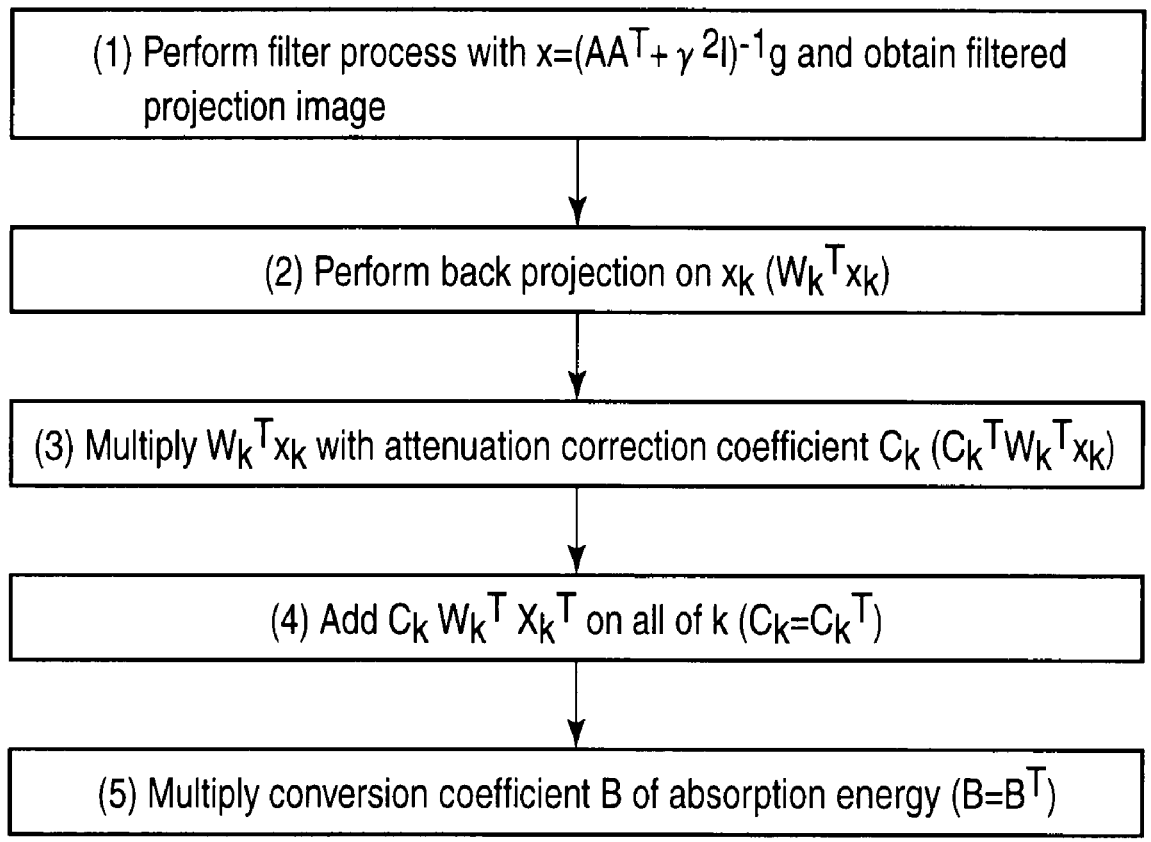
Figure 34:
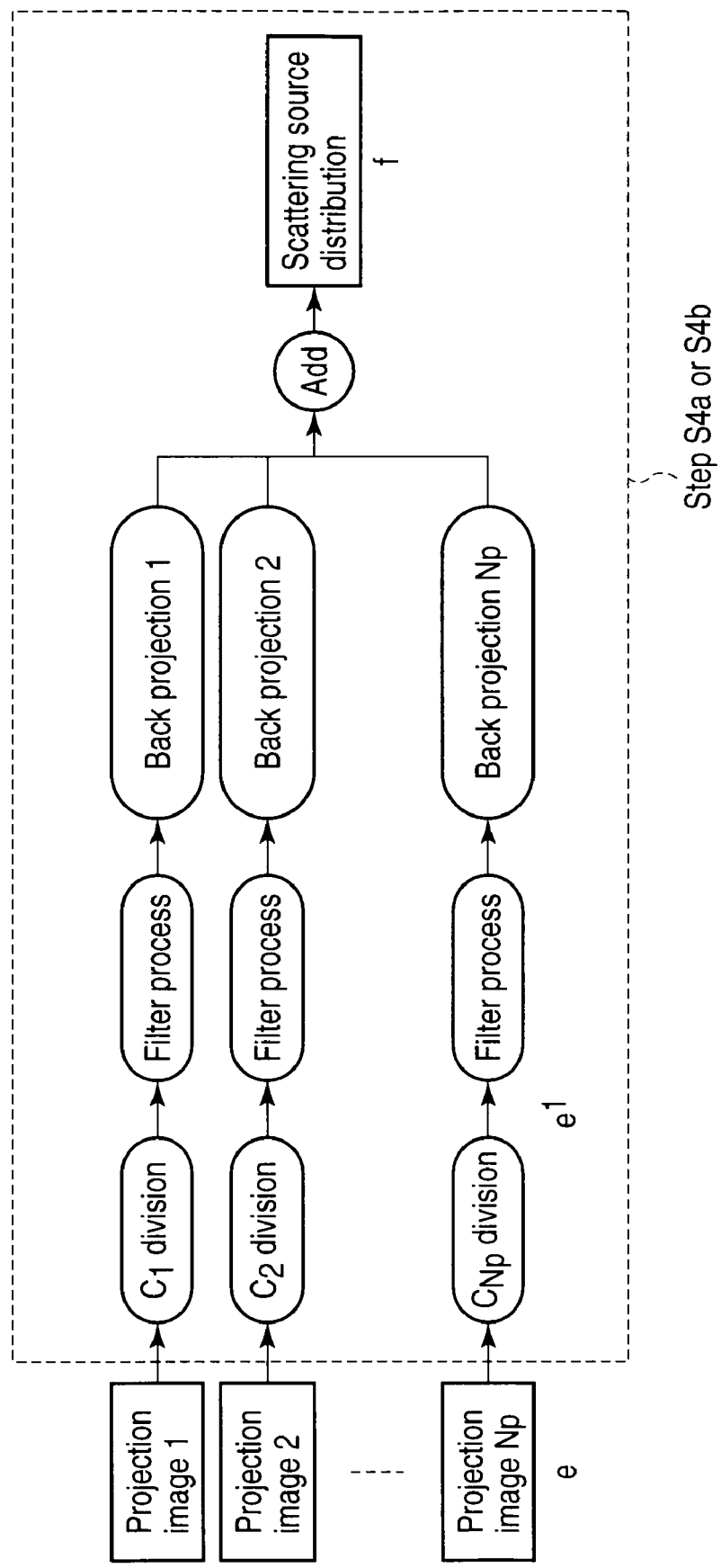
Figure 42:
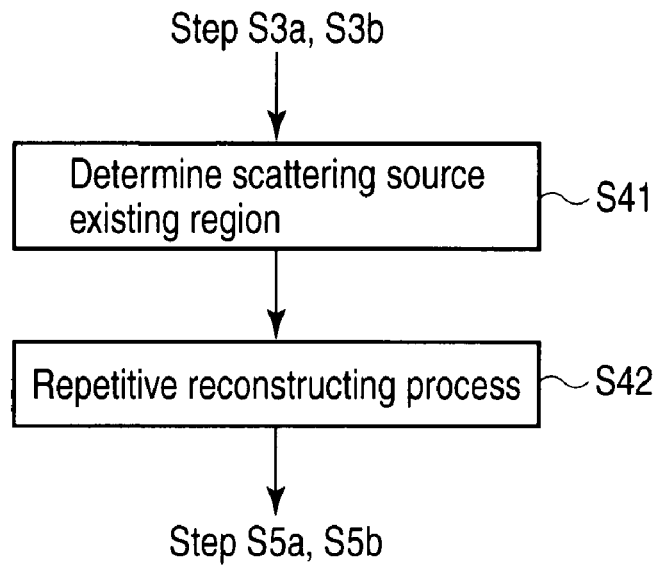
Figure 43:
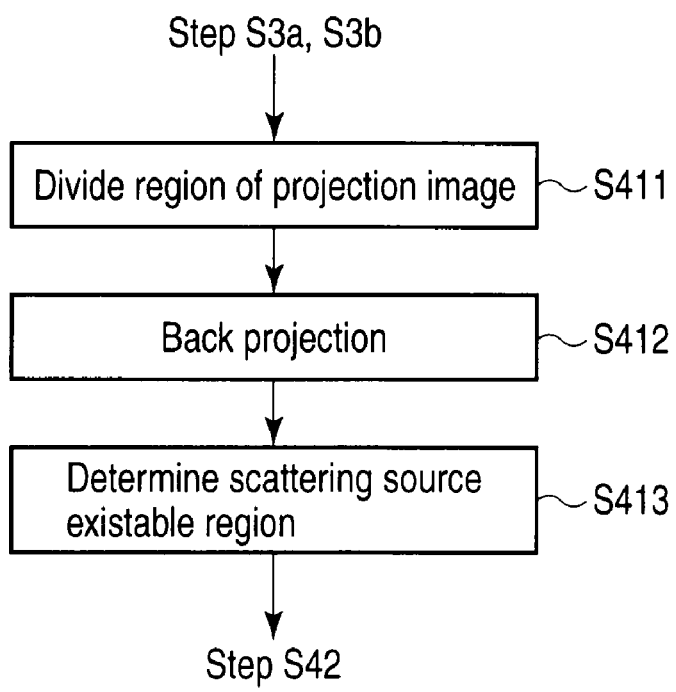
Figure 47:
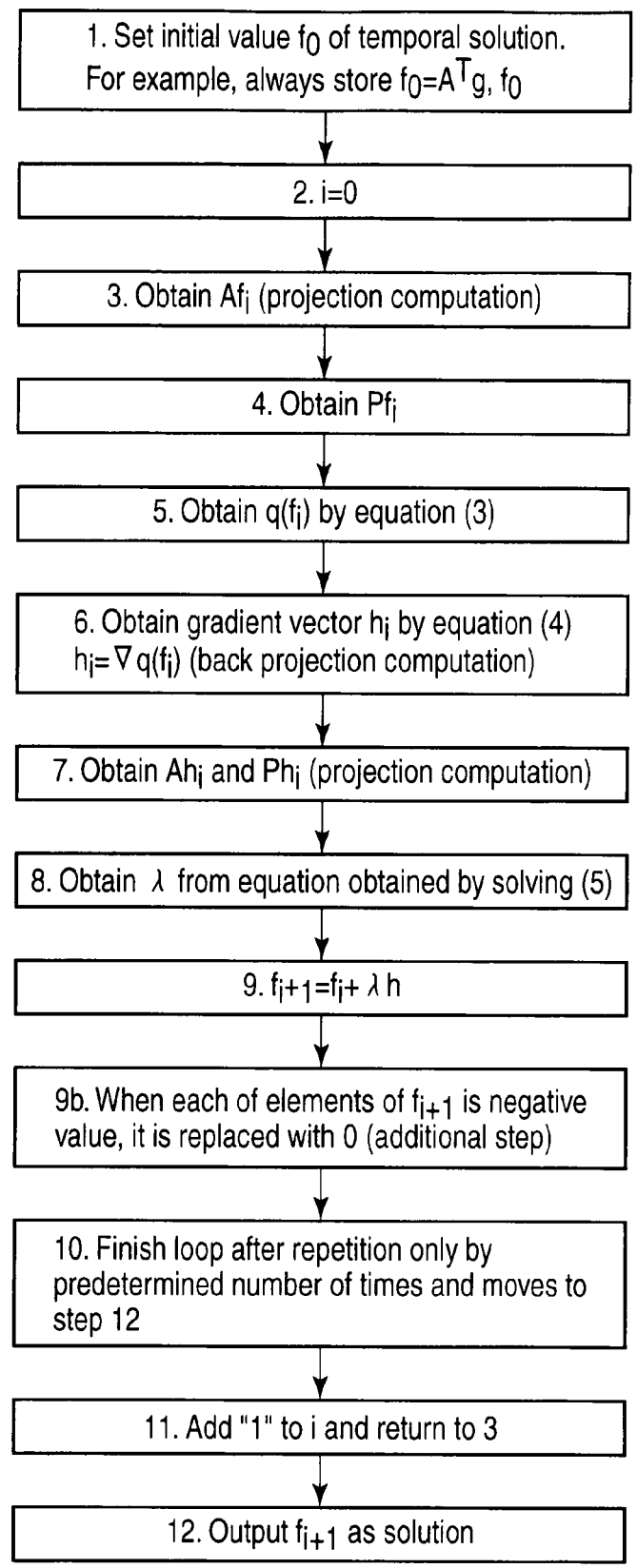
Figure 48:
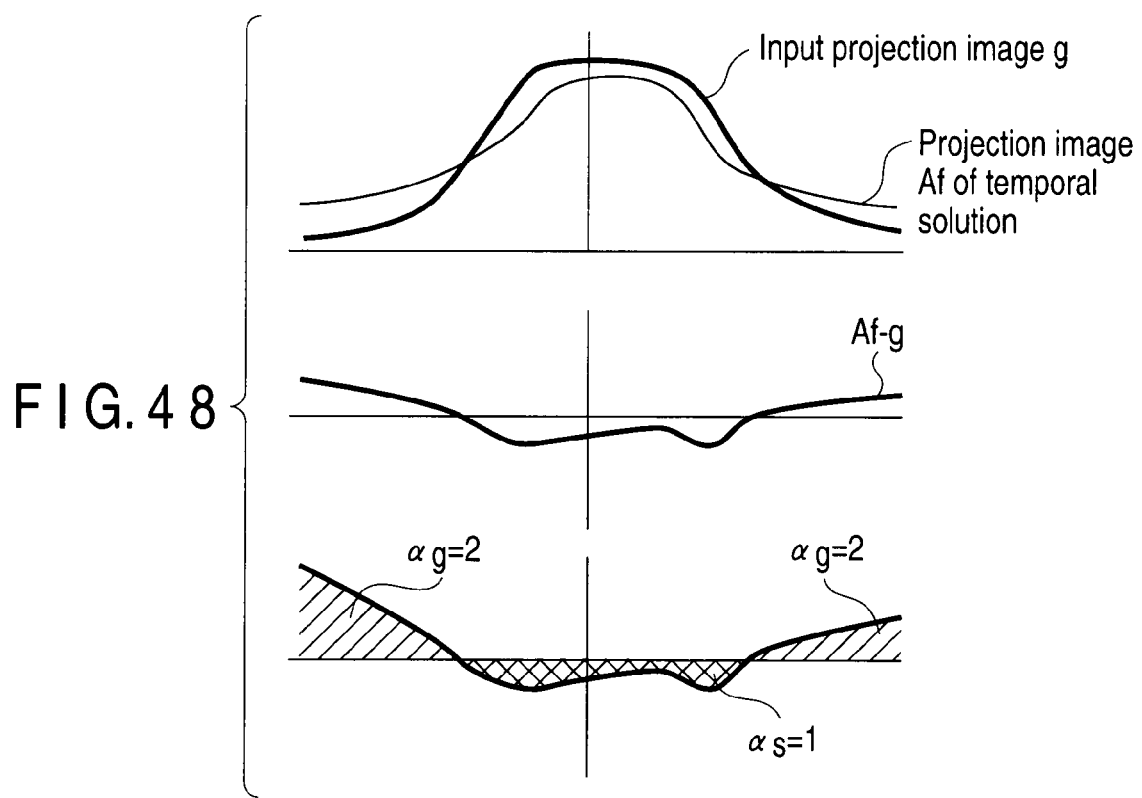
Figure 49:
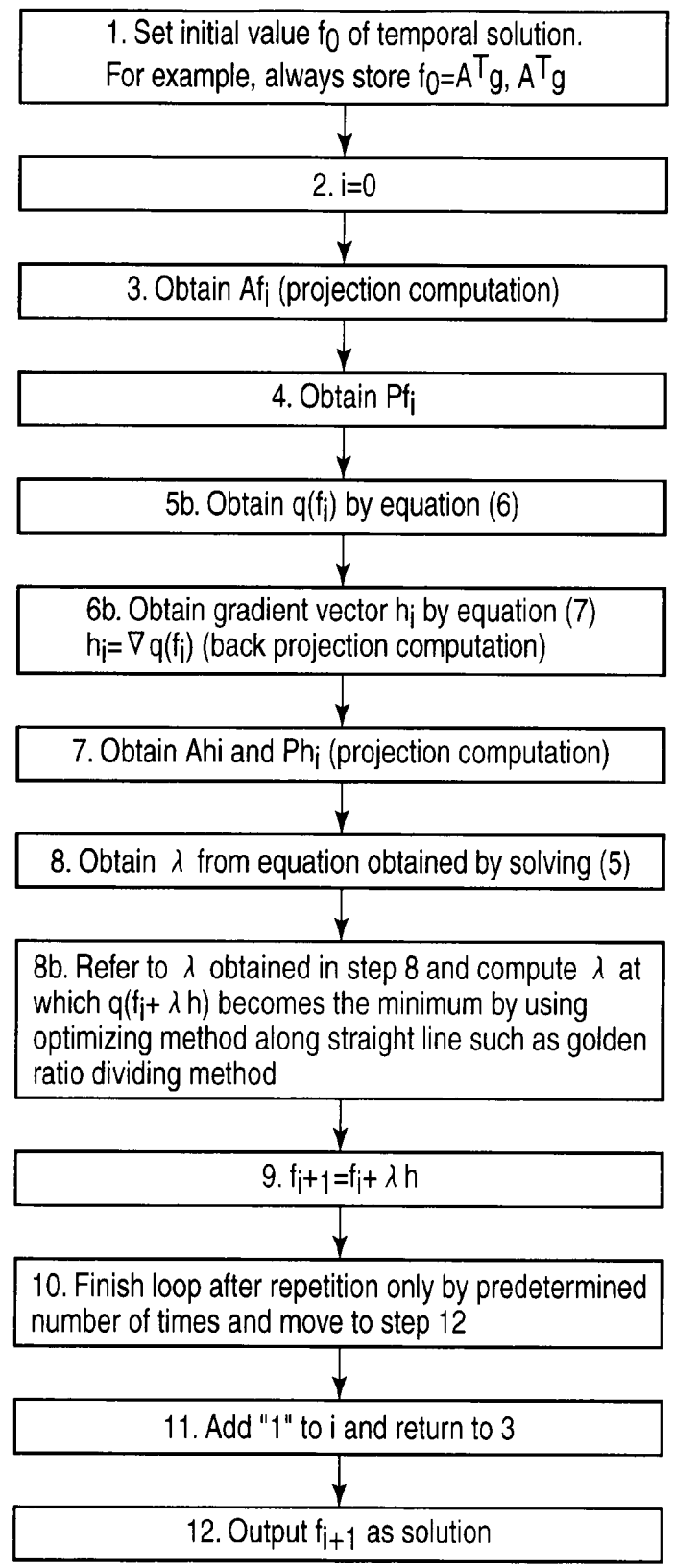
Figure 52:
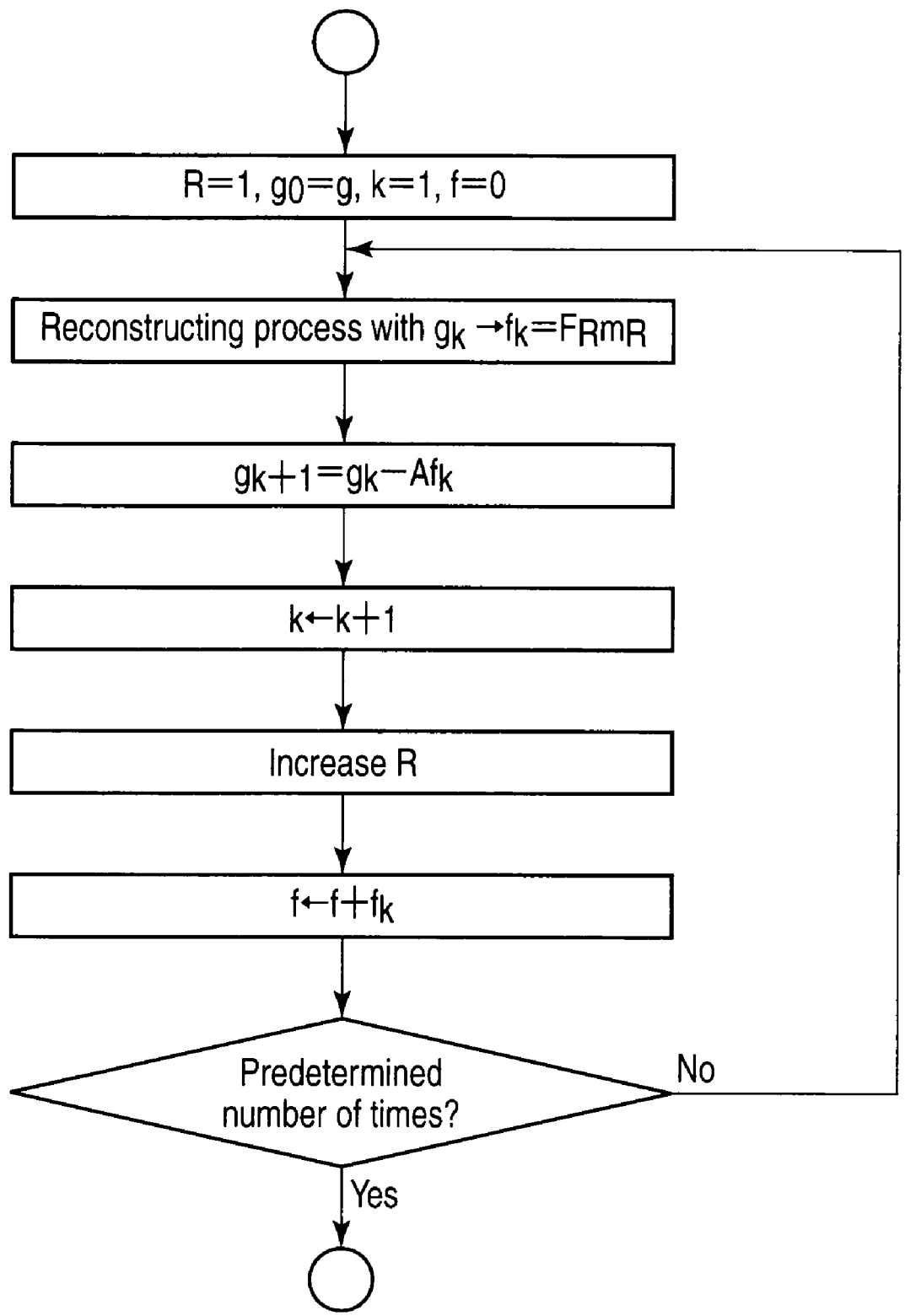

FIG. 16A is a diagram showing a collimator 303 provided at the detection face of the detector 301, and FIG. 16B is a side view of the detector 301 and the collimator 303;

FIG. 17 is a flowchart showing the flow of processes at the time of radiation treatment including the operation of the radiotherapeutic system 1;

FIG. 18 is a diagram showing a mode of display (fusion display) of an absorbed dose image;

FIG. 19 is a block configuration diagram of a radiotherapeutic system;

FIG. 20 is a flowchart showing the flow of processes at the time of radiation treatment including the operation of the radiotherapeutic system;

FIG. 21 is a flowchart showing the flow of processes at the time of radiation treatment including the operation of the radiotherapeutic system;

FIG. 22 is a diagram showing an example of a measurement mode of scattering radiation of the radiotherapeutic system;

FIG. 23 is a diagram showing another example of the measurement mode of scattering radiation of the radiotherapeutic system;

FIG. 24 is a diagram showing concept of tissue density in a voxel;

FIG. 25 is a flowchart showing a converting process procedure;

FIG. 26 is a diagram showing the relation between atomic number and atomic weight;

FIG. 27 is a block configuration diagram of the radiotherapeutic system 1;

FIG. 28 is a flowchart showing the flow of attenuation coefficient distribution estimating process;

FIG. 29 is a flowchart showing the flow of attenuation correcting process;

FIG. 30 is a diagram showing position "x" in a reconstruction space and a direction $n_k$ of the k-th projection;

FIG. 31 is a flowchart showing an example of the flow of conventional reconstructing process in which attenuation correction is not performed;

FIGS. 32A and 32B are diagrams for explaining angle dependency of scattering radiation incident on the detector;

FIG. 33 is a flowchart showing an example of the flow of the image reconstructing process in which attenuation correction is considered;

FIG. 34 is a flowchart showing the flow of the attenuation correcting process and the reconstructing process;

FIGS. 35A and 35B are diagrams for explaining the position of a center axis of radiation pyramid and a scattering radiation source plane passing a straight line orthogonal to both of the center axis of the radiation pyramid and the projection axis of the detector;

FIG. 36 is a diagram for explaining the motion of a rotary image pickup system of the radiotherapeutic system 1;

FIG. 37 is a diagram for explaining the motion of the rotary image pickup system of the radiotherapeutic system 1;

FIG. 38 is a diagram for explaining the motion of the rotary image pickup system of the radiotherapeutic system 1;

FIG. 39 is a diagram for explaining the attenuation correcting process;

FIG. 40 is a block configuration diagram of the radiotherapeutic system 1;

FIGS. 41A and 41B are diagrams for explaining concept of a conditional repetitive reconstructing function;

FIG. 42 is a flowchart showing the flow of processes according to the conditional repetitive reconstructing function;

FIG. 43 is a flowchart showing the flow of a process of determining a scattering radiation source existable region;

FIGS. 44A, 44B, and 44C are diagrams for explaining a process of determining the scattering radiation source existable region;

FIG. 45 is a flowchart showing the flow of a process of determining the scattering radiation source existable region;

FIG. 46 is a flowchart showing a procedure of the steepest descent method;

FIG. 47 is a flowchart showing a procedure of the steepest descent method in which a condition that a solution does not become a negative value is introduced;

FIG. 48 is a diagram showing an example of an input projection image and a projection image of an interim solution in the case where $\alpha_g=2$ and $\alpha_s=1$;

FIG. 49 is a flowchart showing the procedure of the steepest descent method in the case where a condition that an image in which a solution is projected does not exceed a reconstruction input projection image is introduced;

FIGS. 50A, 50B, 50C, and 50D are diagrams for explaining the concept of the reconstructing process;

FIGS. 51A, 51B, 51C, 51D, 51E, and 51F are diagrams for explaining the concept of the reconstructing process; and FIG. 52 is a flowchart showing the flow of the reconstructing process.

DETAILED DESCRIPTION OF THE INVENTION

First to eleventh embodiments of the present invention will be described below with reference to the drawings. In the following description, the same reference numerals are designated to components having almost the same functions and configurations and repetitive description will be given only when required.

First Embodiment

An embodiment of the present invention will be described below with reference to the drawings. In the following description, the same reference numerals are designated to components having almost the same function and configuration, and repetitive description will be given only when required.

[Principle and Method]

A radiotherapeutic system of the first embodiment measures scattering radiation from a subject on the basis of radiation emitted to the subject and, on the basis of the scattering radiation, obtains information objectively showing an irradiated region in the subject and dose of the radiation. The principle and the method are as follows.

Figure 1:
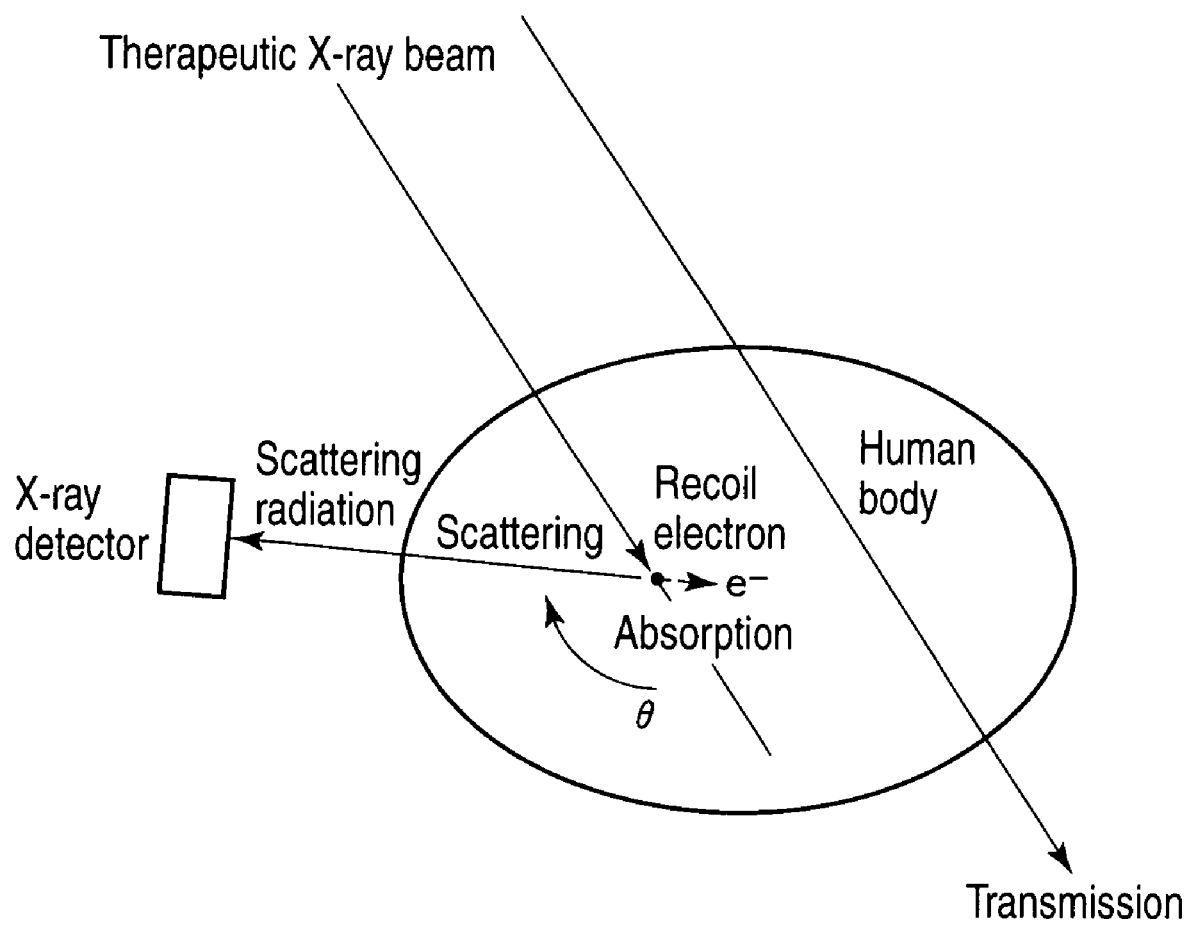
FIG. 1 is a diagram for explaining the principle and method of measuring scattering radiation from a subject based on therapeutic radiation of a radiotherapeutic system.

FIG. 1 is a diagram for explaining the principle and method of measuring scattering radiation from a subject on the basis of therapeutic radiation of the radiotherapeutic system of the invention.

The effect of treatment with the external X-ray radiation is produced mainly by X-ray scattered in the body of a patient. Specifically, when a therapeutic X-ray beam is scattered by electrons in the body of a patient, the electrons which receive the energy fly in tissues and then stop. Until the electrons stop, the electrons generate radicals from molecules in the tissues, and damage DNA in the cells. The cells which are damaged and could not recover finally die. This is the effect of the treatment with the X-ray irradiation. The more recoil electrons are generated, the higher the probability that cells constructing a tissue die becomes. Consequently, the treatment effect is proportional to the number of occurrence times of scattering reaction.

From the above, when the number of times of scattering that occurs in a tissue is known, the treatment effect (how the tissue is damaged) can be known. The number of occurrence times of scattering can be known by measuring the number of scattering radiation. The travel directions of most of X rays scattered are changed by the electrons, and the resultant rays go out from the patient body, so that they can be measured by an X-ray detector mounted on the outside of the patient body.

In the radiotherapeutic system of the embodiment of the present invention, a detector having a collimator is mounted in a position at a specific angle with respect to a therapeutic X-ray beam and selectively detects only scattering radiation in the direction. Since the angle and the degree of an X-ray scattered by Compton scattering are known theoretically, if scattering radiation at a certain angle can be detected, the number of scattering radiation at other angles can be also estimated. Further, to three-dimensionally obtain a distribution of places where scattering occurs in the patient body, the detector is rotated during irradiation and scattering radiation is measured from all of directions (refer to, for example, FIG. 3). After that, a reconstructing process is performed, and a distribution of occurrence of scattering radiation in the subject is three-dimensionally imaged. As the reconstructing method, for example, when the direction of the collimator is orthogonal to the scan axis, a CT reconstructing method is used. On the other hand, when the direction of the collimator is not orthogonal to the scan axis, a tomography reconstructing method is used.

[Configuration]

Figure 2:
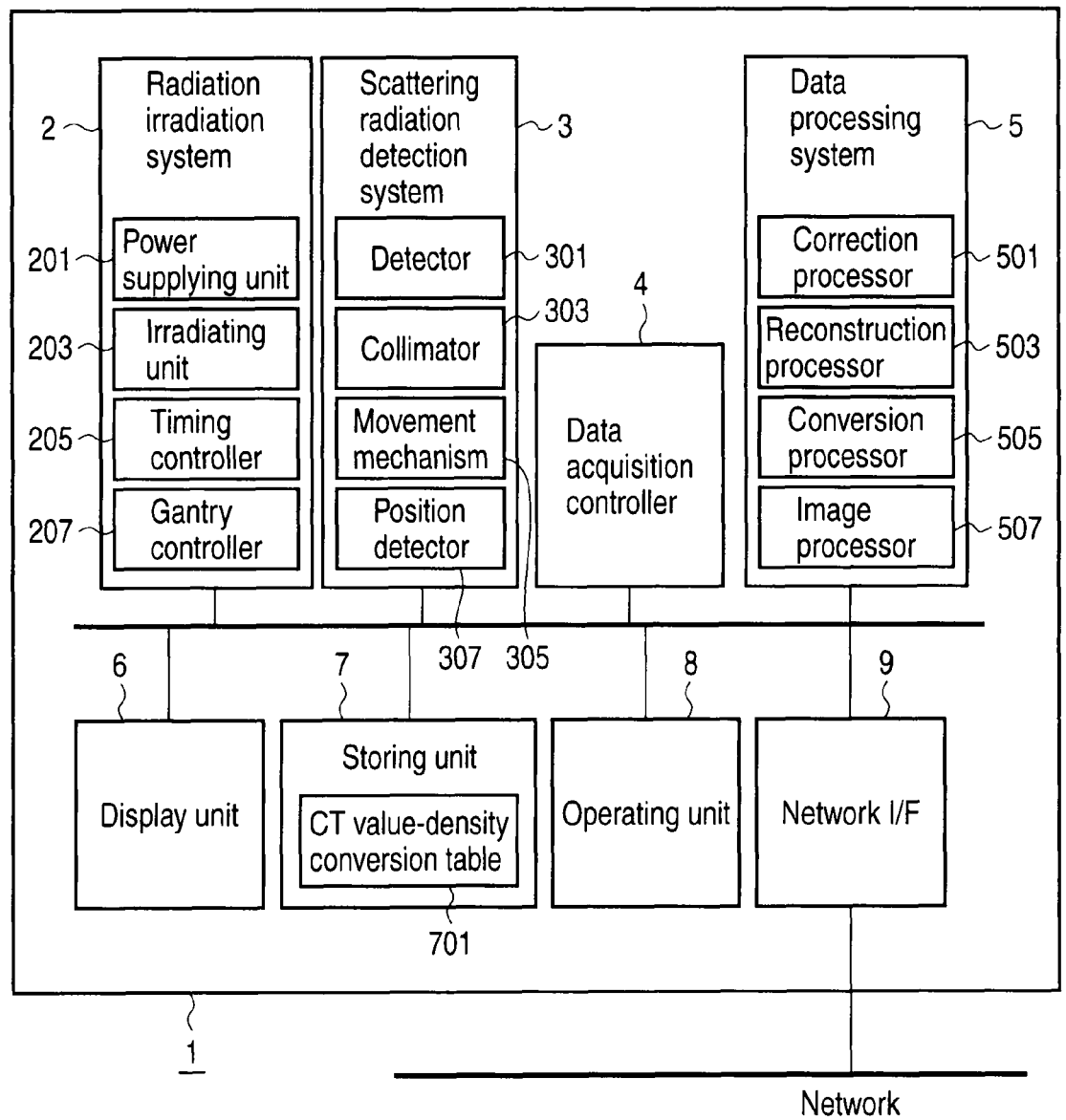
FIG. 2 is a block configuration diagram of a radiotherapeutic system 1 as an embodiment of the present invention.
Figure 3:
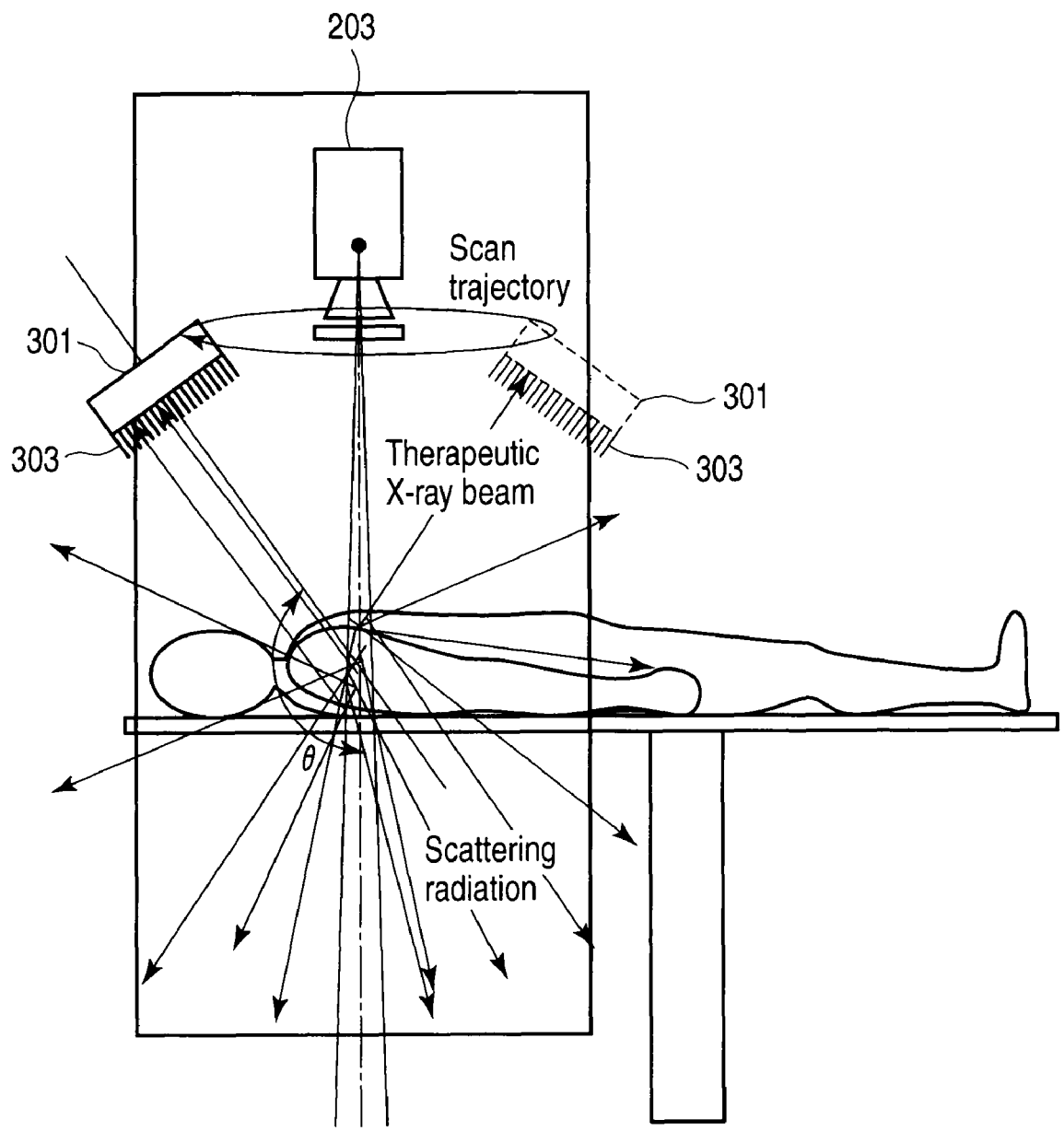
FIG. 3 is a diagram showing a form of measurement of scattering radiation of the radiotherapeutic system 1.

FIG. 2 is a block configuration diagram of a radiotherapeutic system 1 of the embodiment. FIG. 3 is a diagram showing a form of measuring scattering radiation of the radiotherapeutic system 1. As shown in FIG. 2, the radiotherapeutic system 1 has a radiation irradiation system 2, a scattering radiation detection system 3, a data acquisition controller 4, a data processing system 5, a display unit 6, a storing unit 7, an operating unit 8, and a network I/F 9. The radiation irradiation system 2 and the scattering radiation detection system 3 are installed in a gantry. By moving and rotating the gantry, the radiation irradiation system 2 and the scattering radiation detection system 3 can be disposed in arbitrary positions with respect to the subject. The data acquisition controller 4, the data processing system 5, the display unit 6, the storing unit 7, the operating unit 8, and the network I/F 9 are installed, for example, in the body (casing) of the radiotherapeutic system 1.

[Radiation Irradiation System]

The radiation irradiation system 2 has a power supplying unit 201, an irradiating unit 203, a timing controller 205, and a gantry controller 207.

The power supplying unit 201 supplies power to the irradiating unit 203 under control of the data acquisition controller 4.

The irradiating unit 203 is a radiation irradiating apparatus having the configuration of, for example, a linear accelerator (linac) or the like. In the irradiating unit 203, thermal electrons emitted from a cathode are accelerated to a few hundreds keV by an electron gun disposed at one end of an accelerating tube. Next, microwaves generated from a klystron are guided to the accelerating tube by using a waveguide. In the accelerating tube, the thermal electrons are accelerated to an energy of a few MeV. The direction of the accelerated thermal electrons is changed by a magnet, and the thermal electrons collide with a transmission target. By breaking radiation, X-ray of energy of a few MeV is generated. The irradiating unit 203 shapes the X-ray to a predetermined shape (for example, a conical shape) by a collimator, and emits the resultant ray to a three-dimensional region in the subject laid on the bed.

The timing controller 205 controls the power supplying unit 201 so that power is supplied to the irradiating unit 203 at a predetermined timing under control of the data acquisition controller 4.

The gantry controller 207 controls, for example, the movement position and the rotation position of the gantry in accordance with the control instruction from the operating unit 8 and the data acquisition controller 4.

[Scattering Radiation Detection System]

The scattering radiation detection system 3 has a detector 301, a collimator 303, a movement mechanism 305, and a position detector 307.

The detector 301 is a semiconductor detector capable of detecting an X-ray of a few hundreds keV, an imaging plate, or the like, and detects scattering radiation from a subject based on radiation emitted to the subject at positions where penetrating radiation from the subject are not passed. The preferred size of the detector, the disposition angle with respect to the radiation beam axis, the number of pixels, and the like will be described later.

The collimator 303 is a narrowing device for selectively detecting only scattering radiation in a specified direction. A preferred shape, grid size, and the like of the collimator 303 will be described later.

The movement mechanism 305 is a movement mechanism for moving the position and the angle of the detector 301 to control the angle of the detection surface of the detector 301 to the irradiation beam axis of the irradiating unit 203 (that is, the angle between the irradiation beam axis and the normal line to the detection surface of the detector 301), the rotation angle of the detector 301 using the radiation beam axis as a center, the distance between the subject and the detection surface of the detector 301, and the like.

The position detector 307 is an encoder for detecting the position of the detector 301.

<Size of Detector 301>

Figure 4:
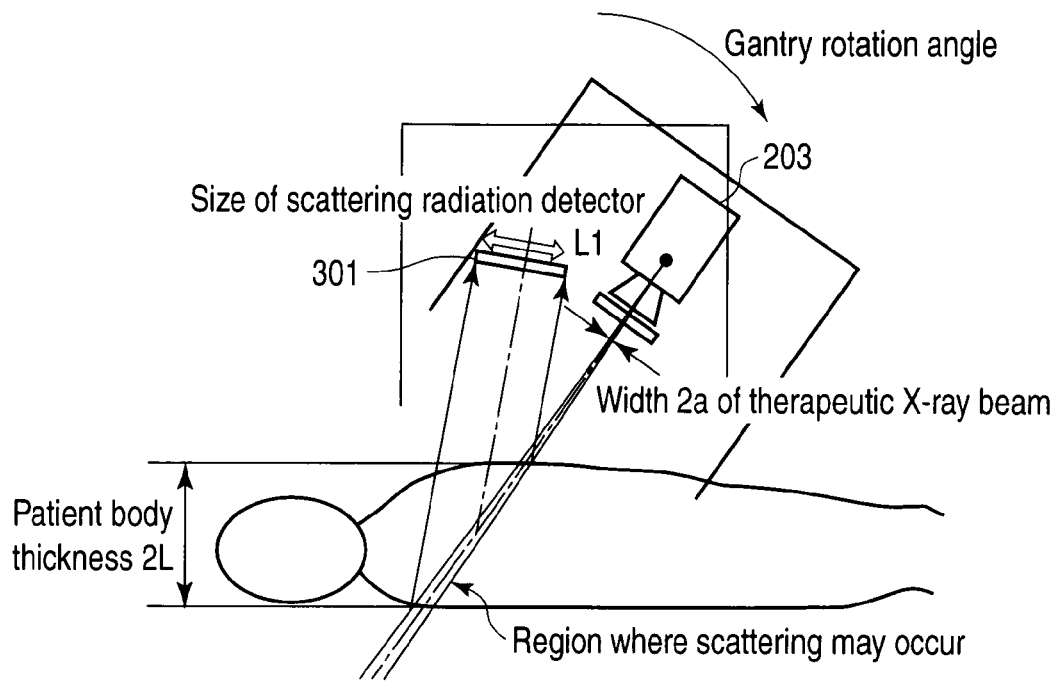
FIG. 4 is a diagram for explaining the size of a detector 301.
Figure 5:
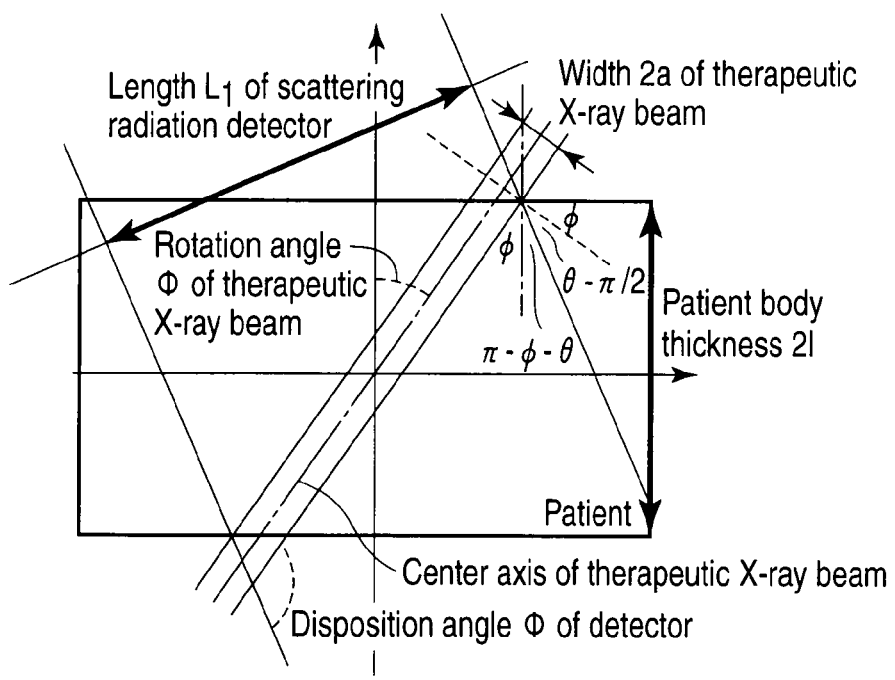
FIG. 5 is a diagram for explaining the size of the detector 301.
Figure 6:
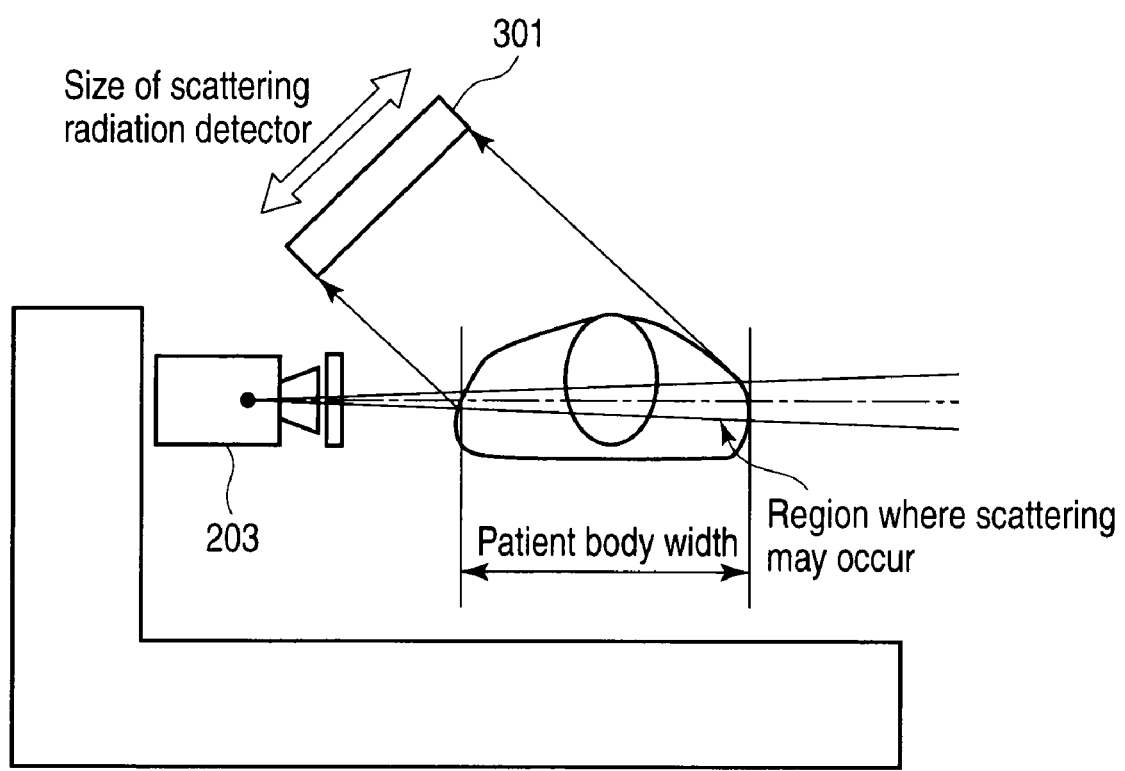
FIG. 6 is a diagram for explaining the size of the detector 301.

FIGS. 4, 5, 6, 7, and 8 are diagrams for explaining the size of the detector 301. The size of the detector 301 is preferably a size covering the range of scattering radiation from the inside of the body of the patient. The size is determined by, as shown in FIGS. 4 and 5, width $2a$ of a treatment beam, rotation angle φ (rotation angle of the gantry of the irradiation system), the disposition angle θ of the detector 301, and thickness (width) $2L$ of the body of the patient. Using the values, length $L_1$ of (the detection face) of the detector 301 can be expressed by the following equation (1).

$$L_1 = 2 \cdot \left( \frac{l}{\cos\phi} + a\tan\left(\left|\theta - \frac{\pi}{2}\right|\right) + a\tan\phi \right) \cdot \sin(\pi - \theta) \quad (1)$$

It is assumed that the treatment X-ray beam is parallel beams and the detector 301 rotates around the center of the thickness of the patient as a center. When the width of the treatment beam is 4 cm, the rotation angle is 35°, the disposition angle of the detector 301 is 120° (or 60°), and the thickness of the body of the patient is 30 cm, $L_1$=36.1 cm. The value depends mainly on the disposition angle of the detector 301. For example, when the detector 301 is disposed in the position of 155° (or 25°), $L_1$=20.3. The configuration can become more compact with distance from 90°.

When the width of the body of the patient is 2w, the length $L_1$ of the detector 301 can be expressed by the following equation (2).

$$L_1 = 2 \cdot \left( w + a\tan\left(\left|\theta - \frac{\pi}{2}\right|\right) \right) \cdot \sin(\pi - \theta) \quad (2)$$

It is also assumed that the treatment X-ray beam is parallel beams. When the width of the treatment beam is 4 cm, the disposition angle of the detector 301 is 120° (or 60°), and the width of the body of the patient is 40 cm, $L_2$=36.6 cm (=20.5 cm at 25°).

Figure 7:
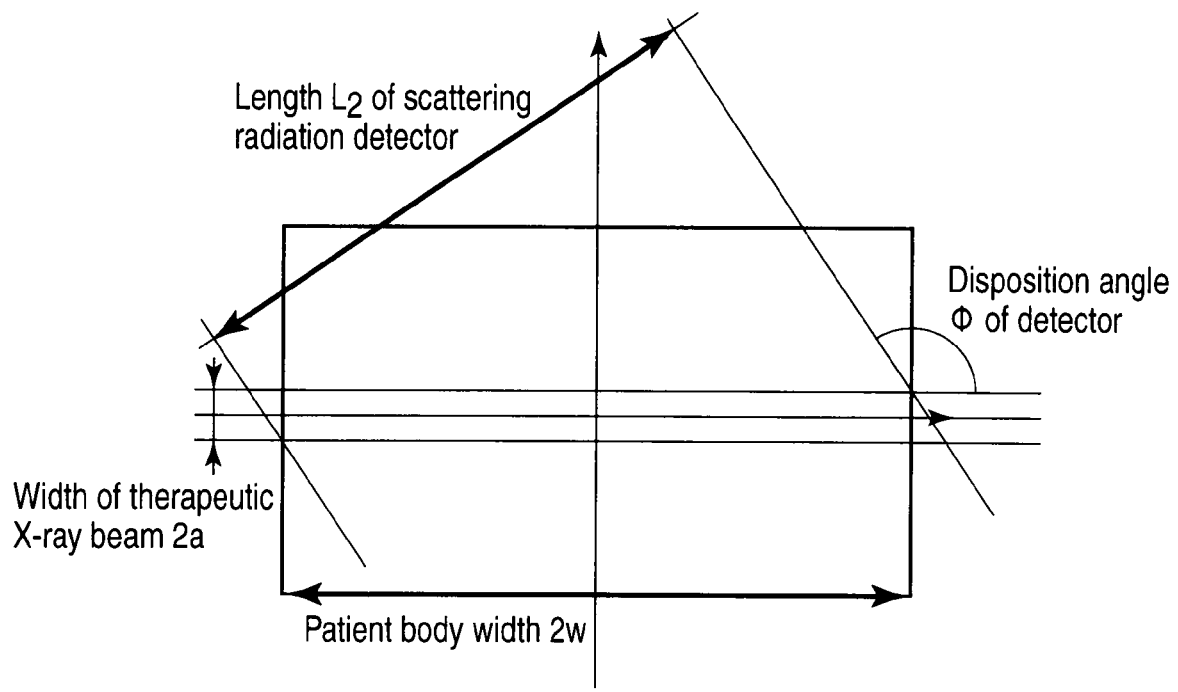
FIG. 7 is a diagram for explaining the size of the detector 301.

In practice, there is the case where the irradiation system is tilted simultaneously in both directions. For example, when the irradiation system is tilted simultaneously at angles as shown in FIGS. 4 and 7, in the position of 120°, the length becomes about 57 cm (about 31 cm at 155°). The actual size $L_1$ of the detector 301 has to be determined according to a tilt angle of the irradiation system.

Figure 8:
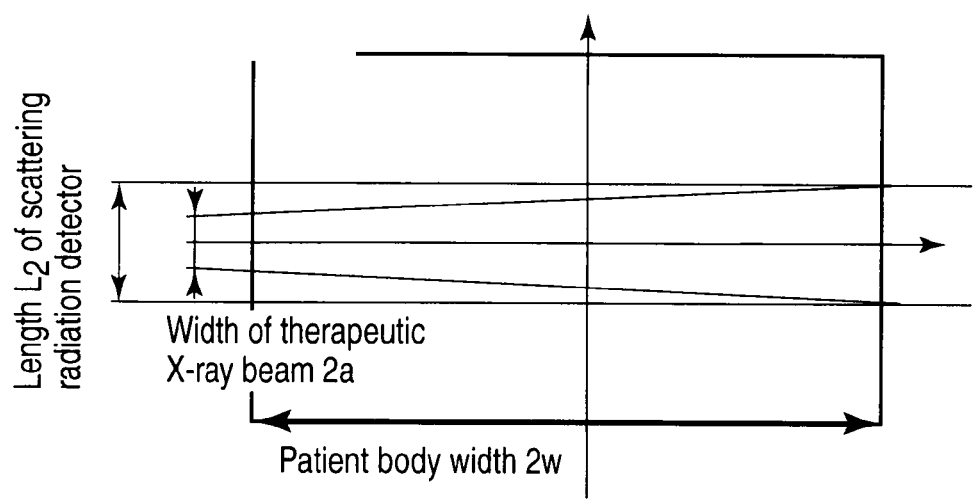
FIG. 8 is a diagram for explaining the size of the detector 301.

Another size $L_2$ of the detector 301 is determined by the width of the treatment X-ray beam as shown in FIG. 8. In the case where it is assumed that there is no broadening of the treatment X-ray beam, 2a is sufficient. However, since the treatment X-ray beam broadens in practice, the size larger than 2a is necessary. It is known that the beam width in a treatment X-ray beam collimator usually becomes about three times around the center of the patient. Consequently, when the beam width in the collimator is set as a reference, the size has to be set at least three times as large as the beam width and is about four times in reality. When the target size is regarded as a reference, since the target size in a treatment aiming at complete cure is about 3 cm, a size of about 4 cm is necessary. In irradiation aiming at symptom relief, a wide range of about 10 cm is irradiated, so that a size of about 13.3 cm is necessary.

As described above, the size of the detector 301 capable of detecting all of scattering radiations on assumption that the disposing angle of the detector 301, the width of the treatment beam (size of the target and the irradiation range), rotation angle, and the size of the body of the patient is determined. In a system which cannot realize the size due to interference with the irradiation system or the patient, scattering radiation data only in a range which can be covered is reconstructed.

<Disposition Angle of Detector 301>

In determination of the size of the above-described detector 301, the size of the detector which can cover the region in which scatter occurs largely changes according to the disposition angle. On the other hand, tendency of occurrence of scatter also varies according to the angle. The number of counting scattering radiations which can be detected varies according to the disposition angle. It is known that the tendency of occurrence of scatter at each angle (angle differential scattering cross section) is expressed by Klein-Nishina formula as shown by the following equation (3).

$$\frac{d\sigma_e}{d\Omega} = \frac{r_0^2}{2}(2 - \sin^2\theta)F_{KN} = \frac{r_0^2}{2}(1 + \cos^2\theta)F_{KN} \quad (3)$$

$$F_{KN} = \left\{ \frac{1}{1 + \alpha(1 - \cos\theta)} \right\}^2 * \left[ 1 + \frac{\alpha^2(1 - \cos\theta)^2}{\{1 + \alpha(1 - \cos\theta)\}} \right. \\ \left. (1 + \cos^2\theta) \right]$$

where $\alpha$ denotes the ratio between X-ray incidence energy and electron rest energy, $r_0$ denotes classical radius and is $2.82 \times 10^{-15}$ [m], and $\theta$ denotes an X-ray scattering angle.

FIG. 9 is a graph in which the Klein-Nishina formula is calculated every 5°. The incidence energy is 5 MeV which is almost the same as that of the treatment X-ray beam used in normal X-ray external radiation. The unit of the angle is degrees, and the unit of sectional area is b (10E-24 *m$^2$). As understood from the graph, forward scattering whose travel direction can be changed only little by scattering is dominant. Consequently, to increase the number of counts and improve the S/N ratio, it is advantageous to detect scattering radiation in a position at a shallow angle with respect to the treatment beam X-ray (incident X-ray). Finally, on the basis of the measurement value at the angle $\theta$ of disposing the detector, using the values shown in FIG. 9 (the values calculated by the Klein-Nishina formula), a process of estimating the number of X rays scattered at other angles is required. Therefore, the S/N ratio exerts an influence on the result.

Figure 10A:
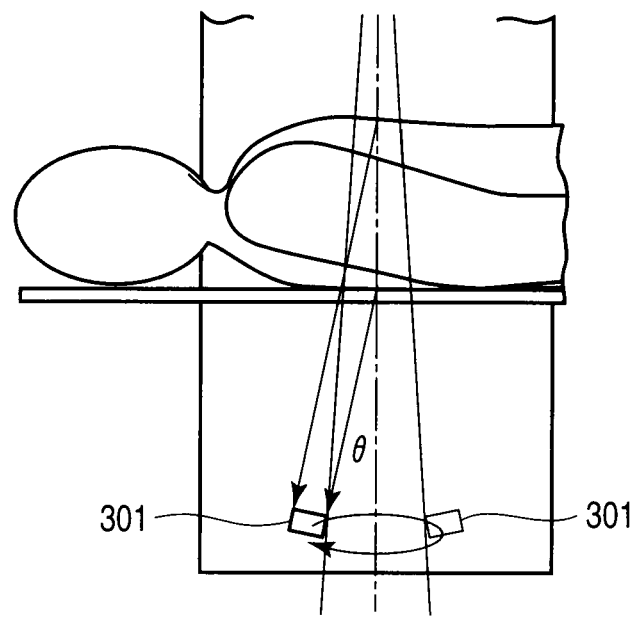
FIGS. 10A and 10B are diagrams showing examples of disposition angles of the detector.
Figure 10B:
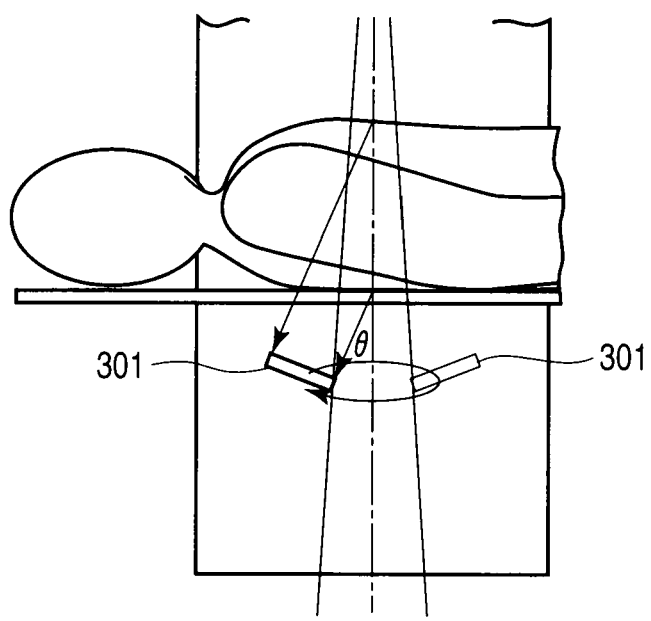

At 0 degree at which the number of scattering times is the largest (that is, the travel direction is unchanged also after scattering with electrons), a correcting process for distinguishing the scattering radiation from the penetrating radiation which has not scattered in the body of the patient is necessary. However, for example, at the disposition angles as shown in FIGS. 10A and 10B, the correcting process is unnecessary. That is, FIG. 10A shows arrangement of angles at which, by setting $\theta$ as small as possible, the large number of counts is obtained, and the correcting process for distinguishing the penetrating radiation and the scattering radiation from each other is unnecessary. The number of counts also depends on the distance between the patient and the detector. The shorter the distance, the more it is advantageous. In FIG. 10B, $\theta$ is slightly larger, but the distance can be set shorter than that of FIG. 10A. However, in the case where the disposition angle of the detector is smaller than 90° (that is, in the case of forward scattering), the scattering radiation passes through the bed and enters the detector. When it is assumed that the material of the bed is carbon fiber (density 1.9 g/cm$^3$) and the thickness is 2 cm, about 10% of scattering radiation is scattered during the passage in the bed, and the travel direction changes. Consequently, there is a drawback such that an additional process of collecting data of scattering in the bed in advance and correcting acquired data with the collected data is required in order to collect accurate scattering radiation data.

In the above, the disposition example of the detector based on the idea of placing importance on the number of counts has been described. However, to accurately estimate the effect of treatment, it is preferable to accurately measure scattering radiation making a larger contribution to treatment among scattering in all of directions. To accurately count the scattering radiation, preferably, $\theta$ is set to be large. As described in "Principle and Method", the effect of treatment with X-ray irradiation is produced mainly by electrons which receive energy from X-rays at the time of scattering. The angle of the X ray which gives a larger amount of energy to the electrons is largely changed, so that the scattering angle becomes large.

FIG. 11 is a diagram showing a state of Compton scattering. Energy hv' of scattering radiation and electrons and Te after scattering are expressed by the following equation (4) using incidence energy hv of X-ray and scattering angle θ.

$$hv' = \frac{hv}{1+\alpha(1-\cos\theta)} T_e = hv - hv' \text{ here, } \alpha = \frac{hv}{mc^2} \quad (4)$$

FIG. 12 is a graph showing the relation between energy of photon after the Compton scattering and the scattering angle θ. As shown in the diagram, scattering radiation having a large scattering angle does not occur easily and the number of counts is small. However, the electron has much energy. It is therefore understood that the X-ray contributes largely to treatment. When the scattering angle θ satisfies the relation 85°<θ<180°, 90% or more of the energy of an incident therapeutic X-ray beam is give to the electrons and finally give to an organic tissue. To accurately measure the scattering radiation making a large contribution to treatment, the disposition angle of the detector as described above is desirable.

Figure 13:
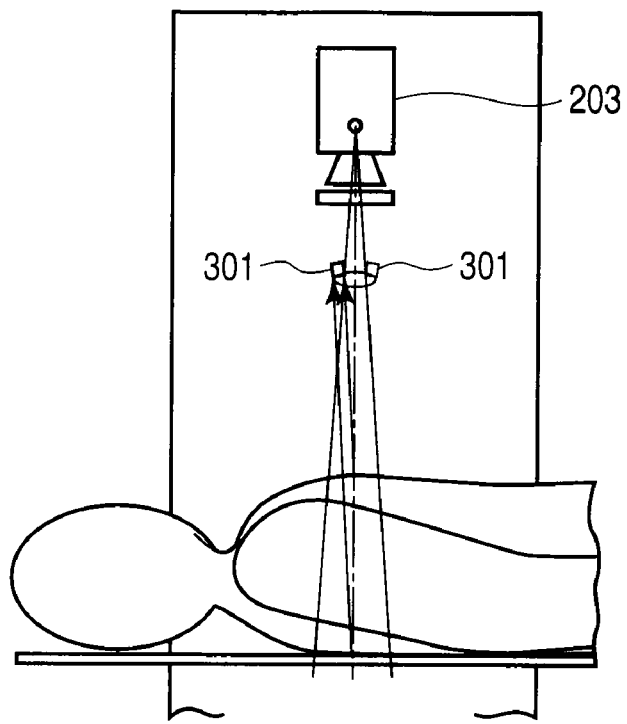
FIG. 13 is a diagram showing an example of disposition of the detector for detecting scattering radiation more accurately.

FIG. 13 is a diagram showing an example of disposition of the detector for detecting scattering radiation making a large contribution to treatment more accurately. The disposition does not require the scattering correcting process using the bed and also has an advantage that the size of the detector may be small.

An error may occur also depending on the disposition precision of the detector. It is impossible to dispose the detector in an intended position without an error when a mechanical deflection or the like is considered (it is also extremely difficult to measure a deviation of the detector due to a mechanical deflection or the like). As shown in FIG. 9, the magnitude of an angle change of the scattering cross section varies according to the angle. In the case of disposing the detector at the angle at which the angle change magnitude is large, an error becomes large.

Figure 14:
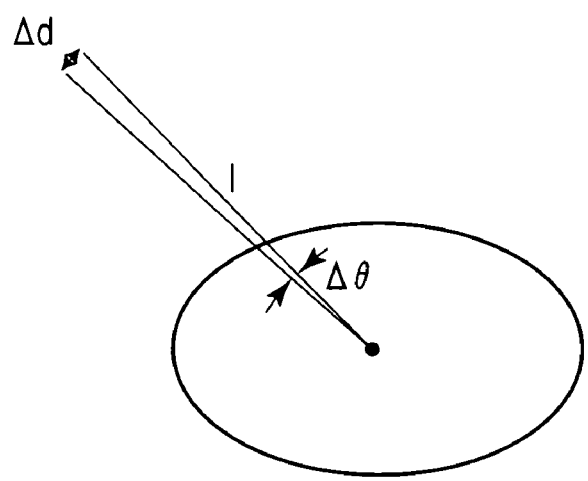
FIG. 14 is a diagram for explaining the corresponding relation between a deviation Δd of the position of disposing the detector and a deviation Δθ of the scattering angle.

FIG. 14 is a diagram for explaining the corresponding relation between a deviation Δd of the disposing position of the detector and a deviation Δθ of the scattering angle. In FIG. 14, the deviation Δθ of the scattering angle caused by the deviation Δd of the disposing position of the detector is expressed by the following equation (5) when the distance between the place where scattering occurs and the detector is l.

$$\Delta d = l \cdot \Delta\theta \cdot \frac{180}{\pi} \quad (5)$$

For example, when l is 500 mm, if Δd is 1 mm, Δθ is about 0.1°. An error of the number of counts which occurs accordingly is about 0.6% which is the largest at the scattering angle of around 18°. As the scattering angle increases, the error decreases monotonously, and becomes equal to or less than 0.0001% at the scattering angle of 180°. In actual disposition of the detector, considering avoidance of interference with the therapeutic X-ray beam, it is difficult to dispose the detector at 180° but, preferably, the detector is disposed, for example, in the range of 140°≦θ<180° in which an error is 0.05% or less.

Figure 15:
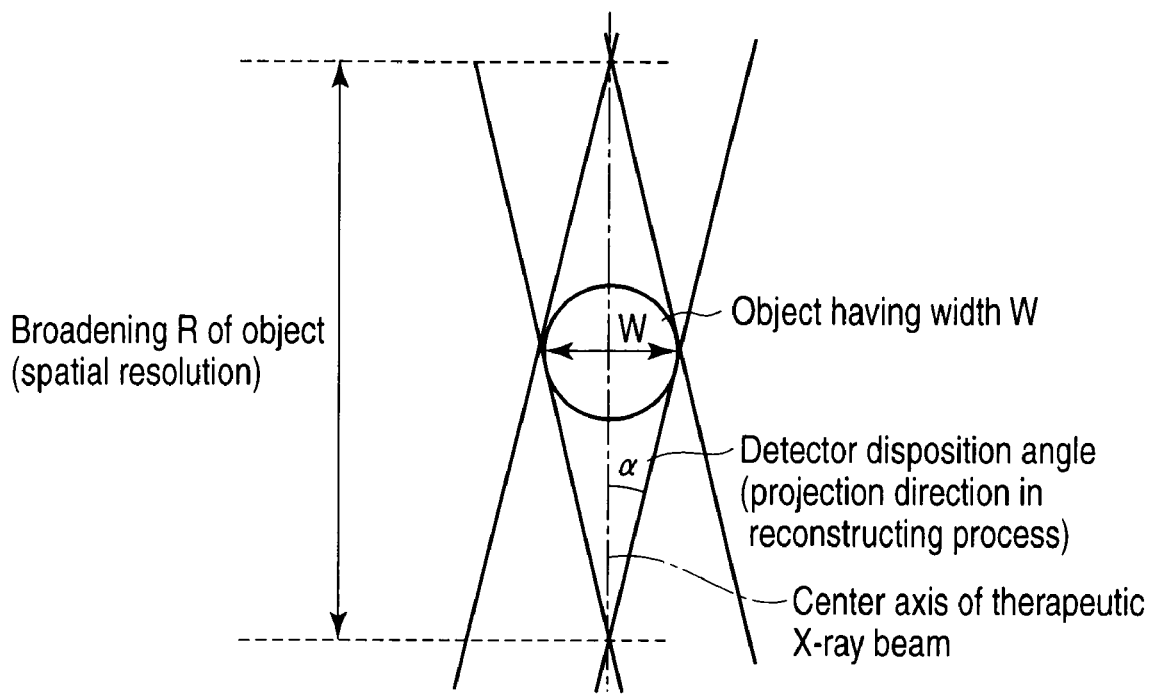
FIG. 15 is a diagram for explaining the disposition angle of the detector, the size of an object, and spatial broadening of the object reconstructed.

The disposition angle of the detector also exerts an influence on the space resolution of an image reconstructed. FIG. 15 shows the relations among the width of an object to be reconstructed, detector disposition angle (that is, the projection direction in the reconstruction process), and broadening R of the object reconstructed. It is understood from FIG. 15 that the magnitude of R can be expressed by the following equation.

$$R = \frac{W}{\tan\alpha} = \frac{W}{\tan(\pi-\theta)} \text{here, } \theta \text{ is a scattering angle} \quad (6)$$

It is understood from the equation (6) that when the detector is disposed at 90°, the space resolution can be minimized. With distance from 90°, the space resolution becomes higher. Around the angle 90°, the detector interferes with the patient and the bed, so that it is extremely difficult to realize it. However, it is desirable to dispose the detector at an angle close to 90° as much as possible.

From the viewpoints of the contribution to treatment, an error occurring in the number of counts, and the spatial resolution after reconstruction, the disposition angle θ of the detector is desirably a value which is as small as possible in the range of 140°≦θ<180°.

<The Number of Detectors>

In the embodiment, by rotating the detector 301 around the axis of the emitted radiation beam while maintaining the detection face at a predetermined angle with respect to the beam axis (or by scanning the subject with scattering radiation), scattering radiation data in a plurality of positions (that is, data in multiple directions at the same scattering angle) is obtained. However, the invention is not limited to the embodiment. To obtain data in multiple directions at the same scattering angle, a plurality of detectors disposed at different rotation angles (that is, in a plurality of positions on a circumference around the beam axis as a center) may be used so as to detect scattering radiation rays having the same scattering angle. It is also possible to rotate the plurality of detectors disposed at different rotation angles around the axis of the radiation beam as a center and obtain data in multiple directions at the same scattering angle. By using a plurality of detectors as described above, there are advantages that the number of counts increases and the S/N ratio improves.

<Shape of Collimator>

FIG. 16A is a diagram showing the collimator 303 provided for the detection face of the detector 301. FIG. 16B is a side view of the detector 301 and the collimator 303. As shown in FIGS. 16A and 16B, the detector 301 has the grid-shaped collimator 303 so that only scattering radiation in the disposition angle direction can be detected (that is, only scattering radiation at the scattering angle θ can be detected).

<Grid Size of Collimator>

The grid size determines the resolution of a three-dimensional distribution reconstructed as it is. The smaller the grid size is, the more the space resolution improves. However, the number of counting the scattering radiation rays decreases, so that the S/N ratio deteriorates.

In the case of normal complete care, a target is irradiated with a dose obtained by dividing a total dose of about 60 to 70 Gy by about 30 days. That is, the irradiation dose to a target per day is about 2 Gy. The number of photons of a therapeutic X-ray beam necessary for irradiation of 2 Gy can be calculated by the following equation (7) (source: "Evaluation of an Absorbed Dose to the Human Body By Measuring Ionizations in a Cavity Chamber", Fujio Araki) and is $1.3\times10^{11}$ photons/cm² on assumption that the energy E of the therapeutic X-ray is 5 MeV, the target is water, and μen/ρ is 0.0191.

$$\Phi = \frac{10D \times 10^{-6}}{E 1.6 \times 10^{-19}(\mu_{en}/\rho)} = \frac{D \times 10^{14}}{1.6 \times E(\mu_{en}/\rho)} \quad (7)$$

Therefore, the number of scattering radiation rays per 1 cm³ can be calculated as the following equation (8).

$$\Phi \times \left(1 - e^{-\frac{\mu_{en}}{\rho}}\right) = 3.9 \times 10^9 \quad (8)$$

For example, when the grid size is 1 cm and the detector is mounted in a place apart from the target by 50 cm, the number $N_{1cm2}$ of counts per grid is expressed by the following equation (9).

$$N_{1cm2} = \frac{3.9 \times 10^9}{4\pi \cdot 50^2} = 1.24 \times 10^5 [\text{counts/cm}^2] \quad (9)$$

The number of counts is an average value of the case where dependency on angle of scattering is ignored, and is a value smaller by about two digits in a position where the scattering angle is large. In the case of fluoroscopy for diagnosis (10 mR), the number of counts is about $2.4 \times 10^5$ [counts/cm²]. However, the spatial resolution of fluoroscopy is about 0.2 mm which is high. If the spatial resolution is 1 cm, the number of counts of 1/2,500 (up to about $10^2$) is sufficient. However, even in the case of disposing the detector in a position where the scattering angle is large, the number of counts of about $10^3$ which is larger than that of fluoroscopy by one digit can be obtained.

The grid size has to be an integral multiple of the pixel size of the detector or a fraction of an integer. The pixel size of the detector is desirably smaller than the grid size so that a loss does not occur in the number of counts. For example, when the grid size is 1 cm, the detector pixel size may be 1 cm, 0.5 cm, 0.2 cm, 0.1 cm, or the like.

[Data Acquisition Controller]

The data acquisition controller 4 performs total control on the scattering radiation measurement at the time of radiation treatment. For example, the data acquisition controller 4 statically or dynamically controls the radiotherapeutic system 1 on radiation irradiation, scattering radiation measurement, data process, image display, network communication and the like by obtaining a signal from the timing controller 205 of the radiation irradiation system 2 and transmitting a scattering radiation measurement start trigger and a detection data transmission trigger to the scattering radiation detection system 3. As necessary, the data acquisition controller 4 optimizes scan time in accordance with irradiation time on the basis of a treatment plan received from a radiation treatment planning apparatus via a network.

[Data Processing System]

The data processing system 5 has a correction processor 501, a reconstruction processor 503, a conversion processor 505, and an image processor 507.

The correction processor 501 performs a data calibration process, a correcting process for eliminating noise, and the like as necessary. The correcting process executed by the correction processor 501 will be described in detail later.

The reconstruction processor 503 executes an image reconstructing process using scattering radiation image data detected by the scattering radiation detection system 3 and position information indicative of a position in which the scattering radiation image data is detected to obtain scattering radiation source volume data indicative of a three-dimensional distribution of density of the number of scattering events (the number of scattering occurrence times). As the reconstructing method, for example, when the direction of the collimator is orthogonal to the scan axis, a CT reconstructing method is used. On the other hand, when the direction of the collimator is not orthogonal to the scan axis, a digital tomosynthesis technology is used.

The conversion processor 505 converts three-dimensional image data obtained by the image reconstructing process to absorbed dose volume data indicative of a three-dimensional distribution of absorbed radiation dose (absorbed dose).

The image processor 507 generates absorbed dose image data indicative of a distribution of radiation dose (absorbed dose) absorbed in a predetermined region in the subject by using the absorbed dose volume data or the like. In the case of displaying an absorbed dose image by fusion imaging, the image processor 507 performs an image synthesizing process using the absorbed dose volume data and the like.

[Display Unit, Storing Unit, Operating Unit, and Network I/F]

The display unit 6 displays an absorbed dose image in a predetermined form by using the absorbed dose image data. For example, the display unit 6 fuses the absorbed dose image with a plan image and images obtained just before irradiation and during the irradiation, and displays the resultant image, as necessary.

The storing unit 7 stores scattering radiation volume data, absorbed dose volume data, and absorbed dose image data obtained by a predetermined scan sequence for acquiring (scanning) scattering radiation data while rotating the detector 301 using the axis of a radiation beam emitted as a center, a control program for executing the correcting process, the image reconstructing process, the converting process, the display process, and the like, a dedicated program for displaying and editing a treatment plan in the system, and the radiotherapeutic system 1, image data obtained by other modalities such as an X-ray computerized tomography apparatus, and the like. The data stored in the storing unit 7 can be also transferred to an external apparatus via a network I/F 90.

The operating unit 8 has various switches, buttons, a track ball 13s, a mouse 13c, a keyboard 13d, and the like for taking various instructions, conditions, region-of-interest (ROI) setting instructions, various image quality parameter setting instructions, and the like from the operator to an apparatus body 11.

The network I/F 9 transfers the absorbed dose image data or the like obtained by the radiotherapeutic system 1 to another apparatus via a network or obtains, for example, a treatment plan or the like generated by a radiation treatment planning apparatus via a network.

(Operation)

Next, the operation in radiation treatment of the radiotherapeutic system 1 will be described.

FIG. 17 is a flowchart showing the flow of processes in radiation treatment including the operation of the radiotherapeutic system 1. The processes in the steps will be described below.

[Disposition of Subject and the Like in Step S1]

First, the data acquisition controller 4 acquires treatment plan information on the subject via, for example, a network and displays it on the display unit 6. The operator disposes the subject on the bed in accordance with the displayed treatment plan and performs setting of radiation irradiation time, setting of rotation angle accompanying measurement of scattering radiation, selection of a scan sequence, and the like via the operating unit 8 (step S1). The radiation irradiation time and the like may be automatically set on the basis of the obtained treatment plan information.

[Radiation irradiation and Acquisition of Scattering Radiation Image Data in Multiple Directions in Step S2]

The radiation irradiation system 2 generates therapeutic radiation to be applied to a three-dimensional region in the subject at a predetermined timing. The scattering radiation detection system 3 detects scattering radiation to the outside of the subject on the basis of the irradiation radiation at a plurality of rotation angles using the axis of the emitted radiation beam as a center (step S2). For example, in the case where irradiation can be performed from one direction for three minutes, data in 18 directions is collected for 10 seconds in each of the directions. Preferably, the 18 directions are set at equal angle intervals using the beam axis as a center. The number of counting times of scattering radiation in each of the directions detected by the detector 301 and position information of the detector 301 at the time of detecting the scattering radiation measured by the position detector 307 is transmitted to the data processing system 5.

In the embodiment, it is assumed that the disposition angle of the detector 301 is set so as to detect back scattering radiation whose scattering angle θ lies in the range of 140°≦θ<180° (for example, 155°).

In the above example, for example, when irradiation of 2 Gy is performed from three directions, the number of counts per direction is $1.24 \times 10^5 \times 1/3$ which is about $4 \times 10^4$ [counts/cm$^2$]. When it is assumed that the irradiation is performed for 180 seconds per direction and measured for 10 seconds, $4 \times 10^4 \times 10/180 = 2 \times 10^3$ [counts/cm$^2$]. The count value does not make any problem for the S/N ratio.

The scattering radiation has to be detected in at least two directions. In reality, it is preferable to detect the scattering radiation in directions as many as possible. The detection positions are preferably arranged at equal angle intervals around the axis of the irradiation beam as a center.

[Pre-Process (Correcting Process and the Like) in Step S3]

In the collected data, only X rays scattered in detector disposition angle directions are counted. In reality, however, scattering of X rays occurs in all of directions as shown in FIG. 9. To finally calculate the dose [Gy] of absorption in tissues, it is necessary to correct the count values of the detectors and obtain the number of scattering times in all of the directions.

When the count in a grid is $n_{count}$, cross section of scattering at detector disposition angle $\theta_0$ is $\sigma_{\theta 0}$, and scattering cross section (total cross section) in all of the directions is $\Sigma$, a correction value N in which scattering in all of the directions is considered is determined by the following equation (10).

$$N = n_{count} \cdot \frac{\Sigma}{\sigma_{\theta_0}} \quad (10)$$

[Image Reconstructing Process in Step S4]

Next, the image reconstruction processor 503 in the data processing system 5 executes an image reconstructing process using the projection data in multiple directions to obtain scattering radiation volume data (step S4). At this time, the rotation axis of the detector 301 and the direction of the collimator are orthogonal to each other. In the case of capturing an image in an angle range of 180 degrees (+α) or larger, it is sufficient to use the CT reconstructing method. In the other case, the tomography reconstructing method is used. As the tomography reconstructing method, for example, the filtered back projection method of applying a filter process on a projection image and, after that, performing a back projection process is used. As the filter constructing method, a classical Shepp-Logan filter or a filter disclosed in Japanese Patent Application Nos. 2006-284325 and 2007-269447 is used. In particular, when the methods described in Japanese Patent Application Nos. 2006-284325 and 2007-269447 are used, a scattering radiation source distribution image having clear physical meaning can be generated.

An image obtained by performing the filtering process on the detector image and performing back projection on the resultant image shows scattering radiation occurrence density per unit volume (the number of scattering times per unit volume). Through all of the steps in the reconstructing process (various correcting processes, filter process, and back projection process), a three-dimensional distribution of scattering radiation occurrence density (scattering radiation volume data) near the place where the therapeutic radiation passes through the subject can be obtained.

[Converting Process in Step S5]

The conversion processor 505 in the data processing system 5 converts the scattering radiation volume data to absorbed dose volume data indicative of the three-dimensional distribution of the absorbed radiation dose (absorbed dose) by converting the number "n" of scattering times per unit volume calculated voxel by voxel to absorbed dose (step S5).

Energy $T_e$ received by electrons due to scattering (=energy absorbed by tissues) can be expressed by the following equation (11).

$$\text{here, } \sigma_{\theta_0} = \frac{d\sigma_e}{d\Omega}(\theta = \theta_0) \quad \Sigma \int \frac{d\sigma_e}{d\Omega} d\Omega \quad (11)$$

$$T_e = h\nu - h\nu'$$

where hv denotes energy [eV] of therapeutic X-ray beam and is set at the time of planning a treatment. Therefore, when the value of the i-th voxel (the number of scattering times per unit volume) is $n_i$, absorption energy $E_{ab, i}$ [J] in the voxel is expressed by the following equation (12).

$$h\nu_d = \frac{h\nu}{1 + \alpha(1 - \cos\theta)} \quad (12)$$

$$E_{ab,i} = \frac{n_i \times \int T_e \cdot \frac{d\sigma_e}{d\Omega} d\Omega}{\int \frac{d\sigma_e}{d\Omega} d\Omega} \times 1.602 \times 10^{-19}$$

Therefore, absorbed dose $D_i$[Gy]=[J/kg] (=absorption energy per unit mass) in the i-th voxel is expressed by the following equation (13) when average density of an organic tissue existing in the voxel is $d_i$[g/cm$^3$] and volume of the voxel is v[cm$^3$].

$$D_i = \frac{E_{ab,i}}{v \cdot d_i} \times 10^3 \quad (13)$$

The average density $d_t[g/cm^3]$ of an organic tissue existing in the voxel may be set as 1 $[g/cm^3]$ by approximately regarded that 100% of the human body is made of water.

[Generation of Absorbed Dose Image Data and Display of Image Data in Steps S6 and S7]

Next, the image processor 507 generates absorbed dose image data indicative of the distribution of radiation dose absorbed (absorbed dose) by a predetermined region in the subject by using the absorbed dose volume data or the like and, for example, combined with a CT image so as to be fusion-displayed (step S6). The display unit 6 displays an absorbed dose image in a predetermined form (step S7).

FIG. 18 is a diagram showing a form of display (fusion display) of the absorbed dose image. At an arbitrary timing during, before, or after treatment, an absorbed dose image as shown in the diagram can be displayed. The operator observes the displayed image and can visually and quantitatively grasp a dose in an actual region in the patient.

(Effects)

With the above-described configuration, the following effects can be obtained. The detector having the collimator is mounted in a position at a specific angle (scattering angle) with respect to a therapeutic X-ray beam, only scattering radiation in the direction is selectively detected, and the detection is executed in multiple directions with respect to the same scattering angle. Scattering radiation volume data is reconstructed by using the scattering radiation data in multiple directions on the obtained predetermined scattering angle. The scattering radiation volume data is converted to absorbed dose volume data indicative of a three-dimensional distribution of the absorbed radiation dose, and an absorbed dose image is generated. The generated absorbed dose image is combined with, for example, a shape image (CT image or the like) and the resultant image is displayed. The displayed absorbed dose image is generated on the basis of scattering radiation data in multiple directions as objective data obtained by actual measurement. Therefore, by observing the absorbed dose image, the operator can visually and quantitatively grasp the actual irradiation position and amount of the radiation. Thus, whether the radiation treatment is performed as planned or not can be determined by using an objective criterion, and excessive or insufficient irradiation of radiation to a treatment region and its peripheral region can be prevented. As a result, improvement in the effect of the radiation treatment and reduction in the excessive exposure amount to the subject can be realized, and it can contribute to improve the quality of the radiation treatment.

With the radiotherapeutic system 1, the absorbed dose image can be observed in a real-time manner during treatment. By performing the reconstructing process and a predetermined image process using the scattering radiation volume data and the absorbed dose volume data obtained in advance, the absorbed dose image can be observed at an arbitrary timing. Therefore, during treatment, the position and intensity of radiation which is presently emitted can be recognized in a real-time manner promptly, easily, and visually. For example, during a therapeutic process, the positions irradiated with the radiation in the past treatments and accumulated radiation dose can be recognized promptly, easily, and visually. That is, by observing the absorbed dose image in a desired state, the operator can determine appropriateness of the present treatment and past treatment on the basis of the objective criteria.

Second Embodiment

A second embodiment of the present invention will now be described. A radiotherapeutic system in the second embodiment measures scattering radiation from a subject based on radiation applied to the subject and, on the basis of the measured scattering radiation, obtains, as absorbed dose, information objectively showing a region in the subject and a dose.

FIG. 19 is a block configuration diagram of a radiotherapeutic system 1 of the second embodiment. FIG. 19 is different from FIG. 2 with respect to the configuration of the data processing system 5 and the storing unit 7.

The data processing system 5 has a correction processor 501, a reconstruction processor 503, a conversion processor 505, and an image processor 507.

The correction processor 501 performs a data calibration process, a correcting process for eliminating noise, and the like as necessary. The correcting process executed by the correction processor 501 will be described in detail later.

The reconstruction processor 503 executes an image reconstructing process using scattering radiation image data detected by the scattering radiation detection system 3 and position information indicative of a position in which the scattering radiation image data is detected to obtain scattering radiation volume data indicative of a three-dimensional distribution of density of the number of scattering events (the number of scattering occurrence times). As the reconstructing method, for example, when the direction of the collimator is orthogonal to the scan axis, a CT (Computerized Tomography) reconstructing method is used. On the other hand, when the direction of the collimator is not orthogonal to the scan axis, a tomography reconstructing method is used.

The conversion processor 505 converts three-dimensional image data obtained by the image reconstructing process to absorbed dose volume data indicative of a three-dimensional distribution of absorbed radiation dose (absorbed dose).

The image processor 507 generates absorbed dose image data indicative of a distribution of radiation dose (absorbed dose) absorbed in a predetermined region in the subject by using the absorbed dose volume data or the like. In the case of displaying an absorbed dose image by fusion imaging, the image processor 507 performs an image synthesizing process using the absorbed dose volume data and the like.

[Display Unit, Storing Unit, Operating Unit, and Network I/F]

The display unit 6 displays an absorbed dose image in a predetermined form by using the absorbed dose image data. For example, as necessary, the display unit 6 fuses the absorbed dose image with a plan image and images obtained just before irradiation and during the irradiation, and displays the resultant image.

The storing unit 7 stores scattering radiation volume data, absorbed dose volume data, and absorbed dose image data obtained by a predetermined scan sequence for acquiring (scanning) scattering radiation data while rotating the detector 301 using the axis of a radiation beam emitted as a center, a control program for executing the correcting process, the image reconstructing process, the converting process, the display process, and the like, a dedicated program for displaying and editing a treatment plan in the system, and the radiotherapeutic system 1, image data obtained by other modalities such as an X-ray computerized tomography apparatus, and the like. The storing unit 7 also stores a CT value/density conversion table 701. The CT value/density conversion table 701 is used for a converting process, and its details will be described later. The data stored in the storing unit 7 can be also transferred to an external apparatus via a network I/F 90.

A method of measuring scattering radiation (absorbed dose image data generating method) using the radiotherapeutic system 1 is typically the same as that described in the first embodiment. It will be briefly reviewed. The treatment effect of the external X-ray irradiation is produced mainly by scattering of the X-ray in the patient body. Specifically, when a therapeutic X-ray beam is scattered by electrons in the patient body, the electrons which receive the energy fly in tissues and then stop. Until the electrons stop, the electrons generate radicals from molecules in the tissues, and damage DNA in the cells. The cells which are damaged and could not be repaired finally die. This is the effect of the treatment with the X-ray irradiation. The more recoil electrons are generated, the higher the probability that cells constructing a tissue die becomes. Consequently, the treatment effect is proportional to the number of occurrence times of scattering reaction.

From the above, when the number of times of scattering that occurs in a tissue is known, the treatment effect (how the tissue is damaged) can be known. The number of occurrence times of scattering can be known by measuring the number of scattering radiation. The travel directions of most of X rays scattered are changed by the electrons, and the resultant rays go out from the patient body, so that they can be measured by an X-ray detector mounted on the outside of the patient body.

In the radiotherapeutic system of the first example of the present embodiment, a detector having a collimator is mounted in a position at a specific angle with respect to a therapeutic X-ray beam and selectively detects only scattering radiation in the direction. Since the angle and the degree of an X-ray scattered by Compton scattering are known theoretically, if scattering radiation at a certain angle can be detected, the number of scattering radiation at other angles can be also estimated. Further, to three-dimensionally obtain a distribution of places where scattering occurs in the patient body, the detector is rotated during irradiation and scattering radiation is measured from all of directions (refer to, for example, FIG. 3). After that, a reconstructing process is performed, and a distribution of occurrence of scattering radiation in the subject is three-dimensionally imaged.

In the radiotherapeutic system of the second example of the present embodiment, a detector having a collimator is mounted in a position at a specific angle (scattering angle) with respect to a therapeutic X-ray beam and selectively detects only scattering radiation in the direction. By executing the detection while moving the therapeutic X-ray beam and the detection face and maintaining the angle formed between the axis of the therapeutic X-ray beam emitted from the irradiating unit and the detection face of the detector, a three-dimensional region in the subject is scanned. Scattering radiation volume data is reconstructed by using obtained three-dimensional scattering radiation data at the predetermined scattering angle, the scattering radiation volume data is converted to absorbed dose volume data indicative of a three-dimensional distribution of the absorbed radiation dose, and an absorbed dose image is generated.

(Absorbed Dose Image Data Generating Method)

FIRST EXAMPLE

An absorbed dose image data generating method using the radiotherapeutic system 1 of a first example will be described. In the radiotherapeutic system of the first example, a detector having a collimator is mounted in a position at a specific angle with respect to a therapeutic X-ray beam and selectively detects only scattering radiation in the direction. Further, to three-dimensionally obtain a distribution of places where scattering occurs in the patient body, the detector is rotated during irradiation and scattering radiation is measured from all of directions (refer to, for example, FIG. 3). After that, a reconstructing process is performed, and a distribution of occurrence of scattering radiation in the subject is three-dimensionally imaged.

FIG. 20 is a flowchart showing the flow of processes in radiation treatment including the absorbed dose image data generating process of the example. The processes in the steps will be described below.

[Disposition of Subject and the Like in Step S1a]

First, the data acquisition controller 4 acquires treatment plan information on the subject via, for example, a network and displays it on the display unit 6. The operator disposes the subject on the bed in accordance with the displayed treatment plan and performs selection of a scan sequence, such as setting of radiation irradiation time, the number of times of measuring scattering radiation in one rotation, setting of measurement angle, and the like via the operating unit 8 (step S1a). The radiation irradiation time and the like may be automatically set on the basis of the obtained treatment plan information.

[Radiation Irradiation and Acquisition of Scattering Radiation Image Data in Multiple Directions in Step S2a]

FIG. 3 shows a form of measuring scattering radiation of the radiotherapeutic system 1. As shown in the diagram, the radiation irradiation system 2 generates therapeutic radiation to be applied to a three-dimensional region in the subject at a predetermined timing. The scattering radiation detection system 3 detects scattering radiation to the outside of the subject on the basis of the irradiation radiation at a plurality of rotation angles using the axis of the emitted radiation beam as a center (step S2a). For example, in the case where irradiation can be performed from one direction for three minutes, data in 18 directions is collected for 10 seconds in each of the directions. Preferably, the 18 directions are set at equal angle intervals using the beam axis as a center. The number of counting times of scattering radiation in each of the directions detected by the detector 301 and position information of the detector 301 at the time of detecting the scattering radiation measured by the position detector 307 is transmitted to the data processing system 5.

In the example, it is assumed that the disposition angle of the detector 301 is set so as to detect back scattering radiation whose scattering angle θ lies in the range of $140° \leq \theta < 180°$ (for example, 155°).

In the above example, for example, when irradiation of 2 Gy is performed from three directions, the number of counts per direction is $1.24 \times 10^5 \times \frac{1}{3}$ which is about $4 \times 10^4$ [counts/cm$^2$]. When it is assumed that the irradiation is performed for 180 seconds per direction and measured for 10 seconds, $4 \times 10^4 \times 10/180 = 2 \times 10^3$ [counts/cm$^2$]. The count value does not make any problem for the S/N ratio.

The scattering radiation has to be detected in at least two directions. In reality, it is preferable to detect the scattering radiation in directions as many as possible. The detection positions are preferably arranged at equal angle intervals around the axis of the irradiation beam as a center.

[Pre-Process (Correcting Process and the Like) in Step S3a]

In the collected data, only X rays scattered in detector disposition angle directions are counted. In reality, however, scattering of X rays occurs in all of directions. The correction processor 501 in the data processing system 5 corrects the count values of the detectors and obtains the number of scattering times in all of the directions in accordance with a predetermined calculation formula (step S3a).

[Image Reconstructing Process in Step S4a]

The reconstruction processor 503 in the data processing system 5 executes an image reconstructing process using the projection data in multiple directions to obtain scattering radiation volume data (step S4a). At this time, the rotation axis of the detector 301 and the direction of the collimator are orthogonal to each other. In the case of capturing an image in an angle range of 180 degrees (+α) or larger, it is sufficient to use the CT reconstructing method. In the other case, the tomography reconstructing method is used. As the tomography reconstructing method, for example, the filtered back projection method of applying a filter process on a projection image and, after that, performing a back projection process is used. As the filter constructing method, a classical Shepp-Logan filter or a filter disclosed in Japanese Patent Application Nos. 2006-284325 and 2007-269447 is used. In particular, when the methods described in Japanese Patent Application Nos. 2006-284325 and 2007-269447 are used, a scattering radiation source distribution image having clear physical meaning can be generated.

An image obtained by performing the filtering process on the detector image and performing back projection on the resultant image shows scattering radiation occurrence density per unit volume (the number of scattering times per unit volume). Through all of the steps in the reconstructing process (various correcting processes, filter process, and back projection process), a three-dimensional distribution of scattering radiation occurrence density (scattering radiation volume data) near the place where the therapeutic radiation passes through the subject can be obtained.

[Converting Process in Step S5a]

The conversion processor 505 in the data processing system 5 converts the scattering radiation volume data to absorbed dose volume data indicative of the three-dimensional distribution of the absorbed radiation dose (absorbed dose) by converting the number "n" of scattering times per unit volume calculated voxel by voxel to absorbed dose (step S5a). The details of the process will be described later.

[Generation of Absorbed Dose Image Data and Display of Image Data in Steps S6a and S7a]

The image processor 507 generates absorbed dose image data indicative of the distribution of radiation dose absorbed (absorbed dose) by a predetermined region in a subject CT image and, for example, combines it with a CT image (step S6a). The display unit 6 displays an absorbed dose image in a predetermined form (step S7a).

SECOND EXAMPLE

An absorbed dose image data generating method using the radiotherapeutic system 1 of a second example will now be described. In the radiotherapeutic system of the second example, a detector having a collimator is mounted in a position at a predetermined angle (scattering angle) with respect to a therapeutic X-ray beam and selectively detects only scattering radiation in the direction. By executing the detection while moving the therapeutic X-ray beam and the detection face and maintaining the angle formed between the axis of the therapeutic X-ray beam emitted from the irradiating unit and the detection face of the detector, a three-dimensional region in the subject is scanned. Scattering radiation volume data is reconstructed by using obtained three-dimensional scattering radiation data at the predetermined scattering angle, the scattering radiation volume data is converted to absorbed dose volume data indicative of a three-dimensional distribution of the absorbed radiation dose, and an absorbed dose image is generated.

FIG. 21 is a flowchart showing the flow of processes in radiation treatment including the absorbed dose image data generating process of the example. The processes in the steps will be described below.

[Disposition of Subject and the Like in Step S1b]

First, in a manner similar to the first example, the subject is disposed (step S1b).

[Radiation Irradiation (Acquisition of Scattering Radiation Data) in Step S2b]

FIG. 22 is a diagram showing an example of a form of measuring scattering radiation of the radiotherapeutic system 1. As shown in the diagram, the radiation irradiation system 2 emits an X-ray beam B2 shaped in a thin flat shape to the subject at a predetermined timing. The scattering radiation detection system 3 detects scattering radiation at a predetermined scattering angle to the outside of the subject on the basis of the irradiation radiation. The data acquisition controller 4 controls the gantry controller 207 or the movement mechanism 305 so as to move an excitation cross section of the X-ray beam B2 while maintaining the angle formed between the axis of the X-ray beam B2 for treatment emitted from the irradiating unit 203 and the visual line direction of the detector 301 and scanning a three-dimensional region in the subject (step S2b). By the scanning of the three-dimensional region with the X-ray beam B2 for treatment, three-dimensional scattering radiation data made of a plurality of pieces of two-dimensional scattering radiation data corresponding to the plane of the X-ray beam B2 is obtained.

FIG. 22 shows an example of the scattering radiation measuring form. The scattering radiation measuring form of the example is not limited to the example. For example, as shown in FIG. 23, also by moving the detection face of the detector 301 (and the opening face of the collimator 303) interlockingly with movement of the position of the axis of the radiotherapeutic beam while maintaining the angle of the detection face with respect to the irradiation direction of the radiotherapeutic beam constant, three-dimensional scattering radiation data made of a plurality of pieces of two-dimensional scattering radiation data can be obtained.

[Pre-Process (Correcting Process and the Like) in Step S3b]

The correction processor 501 in the data processing system 5 executes a pre-process including attenuation correction and obtains projection data (step S3b). The attenuation correction denotes a correcting process regarding signal attenuation which occurs when therapeutic radiation or scattering radiation propagates in a subject.

[Image Reconstructing Process in Step S4b]

The reconstruction processor 503 in the data processing system 5 executes an image reconstructing process using the obtained projection data to obtain scattering radiation volume data (step S4b).

[Converting Process in Step S5b]

The conversion processor 505 in the data processing system 5 converts the scattering radiation volume data to absorbed dose volume data indicative of the three-dimensional distribution of the absorbed radiation dose (absorbed dose) in a manner similar to the first example (step S5b). The details of the process will be described later.

[Generation of Absorbed Dose Image Data and Display of Image Data in Steps S6b and S7b]

The image processor 507 generates, using the absorbed dose volume data and the like, absorbed dose image data indicative of the distribution of radiation dose absorbed (absorbed dose) by a predetermined region in a subject and, for example, combines it with a CT image so as to perform fusion display (step S6b). The display unit 6 displays an absorbed dose image in a predetermined form (step S7b).

The details of the converting process in the steps S5a and S5b will be described.

As shown in FIG. 24, when it is assumed that a human tissue is made of homogeneous water, if a material having largely different density exists nearby, there is the possibility that the absorbed dose is underestimated. Specifically, the absorbed dose in tissue having density largely different from that of homogeneous water such as lung or hollow organ including air, bone, or the like cannot be calculated accurately. In the embodiment, density corresponding to the composition (the ratio of component and dose included in the component) of tissue is calculated on the voxel unit basis using a CT image of the subject captured, so that more accurate absorbed dose is obtained.

FIG. 25 is a flowchart showing the procedure of the converting process. The processes in the steps will be described below.

[Reading of CT Image in Step S1c]

The data processing system 5 reads a CT image of a patient. The CT image is finally displayed in comparison with the absorbed dose distribution and, desirably, accurately shows the state of the patient being treated. For example, a CT image of the patient in the same posture as that during the treatment captured just before the treatment (which can be captured by, for example, an apparatus called Linac integrated CT) is used.

[Calculation of Mass Density of Voxel in CT Image in Step S2c]

The conversion processor 505 converts the CT value of each of voxels of a CT image to mass density. The process is performed as follows. First, the CT value is converted to relative electron density. The relative electron density denotes the ratio between electron density of a material and electron density of water. The relation between the CT value and the relative electron density $\rho_e$ can be measured by using a phantom. For example, the following relation is known (S. J. Thomas, "Relative electron density calibration of CT scanners for radiotherapy treatment planning", The British Journal of Radiology, August 1999). HU stands for Hounsfield Unit and is a CT value.

$$L_1 = 2 \cdot \left( \frac{l}{\cos\phi} + a\tan(|\theta - \frac{\pi}{2}|) + a\tan\phi \right) \cdot \sin(\pi - \theta) \quad (1)$$

By using the above equation, the relative electron density of a voxel in a CT image is known. Since the equation is based on data captured with an X-ray tube voltage of 120 to 140 keV, in the case of using a CT image captured with another X-ray tube voltage, measurement using a phantom has to be carried out separately, and a conversion equation between the CT value and the relative electron density has to be obtained.

Further, the relative electron density is converted to mass density. 99% or more of the elements of a human body has atomic number of 20 or less. As shown in FIG. 26, in a range where the atomic numbers are relatively small, the atomic number, that is, the number of electrons of an atom and atomic weight are almost proportional. It can be regarded that the electron density and the mass density in a human body have a similar relation. Consequently, in a voxel having relative electron density is 2.0 (which is twice as high as the electron density of water), it can be regarded that the mass density is 2.0 [g/cm$^3$] which is twice as high as that of water.

By the approximate conversion, almost accurate mass density can be obtained. The value will be compared with values in the following literature.

Since the relative electron density of fat is 0.96 g/cm$^3$ (literature value), in the above method, the mass density is converted to 0.96 g/cm$^3$ (literature value of the mass density: 0.94 g/cm$^3$).

Since the relative electron density of muscle is 1.05 g/cm$^3$ (literature value), in the above method, the mass density is converted to 1.05 g/cm$^3$ (literature value of the mass density: 1.06 g/cm$^3$).

Source of relative electron density: Yukihiro Matsuda, et al., "Investigation of a CT value electron density conversion method in radiotherapy planning CT", Japanese Journal of Radiological Technology, Vol. 63, No. 8, 888-, 2007

Source 1 of mass density: official site of Japan Synchro Committee of Japan Swimming Federation (URL: http://synchrocafe.ijiss.jp/modules/smartsection/item.php?itemid=43)

Source 2 of mass density: "Synchronized Swimming Consistent Teaching Book", Japan Swimming Federation, 2002

As necessary, a table of the corresponding relation between the obtained CT value and the mass density is formed and stored as the CT value/density conversion table 701 in the storing unit 7.

[Positioning of CT Image/Dose Distribution Image in Step S3c]

The image processor 507 positions the images to associate voxels of the CT image and those of a dose distribution image with each other. In the case of using a CT image captured with the same posture as that during treatment or a CT image at the time of generating a treatment plan immediately before treatment, the position in an irradiation apparatus coordinate system using the irradiation center as the origin is known. Consequently, the process can be easily executed.

[Calculation of Mass Density of Voxel in Dose Distribution Image in Step S4c]

Next, the mass density of each of the voxels of the dose distribution image is calculated from a mass density value of the corresponding voxel in the CT image. The voxel sizes of the images are generally different from each other. In many cases, the relation that the voxel size of the dose distribution image is larger than that of the CT image is satisfied (although the CT image can be captured with the voxel size of 1 mm or less, if the dose distribution image is obtained with a smaller voxel size, precision deteriorates and it is difficult in practice). In this case, it is sufficient to obtain an average value. Further, depending on the positional relation of the images, the number of CT image voxels included in a dose distribution image voxel becomes a non-integer. When the number of voxels in a CT image which is partially or entirely included in the j-th voxel in the dose distribution image is l, the volume percent of each voxel is $v_i$ (i=1, 2, . . . , l), and the mass density is $\rho_i$ (i=1, 2, . . . , l), the mass density $\rho_j^{Dose}$ of the j-th voxel in the dose distribution image is calculated by the following equation.

$$L_1 = 2 \cdot \left( w + a\tan(|\theta - \frac{\pi}{2}|) \right) \cdot \sin(\pi - \theta) \quad (2)$$

[Calculation of Absorbed Dose [Gy] in Step S5c]

The absorbed dose $D_j$[Gy]=[J/kg] of the j-th voxel in the dose distribution image can be calculated by the following equation when absorption energy $E_{ab,\ j}$[J], mass density $\rho_j^{Dose}$[g/cm$^3$], and volume v[cm$^3$] of the voxel are used.

$$\frac{d\sigma_e}{d\Omega} = \frac{r_0^2}{2}(2 - \sin^2\theta)F_{KN} = \frac{r_0^2}{2}(1 + \cos^2\theta)F_{KN} \quad (3)$$

$$F_{KN} = \left\{\frac{1}{1 + \alpha(1 - \cos\theta)}\right\}^2 * \left[1 + \frac{\alpha^2(1 - \cos\theta)^2}{\{1 + \alpha(1 - \cos\theta)\}} \atop (1 + \cos^2\theta)\right]$$

In the embodiment as described above, the radiation irradiation system 2 emits a radiotherapeutic beam to the subject, and the scattering radiation detection system 3 detects scattering radiation from the subject generated on the basis of the radiotherapeutic beam, and generates scattering radiation data. On the basis of the detected scattering radiation data, the reconstruction processor 503 reconstructs scattering radiation volume data indicative of a three-dimensional distribution of scattering radiation occurrence density in the subject. The conversion processor 505 converts the scattering radiation volume data to absorbed dose volume data indicative of the three-dimensional distribution of the absorbed radiation dose by using the density corresponding to the composition of the tissue of each voxel.

When an absorbed dose distribution image is generated by regarding a human tissue as homogeneous water, if a material having largely different density exists nearby, there is the possibility that the absorbed dose is underestimated. In contrast, the embodiment has an advantage that accurate dose evaluation can be performed also in the case where a tissue having largely different density such as a tumor in the lung field is adjacent. Therefore, whether radiation treatment is performed according to the treatment plan or not can be accurately determined, and insufficient irradiation to a region to be treated with radiation, excessive irradiation to a normal region in the periphery of the region to be treated, and the like can be prevented. As a result, the effect of the radiation treatment can be improved, reduction in excessive exposure amount to the subject can be realized, and the invention can contribute to safety of the radiation treatment and improvement in quality.

Third Embodiment

A third embodiment of the present invention will now be described. A radiotherapeutic system in the third embodiment executes a reconstructing process using attenuation correction.

FIG. 27 is a block configuration diagram of a radiotherapeutic system 1 of the third embodiment. FIG. 27 is different from FIG. 2 with respect to the configuration of the data processing system 5.

The data processing system 5 has a correction processor 501, an attenuation coefficient distribution estimating unit 502, a reconstruction processor 503, a conversion processor 505, and a data processor 507.

The correction processor 501 performs a data calibration process, a correcting process for eliminating noise, and the like as necessary.

The attenuation coefficient distribution estimating unit 502 estimates a spatial distribution of an attenuation coefficient on a region irradiated with radiation including a radiation treatment region by using a CT image or the like captured for a treatment plan. The estimating process will be described in detail later.

The reconstruction processor 503 executes an image reconstructing process using scattering radiation image data detected by the scattering radiation detection system 3 and position information indicative of a position in which the scattering radiation image data is detected to obtain scattering radiation volume data indicative of a three-dimensional distribution of density of the number of scattering events (the number of scattering occurrence times). As the reconstructing method, for example, when the direction of the collimator is orthogonal to the scan axis, a CT reconstructing method is used. On the other hand, when the direction of the collimator is not orthogonal to the scan axis, a tomography reconstructing method is used. Particularly, the reconstruction processor 503 executes the image reconstructing process accompanying attenuation correction by using the estimated spatial distribution of the attenuation coefficient, and obtains scattering radiation volume data subjected to the attenuation correction. The image reconstructing process accompanying attenuation correction will be described in detail later.

The conversion processor 505 converts three-dimensional image data obtained by the image reconstructing process to absorbed dose volume data indicative of a three-dimensional distribution of absorbed radiation dose (absorbed dose).

<Attenuation Coefficient Distribution Estimating Function>

The attenuation coefficient distribution estimating function of the radiotherapeutic system 1 will now be described. The function is to estimate an attenuation coefficient on a region irradiated with radiation including a radiation treatment region by using a CT image or the like obtained for a treatment plan. As the CT images used, a preoperative CT image for treatment plan, a CT image just before treatment, and a CT image by MVCT assembled in the radiotherapeutic system, or a CT image by MVCT assembled in the radiotherapeutic system can be mentioned. An attenuation coefficient estimating process which varies according to a CT image used has to be performed. A process according to the attenuation coefficient distribution estimating function (attenuation coefficient distribution estimating process) is executed at an arbitrary timing before radiation treatment, and an attenuation coefficient distribution obtained by the process is stored in the storing unit 7.

FIG. 28 is a flowchart showing the flow of the attenuation coefficient distribution estimating process. By using the diagram, the attenuation coefficient distribution estimating process executed by the attenuation coefficient distribution estimating processor 502 will be described below.

The attenuation coefficient distribution estimating processor 502 receives a CT image corresponding to a region irradiated with radiation which is obtained by an X-ray CT apparatus (step SA). An attenuation coefficient $\mu_{60}$ obtained from the CT image can be obtained from a CT value as shown by the following equation (14).

$$\rho_e = \frac{HU}{1950} + 1.00 \text{ for } HU \geq 0 \quad (14)$$

$$\rho_e = \frac{HU}{1000} + 1.00 \text{ for } HU \leq 0$$

$$\rho_j^{Dose} = \frac{1}{l}\sum_i^l v_i \rho_i$$

$$D_i = \frac{E_{ab,j}}{v \cdot \rho_j^{Dose}} \times 10^{-3}$$

$$\mu_{60} = \left(1 + \frac{CT \text{ value}}{1000}\right)\mu_{water}$$

The attenuation coefficient is an attenuation coefficient in effective monochromatic energy of an X ray generated by the X-ray CT apparatus. What the attenuation correction needs is an attenuation coefficient $\mu_{sc}$ in energy of scattering radiation, so that the attenuation coefficient cannot be used as it is. Therefore, in various methods, the attenuation coefficient has to be converted to an attenuation coefficient in energy of scattering radiation.

The attenuation coefficient distribution estimating processor 502 estimates an attenuation coefficient by linear transformation according to the following equation (15) (step SB). Transformation parameters "a" and "b" are determined in advance from measurement values of attenuation coefficients in photon energies of water, muscle, fat, bone, and the like.

$$\log_{10}\mu_{sc} = \alpha \log_{10}\mu_{60} + b \tag{15}$$

Since energy dependence of the attenuation coefficient varies according to atoms, the attenuation coefficient has to be transformed with a coefficient which varies according to a tissue in order to obtain an accurate attenuation coefficient. Therefore, for example, by the following equation (16), the attenuation coefficient distribution estimating processor 502 roughly divides tissues to a tissue having a large attenuation coefficient and a tissue having a small attenuation coefficient, and the attenuation coefficients are estimated by different transformation equations (step SC).

$$\mu(E_{sc}) = \begin{cases} 4.7096 \times \mu_{60} \times E_{sc}^{-0.373} & \mu_{60} \leq 0.2244 \\ 3.165 \times (\mu_{60} - 0.2244) \times (E_{sc} - 45)^{-0.4703} + 0.2244 & \mu_{60} > 0.2244 \end{cases} \tag{16}$$

where $\mu_{60}$ denotes an attenuation coefficient obtained by imaging in an X-ray CT apparatus having an effective monochromatic energy of 60 eV. $E_{sc}$ denotes effective monochromatic energy of scattering radiation and can be obtained by the following equation (17).

$$E_{sc} = \frac{hv}{1 + \alpha(1 - \cos\theta)} \alpha = \frac{hv}{mc^2} \tag{17}$$

where hv denotes the effective monochromatic energy of therapeutic radiation and "m" denotes electron rest mass. In the above method, a transformation equation in the case where $\mu_{60} \leq 0.2244$ is a transformation equation of the attenuation coefficient for muscle. A transformation equation in the case where $\mu_{60} > 0.2244$ is a transformation equation of the attenuation coefficient for a region of bone. Similarly, transformation equations for regions of fat and air can be easily added.

The attenuation coefficient distribution estimating processor 502 repeats the processes in the steps SA to SC on all of the positions in the region to be irradiated (a region to be irradiated with therapeutic radiation or irradiated region) and generates an attenuation coefficient distribution on the region to be irradiated (step SD).

<Attenuation Correcting Function>

The attenuation correcting function of the radiotherapeutic system 1 will now be described. In the function, an image reconstructing process accompanying attenuation correction is executed by using an attenuation coefficient distribution obtained by, for example, a known estimating process, thereby generating scattering radiation volume data subjected to the correction. A process according to the attenuation correcting function (attenuation correcting process) is executed in, for example, step S4a in FIG. 20 and step S4b in FIG. 21.

FIG. 29 is a flowchart showing the flow of the attenuation correcting process. As shown in the diagram, the reconstruction processor 503 executes back projection process on each of Np pieces of projection images measured in Np positions and corrected, divides each of the back projection results by a correction value $c_k(x)$, and adds the resultant values to generate scattering radiation volume data. $c_k(x)$ denotes a coefficient for correcting the influence of attenuation, and total attenuation from the position (x) of a dot radiation source to the k-th detector can be calculated by the following equation (18).

$$c_k(x) = \exp\left(-\int \mu(x + ln_k) dl\right) \tag{18}$$

As shown in FIG. 30, x shows the position in the reconstruction space, and $n_k$ shows the direction of the k-th projection. The back projection accompanying the attenuation correction can be expressed by the following equation (19).

$$f(x) = \frac{1}{N_p} \sum_{k=1}^{N_p} \frac{g_k(p_k(x))}{c_k(x)} \tag{19}$$

where f(x) denotes a reconstruction image subjected to the attenuation correction, $g_k(u)$ denotes a projection image of the k-th projection in a position "u" on the detector, and $p_k(x)$ indicates a position on the detector obtained by projecting the position "x" in the reconstruction space to the detection face of the k-th projection. There are various methods of executing the back projection process, and the above expressing method is just an example.

For reference, an example of the flow of the conventional reconstructing process which does not accompany the attenuation correction is shown in FIG. 31.

<Detailed Description of Reconstructing Process>

Next, the details of the reconstructing process executed by the reconstruction processor 503 will be described.

[Modeling of Projection Process]

A state where radiation scattered at a point in a subject enters a detector is modeled as follows.

1. Angle Dependency of Scattering and Probability of Incidence on Detector

It is assumed that scattering radiation scattered in a direction different from the irradiation direction of the therapeutic radiation only by the angle θ enters a detector pixel. Scattering occurs in all directions but has angle dependency. The ratio of scattering radiation entering the detector pixel in all of scattering radiation is expressed as $R\Delta\Omega(x)$ (incidence probability). In this case, the existence of the collimator is ignored. $\Delta\Omega(x)$ denotes a solid angle between the position x and the detector pixel. A proportionality coefficient R (incidence probability per unit solid angle) is a value obtained by dividing a differential scattering cross section $d\sigma(\theta)/d\Omega$ by a total scattering cross section.

2. Collimator Sensitivity Distribution

A scattering radiation incident on the detector position "u" also has angle dependency. A scattering radiation from the axis direction of the collimator enters the detector at the highest probability, and a scattering radiation from a direction largely deviated from the axis does not enter the detector. As shown in FIGS. 32A and 32B, the probability of scattering radiation incident from the position "x" in the subject space to the detector pixel position "u" is expressed as collimator sensitivity h(x, u).

3. Scattering Radiation Incidence Model A

Area density e(u) of a scattering radiation entering the position "u" of the detector pixel from a small volume dx of the subject can be expressed by the following equation (20).

$$e(u) = \frac{1}{A_e} \int h(x, u) R \Delta \Omega N_v \, dx \qquad (20)$$

where $N_v$ denotes all-around scattering density (the number of scattering times in all of directions per unit volume), e(u) denotes incidence scattering radiation density of the position "u" of the detector, and $A_e$ denotes area of the detector pixel. An integral sign expresses a volume integral in a space around the subject.

4. Scattering Radiation Incidence Model B

To simplify the equation (20), the volume integral of the equation (20) is decomposed to integral of the direction of a collimator axis "t" and a plane S orthogonal to the direction as the following equation (21).

$$e(u) = \int \left( \frac{1}{A_e} \int_S h(x, u) R \Delta \Omega N_v \, ds \right) dt \qquad (21)$$

where ds denotes an element of the orthogonal plane S. Since there is no large fluctuation in $N_v$, R, and $\Delta\Omega$ in the range of the area integral of the orthogonal plane, integrand of "t" in the equation (21) can be approximated like the following equation (22).

$$\frac{1}{A_e} \int_S h(x, u) R \Delta \Omega N_v \, ds \cong \frac{R N_v}{A_e} \left( \Delta \Omega \int_S h(x, u) \, ds \right) \qquad (22)$$

The integral in the right side of the equation (22) corresponds to an opening area of the collimator and is proportional to the square of the distance from the detection face. The solid angle $\Delta\Omega$ is inversely proportional to the square of the distance from the detection face. Therefore, a value in parentheses on the right side of the equation (22) as an integral of the integral and the angle is almost constant at each position in the direction of the collimator axis. An area $A_c$ as shown by the following equation (23) is introduced.

$$A_c = \frac{A_e}{\Delta \Omega \int_S h(x, u) \, ds} \qquad (23)$$

When the equation (23) is used, the equation (22) can be simplified as the following equation (24).

$$\frac{1}{A_e} \int_S h(x, u) R \Delta \Omega N_v \, ds \cong \frac{R N_v}{A_e} \left( \Delta \Omega \int_S h(x, u) \, ds \right) = \frac{R N_v}{A_c} \qquad (24)$$

When the equation (24) is substituted to the equation (23), the following equation (25) or (26) is obtained.

$$e(u) \cong \frac{R}{A_c} \int N_v \, dt \qquad (25)$$

$$e'(u) \cong \int N_v \, dt, \; e'(u) = \frac{A_c}{R} e(u) \qquad (26)$$

The equation (26) corresponds to correction on the scattering angle dependency of the scattering radiation and correction from a scattering radiation in a specific direction range narrowed by the collimator to the number of scattering times in all of directions among the correcting process of the projected image.

[Computing Equations of Projection and Back Projection Applied to Reconstruction]

In the reconstructing process, the function f(x) in the reconstruction space is estimated from $N_p$ pieces of projection images $g_k(u)$ (k=1, 2, ..., $N_p$). To perform the reconstructing process like in Japanese Patent Application Nos. 2006-284325 and 2007-269447, the back projection process and the projection process have to be changed so as to be adapted to the issue of the proposal. Two examples will be described below.

When the scattering radiation incident model A is used directly, the equation (20) can be used directly as a definitional equation of the projection computation. A definitional equation of the projection computation in this case is the following equation (27).

$$g_k(u) = \frac{1}{A_e} \int h(x, u) R \Delta \Omega f(x) \, dx \qquad (27)$$

As a definitional equation of the back projection computation, the following equation (28) obtained by inverting the equation (27) is used.

$$f_b(x) = \frac{1}{N_P} \sum_{k=1}^{N_P} \left( \frac{T}{A_e} \int_D h(x, u) R \Delta \Omega g_k(u) \, du \right) \qquad (28)$$

where an integral on "u" expresses the area integral on the detection face. T denotes a constant number having a length dimension and is an arbitrary value. To simplify the equation, the expression $T/A_e=1$ may be used.

When the scattering radiation incident model B in the equation (26) is used, the projection computation can be expressed as the following equation (29).

$$g_k(u) = \int f(x) \, dt \qquad (29)$$

By using the equation (29), the back projection computation can be expressed more simply like the following equation (30).

$$f_b(x) = \frac{1}{N_P} \sum_{k=1}^{N_P} T g_k(u) \qquad (30)$$

where T denotes a constant number having a length dimension and is an arbitrary value. To simplify the equation, it may be expressed as T=1. Equations (29) and (30) are the same as the projection computation and the back projection computation, respectively, of an X-ray CT apparatus and an X-ray tomography. Therefore, by using the equations, various reconstructing methods of an X-ray CT apparatus and an X-ray CT scan can be used.

In the attenuation correcting process, the back projection process accompanying attenuation correction is executed according to the equation (19). The equation (19) has a form very close to that of the equation (30) but is different with respect to the point that the denominator of the equation (19) is multiplied by a correction coefficient $c_k$ of the attenuation correction. That is, in the configuration of the back projection process accompanying the attenuation correction, division with the correction coefficient $c_k$ is newly added to the normal back projection process.

[Reconstruction for Obtaining Absorbed Dose in Consideration of Attenuation Correction]

In the above-described attenuation correction, the all-around scattering density is multiplied with the absorption energy per scattering and the inverse of density to obtain absorbed dose (J/kg) in the place. A method of reconstructing a value converted to the absorbed dose in consideration of an attenuation correction will be described.

A projection image $g_k(u)$ is discretized, a vector in which values of pixels are arranged in the vertical direction is $g_k$, and a vector in which the projection images $g_k$ of a projection "k" are arranged only by the number of projections in the vertical direction is "g". An image f(x) in a reconstruction space is discretized, and a vector in which values of pixels are arranged in the vertical direction is "f". When those vectors are used, the equation (28) or (30) can be expressed as the following equation (31).

$$g_k = W_k f \tag{31}$$

where $W_k$ denotes a coefficient matrix expressing the projection computation (a matrix expressing the back projection computation of the projection "k" will be expressed as $W_k^T$)

When the attenuation correction and conversion to the absorption energy are added, the equation (31) can be expressed as the following equation (32) or (33).

$$g_k = W_k C_k B f = A_k f, \ A_k = W_k C_k B \tag{32}$$

$$g = Af, \ A = \begin{pmatrix} A_1 \\ \vdots \\ A_{N_p} \end{pmatrix} \tag{33}$$

where $C_k$ denotes a diagonal matrix having the coefficient $c_k(x)$ of the attenuation correction as a diagonal element, and B denotes a diagonal matrix having a value b(x) obtained by dividing absorption energy per scattering by density as a diagonal element.

The solution of the equation (32) can be expressed as the following equation (34) by the root-mean-square estimation method.

$$f^{est} = A^T (AA^T + \gamma^2 I)^{-1} g \tag{34}$$

$\gamma^2$ denotes an estimation parameter and it is known that a value obtained by dividing dispersion of projection data by dispersion of the solution is the optimum value. Japanese Patent Application Nos. 2006-284325 and 2007-269447 describe, for example, a filter coefficient calculating method for obtaining a filtered projection image as shown by the following equation (35) from a projection image.

$$x = (AA^T + \gamma^2 I)^{-1} g \tag{35}$$

When correction on assumption that $A_k = W_k C_k B$ is performed for application to the reconstructing process of the embodiment, a filtered projection image can be obtained by using the techniques of Japanese Patent Application Nos. 2006-284325 and 2007-269447. The point that the attenuation correction using $C_k$ and conversion to the absorption energy using B are executed in the process of calculating the filter coefficient by the equation (35) is an important point different from the conventional technique.

When the filtered projection image is obtained, a solution can be obtained by the following equation (36).

$$f^{est} = A^T x \tag{36}$$

When a vector for decomposing the filtered projection image to projections is $x_k$ in the process, the equation (36) can be expressed as the following equation (37).

$$f^{est} = B^T \sum_{k=1}^{N_p} C_k^T W_k^T x_k \tag{37}$$

where $W_k^T$ denotes back projection computation of the projection "k". The process steps using the equation (24) are as shown in FIG. 33. In the processes shown in FIG. 33, it is assumed that the processes (2) and (3) are performed in each of the projections "k". After the processes (2) and (3) are finished on all of the projections, the processes (4) and (5) are performed.

<Effects>

As described above, in the embodiment, the reconstructing process accompanying the attenuation correction is performed by obtaining a spatial distribution of the attenuation coefficients $c_k(x)$ in a region irradiated with therapeutic radiation using CT images acquired for a treatment plan, and executing division with $c_k(x)$ at the time of back-projection of each of the projection images using the spatial distribution. By the process, a measurement error in the therapeutic radiation caused by attenuation of scattering radiation in a subject itself can be reduced, and the spatial distribution of the scattering radiation source having high quantitative property can be measured at high precision.

Fourth Embodiment

FIG. 34 is a flowchart showing the flow of the attenuation correcting process and the reconstructing process in a fourth embodiment. As shown in the diagram, in the fourth embodiment, the attenuation correcting process is applied to projection data prior to execution of back projection.

At the time of performing a radiation treatment, the operator has to know an approximate position in a subject, on which a cone beam falls. Consequently, a method of positioning an apparatus for measuring a focal position of the therapeutic radiation and a radiation direction and a subject is always performed. In the fourth embodiment, using a result of the positioning, an approximate position of the center axis of the cone beam is obtained as shown in FIGS. 35A and 35B. Further, a plane (scattering radiation source plane) passing the obtained center axis and passing a straight line orthogonal to both the center axis of the cone beam and the projection axis (in the direction of the collimator) of the detector is obtained. In the embodiment, a coordinate value on the plane is expressed as $x_c$.

In the attenuation correcting method of the embodiment, the total attenuation amount between the scattering radiation source plane and the detector is obtained, and a measurement value of the detector is divided by the total attenuation amount. The total attenuation amount between the plane and the detector is obtained as the following equation (38).

$$C_k(p_k(x_c)) = \exp\left(-\int \mu(x_c + ln_k) dl\right) \quad (38)$$

The total attenuation amount $C_k$ is a value which varies projection by projection and also varies pixel by pixel. By dividing the measurement value $e_k$ of each pixel in the detector by the total attenuation amount, corrected projection data $e_k'$ as shown by the following equation (39) is obtained.

$$e_k'(p_k(x_c)) = \frac{e_k(p_k(x_c))}{C_k(p_k(x_c))} \quad (39)$$

A filter is applied to the obtained projection data $e_k'$ to thereby obtain projection data $g_k$. By using $g_k$, the back projection computation is executed according to the equation (40) to obtain a reconstruction image.

$$f(x) = \frac{1}{N} \sum_{k=1}^{N_P} g_k(p_k(x)) \quad (40)$$

Using the obtained reconstruction image, precision of the attenuation correction can be improved by a repeating process. Since a region having a large pixel value in the reconstruction image can be regarded as a region irradiated with a cone beam, the center axis of a region having pixel values each equal to or larger than a predetermined value is obtained, and a scattering radiation source plane is newly obtained from the center axis. The attenuation correction and reconstruction is re-executed with the corrected scattering radiation source plane to generate a reconstruction image. Although a configuration of repeating the process three or more times, it is sufficient to repeat the process twice.

Fifth Embodiment

In the third and fourth embodiments, an example of estimating the attenuation coefficient distribution of scattering radiation from a CT image captured by a normal X-ray CT apparatus such as a CT image for use in a treatment plan has been described. In contrast, in the fifth embodiment, as a method of obtaining a CT image used for estimating an attenuation coefficient, an example of generating a CT image using a therapeutic radiation source provided for the radiotherapeutic system 1 will be described.

FIG. 36 is a diagram for explaining the configuration and motion of a rotary image pickup system of the radiotherapeutic system 1 of the fifth embodiment. A characteristic point of the radiotherapeutic system 1 shown in FIG. 36 is that a second detector 309 (in addition to the detector 301) provided so as to face the irradiating unit 203 is further provided.

The normal irradiating unit 203 (therapeutic X-ray source) is provided with a diaphragm for narrowing a radiation aperture in accordance with an affected region. At the time of emitting therapeutic X-ray beam, the diaphragm is used. In the embodiment, in addition to the therapeutic radiation, X-ray irradiation of a dose smaller than that for a treatment is performed by using the irradiating unit 203 to capture a CT image used for estimating the attenuation coefficient. At the time of irradiation for capturing a CT image, the dose is reduced, the diaphragm is opened wide, and a region larger than that at the time of treatment is irradiated with an X-ray.

The second detector 309 is disposed in a position so as to face the irradiating unit 203 to capture an X-ray image having a large region (large view field) around an affected region of a subject. The irradiating unit 203 and the second detector 309 rotate around the subject by 360° while maintaining the opposed positional relation to capture X-ray images in a plurality of places during the rotation. By reconstructing a CT image by using the X-ray images, a CT image can be generated using the energy of the therapeutic X-ray. A space distribution of the attenuation coefficient can be estimated by a known method using the CT image obtained as described above (since the energy of therapeutic X-ray and that of scattering radiation are largely different from each other, the above-described attenuation coefficient conversion has to be performed).

Sixth Embodiment

FIG. 37 is a diagram for explaining the configuration of the radiotherapeutic system 1 and motion of a rotary image pickup system as a sixth embodiment. As shown in the diagram, the radiotherapeutic system 1 as the sixth embodiment has a second irradiating unit (X-ray source) 209 in a position opposite to the detector 301 for detecting scattering radiation. The radiotherapeutic system 1 further includes a rotating mechanism for synchronously rotating the second irradiating unit 209 and the detector 301 while maintaining a predetermined phase interval so that the rotational trajectory plane of the second irradiating unit 209 and that of the detector 301 are parallel with each other.

Specifically, the second irradiating unit 209 is disposed in a position opposite to the detector 301. While making the detector 301 and the second irradiating unit 209 face each other, they are synchronously rotated, for example, around the center axis of a radiation beam as a center, and X-ray images are captured in a plurality of places during the rotation. The collimator of the detector 301 is formed so as to be directed to the focal point of the second irradiating unit 209. Further, the tube voltage of the second irradiating unit 209 is set so that the energy distribution of an X-ray generated by the X-ray tube of the second irradiating unit 209 becomes close to the energy distribution of scattering radiation. A representative tube voltage lies in the range of 300 kV to 1000 kV. When tomography is performed using the obtained X-ray images, an attenuation coefficient distribution can be obtained. In the method, the energy distribution of the X-ray tube and that of the scattering radiation are almost equal to each other. It is therefore unnecessary to convert the attenuation coefficient, and an accurate attenuation coefficient can be obtained more promptly and easily than the radiotherapeutic systems of the first and third embodiments.

Seventh Embodiment

As shown in FIG. 38, the radiotherapeutic system 1 as a seventh embodiment has the second irradiating unit 209 in a position opposite to the detector 301 for detecting scattering radiation in a manner similar to the sixth embodiment. While maintaining the positional relation between the detector 301 and the second irradiating unit 209 (while making them face each other), they are rotated, for example, around the body axis of a subject as a center, and X-ray images are captured in a plurality of places during the rotation. Using the captured data, a CT image is reconstructed. The tube voltage of the second irradiating unit 209 is set so that the energy distribution of an X-ray generated by the second irradiating unit 209 becomes close to the energy distribution of scattering radiation. In the method, the energy distribution of the X-ray tube and that of the scattering radiation are almost equal to each other like the sixth embodiment. It is therefore unnecessary to convert the attenuation coefficient, and an accurate attenuation coefficient can be obtained more promptly and easily than the radiotherapeutic systems of the first and third embodiments.

Eighth Embodiment

In the radiotherapeutic system 1 as an eighth embodiment, the attenuation correcting process of any of the first to fifth embodiments is applied to the method of performing three-dimensional reconstruction on a scattering radiation source distribution by using flat radiation (that is, the method shown in FIGS. 22 and 23).

FIG. 39 is a diagram for explaining the attenuation correcting method in the case of performing irradiation at the irradiation angle "b". An alternate long and short dash line expresses the center plane of the flat radiation at the irradiation angle "b". The position of the center plane is calculated from a measurement value of an encoder or the like of the irradiating unit 203. The total attenuation amount between the center plane and the detector is calculated as the following equation (41).

$$C_k(p_k(x_c)) = \exp\left(-\int \mu(x_c + l n_k) dl\right) \quad (41)$$

where "k" denotes a number for distinguishing irradiation angles "a", "b", "c", and "d". $\mu(x)$ denotes an attenuation coefficient in the position "x" and is, for example, a value obtained by the attenuation coefficient estimating process of the first embodiment. $X_c$ denotes a coordinate value on the center plane, $n_k$ denotes an incidence direction of scattering radiation to the detector, and $p_k(x)$ denotes a position on the detector plane when x is projected onto the detection face in the direction of $n_k$. The total attenuation amount $C_k$ is a value which varies according to the irradiation angle and also varies pixel by pixel. By dividing the measurement value $e_k$ of each pixel in the detector by the total attenuation amount, corrected projection data $e_k'$ as shown by the following equation (42) is obtained.

$$e_k'(p_k(x_c)) = \frac{e_k(p_k(x_c))}{C_k(p_k(x_c))} \quad (42)$$

Also with the above-described configuration, similar effects can be obtained.

Ninth Embodiment

A ninth embodiment of the present invention will now be described. A radiotherapeutic system as the ninth embodiment executes a reconstructing process in which conditions on a region irradiated with scattering radiation are introduced.

FIG. 40 is a block configuration diagram of the radiotherapeutic system 1 of the ninth embodiment, which is different from FIG. 2 with respect to the configuration of the data processing system 5.

The data processing system 5 has a correction processor 501, a scattering radiation source existing region determining unit 502, a reconstruction processor 503, a conversion processor 505, and an data processor 507.

The correction processor 501 performs a data calibration process, a correcting process for eliminating noise, and the like as necessary. The correcting process executed by the correction processor 501 will be described in detail later.

The scattering radiation source existing region determining unit 502 determines a region corresponding to a scattering radiation source locally existing in a subject by back projection process using measurement results in different positions of the scattering radiation detector. The process of determining a scattering radiation source existing region will be described in detail later.

The reconstruction processor 503 executes an image reconstructing process using scattering radiation image data detected by the scattering radiation detection system 3 and position information indicative of a position in which the scattering radiation image data is detected to obtain scattering radiation volume data indicative of a three-dimensional distribution of density of the number of scattering events (the number of scattering occurrence times). As the reconstructing method, for example, when the direction of the collimator is orthogonal to the scan axis, a CT reconstructing method is used. On the other hand, when the direction of the collimator is not orthogonal to the scan axis, a tomography reconstructing method is used. Particularly, the reconstruction processor 503 executes the reconstructing process of repeating the back projection and the projection while correcting the solution until the projection image matches the measurement image using only a scattering radiation source existing region as a target by assuming that there is no scattering radiation source distributed on the outside of the irradiation region. The repetitive reconstructing process will be described in detail later.

The conversion processor 505 converts three-dimensional image data obtained by the image reconstructing process to absorbed dose volume data indicative of a three-dimensional distribution of absorbed radiation dose (absorbed dose).

<Conditional Repetitive Reconstructing Function>

A conditional repetitive reconstructing function of the radiotherapeutic system 1 will now be described. Different from general X-ray tomography and an X-ray CT scan, in the case of imaging an X-ray irradiated region (scattering radiation source distribution) of the radiotherapeutic system, it is known that a region irradiated with radiation is localized. In the conditional repetitive reconstructing function, first, as shown in FIG. 41A, a scattering radiation existing region is determined by the back projection process using measurement results in different positions of the scattering radiation detector. Next, as shown in FIG. 41B, in the reconstructing process, the reconstructing process of repeating the back projection and the projection while correcting the solution until the projection image matches the measurement image using only a scattering radiation source existing region as a target by assuming that there is no scattering radiation source distributed on the outside of the irradiation region is executed. By the process, a spatial distribution of the scattering radiation source (or a spatial distribution of absorbed dose) in a region irradiated with radiation which locally exists in the subject is suitably visualized. The conditional repetitive reconstructing function is executed, for example, in step S4a in FIG. 20 and step S4b in FIG. 21.

FIG. 42 is a flowchart showing the flow of process according to the conditional repetitive reconstructing function (conditional repetitive reconstructing process). As shown in the diagram, the conditional repetitive reconstructing process has largely two steps. The processes in the steps will be described below.

[Process of Determining Scattering Radiation Source Existable Region in Step S41]

FIG. 43 is a flowchart showing the flow of a process of determining a scattering radiation source existable region.

First, the scattering radiation source existing region determining unit 502 divides scattering radiation images of Np projections to, for example, regions whose measurement value is close to zero and the other regions as shown in FIG. 44A (step S411). It is sufficient to use a threshold method for the region division. To determine a threshold, for example, "peak value of histogram+constant" or the like can be used. After performing binarization using the threshold, a process of eliminating isolated small foreground regions is executed to eliminate the influence of noise. At this time point, a binarized projection image is obtained in each projection. In the binarized projection image, the value is 0 in a region where the scattering radiation image is close to zero, and the value is 1 in the other regions.

Next, the scattering radiation source existing region determining unit 502 performs back projection on the binarized projection image as shown in FIG. 44B (step S412). The scattering radiation source existing region determining unit 502 determines, as a scattering radiation source existable region, a region whose value is equal to the number of projections in an image obtained as a result of the back projection (step S413). In the embodiment, as shown in FIG. 44C, the region whose value is 4 is determined as a scattering radiation source existable region S.

[Repetitive Reconstructing Process in Step S42]

FIG. 45 is a flowchart showing the flow of a process of determining the scattering radiation source existable region.

First, the reconstruction processor 503 sets a temporal solution image (step S421). In the embodiment, as the initial value of the temporal solution image, a solution obtained in step S41 is used.

Next, the reconstruction processor 503 replaces a region other than the scattering radiation source existable region in the temporal solution image with zero (step S422), generates a projection image by projection process, obtains the difference from a projection image as a measurement value (step S423), and reconstructs the image using the difference as a projection image (step S424 and S425).

The reconstruction processor 503 subtracts the differential reconstruction image from the first temporal solution image (image obtained by replacement with 0) (step S426) and determines whether the number of repeating times of the reconstruction process has reached a predetermined number of times or not. When it is determined that the number of repeating times has not reached the predetermined number of times, the reconstruction processor 503 uses the latest projection image obtained in step S425 as a temporal solution image and repeats the processes in the steps S422 to S426, thereby repetitively correcting the temporal solution image and making the image converged to a final result. On the other hand, when it is determined that the number of repeating times has reached the predetermined number of times, the reconstruction processor 503 finishes the repetitive reconstruction process.

<Effects>

According to the above-described configuration, following effect can be realized.

In the radiotherapeutic system, by the back projection process using measurement results in different positions in the scattering radiation detector, a scattering radiation source existing region in a subject is determined, a temporal solution on the outside of the scattering radiation source existable region is replaced with 0, and reconstruction of the first time is executed. By the process, most of a projection image of an error is reconstructed to a scattering radiation source existable region by the repetitive reconstruction of the first time, and the value of the temporal solution image in the scattering radiation source existable region largely decreases.

In the next reconstructing process, the temporal solution image obtained by the reconstructing process of last time is used as an input image, the temporal solution on the outside of the scattering radiation source existable region is replaced with 0, and the reconstructing process is executed again. The processes are repeated. By such a repetitive reconstructing process, a signal corresponding to the scattering radiation source existable region can be visualized faithfully, and a signal which does not correspond to the scattering radiation source existable region can be eliminated. Artifact peculiar to the tomography scan can be reduced and the image quality can be improved.

The conditional repetitive reconstructing process produces a large effect since the reconstruction error is reduced even by repeating the process at least twice. By increasing the number of repeating times, it is more effective. However, at most ten times is sufficient.

Tenth Embodiment

In the ninth embodiment, by introducing the condition that the distribution of the scattering radiation source is zero to a region where a scattering radiation source is not supposed to exist, the precision of a solution is improved. In contrast, in a tenth embodiment, a method of further generalizing the condition that the distribution of the scattering radiation source is zero will be described. Introduction of the condition that the distribution of the scattering radiation source is zero to regions where a scattering radiation source is not supposed to exist produces two effects.

In the conventional reconstructing method, a solution larger than 0 may be obtained in a region where the scattering radiation source is supposed to be zero. Since the region is a region in which the scattering radiation source is supposed to be zero, by adding the condition that the scattering radiation source=0 to the region, the precision of the solution can be improved.

In the conventional reconstructing method, a solution of a negative value may be obtained in a region where the scattering radiation source has a small value. Particularly, a solution of a negative value tends to be obtained in a region in which the scattering radiation source is supposed to be zero. Since the value of the scattering radiation source does not become a negative value in principle, by adding the condition that the scattering radiation source=0 to the region, the precision of the solution can be improved.

In the embodiment, the above-described two replacement cases are generalized as follows, and the repetitive reconstructing process according to the condition with respect to the upper and lower limits of the solution is performed.

An image in which a solution is projected does not exceed a projection image which is input in the reconstructing process (reconstruction input projection image).

The solution does not become a negative value (nonnegative condition).

In consideration of the conditions, a policy of selecting a solution such that "an image in which a solution is projected is close to a reconstruction input projection image as much as possible" is employed. In the first embodiment, a condition can be added only to a region where a scattering radiation source is supposed to be zero. In the second embodiment, by determining the upper and lower limits for the solution in the above-described two conditions, the condition can be given to all of the regions.

Concrete processes executed by the reconstruction processor 503 are as follows.

[Basic Method]

A projection process of an image "f" in the reconstruction space is expressed as "Af". A result of the process is a vector in a projection space. A back projection process on a projection image "g" is expressed as $A^T g$. A result of the process is a vector in a reconstruction space.

First, a conventional method as the base of the basic method will be described. The case of obtaining "f" satisfying the following equation (43) will be considered.

$$A^T g = (A^T A + P) f \quad (43)$$

where Pf denotes a penalty vector of the solution "f". For undesirable "f", $f^T Pf$ has a large value. The relation $f^T Pf \geq 0$ is always satisfied. By the equation (43), the following equation (44) is derived.

$$0 = A^T Af - A^T g + Pf \quad (44)$$

A function q(f) making the right side of the equation (44) a derived function is defined by the following equation (45).

$$q(f) = \frac{1}{2}|Af|^2 + \frac{1}{2}f^T Pf - f^T A^T g \quad (45)$$

To solve the equation (43), it is sufficient to minimize the equation (45) as an object function. To minimize the equation (45), minimization methods such as the conjugate gradient method can be used. In many minimization methods including the conjugate gradient method, calculation of an assessment function "q" and its derived function is necessary. As described above, Af and $A^T g$ as processing elements denote the projection process and the back projection process, respectively, so that it is necessary to execute the projection process and the back projection process. For reference, the derived function of q(f) is expressed by the following equation (46).

$$\nabla q(f) = A^T(Af - g) + Pf \quad (46)$$

For correction in a direction "h" (concretely, λh is added to the solution "f"), it is necessary to determine a distance in the direction "h" for minimization. Concretely, λ that minimizes q(f+λh) is determined. It can be obtained by solving the following equation (47).

$$h^T \nabla q(f + \lambda h) = h^T \left( A^T (A(f + \lambda h) - g) + P(f + \lambda h) \right) = 0 \quad (47)$$

Calculation to solve the equation (48) is shown below.

$$h^T A^T Af + h^T A^T A\lambda h - h^T A^T g + h^T Pf + \lambda h^T Ph = 0 \quad (48)$$

$$\lambda h^T A^T Ah - \lambda h^T Ph = h^T A^T g - h^T A^T Af - h^T Pf$$

$$\lambda = \frac{h^T A^T g - h^T A^T Af - h^T Pf}{h^T A^T Ah - h^T Ph}$$

$$\lambda = \frac{(Ah)^T (g - Af) - h^T Pf}{|Ah|^2 - h^T Ph}$$

$$q(f) = \alpha_g \text{Positive}\left(\frac{1}{2} f^T A^T (Af - g)\right) +$$

$$\alpha_s \text{Negative}\left(\frac{1}{2} f^T A^T (Af - g)\right) + \frac{1}{2} f^T (Pf - A^T g)$$

$$= \frac{1}{2} f^T A^T (\alpha_g \text{Positive}(Af - g) +$$

$$\alpha_s \text{Negative}(Af - g)) + \frac{1}{2} f^T (Pf - A^T g)$$

The procedure of the conventional method that concretely executes the above processes is shown in FIG. 46. An example of the steepest descent method is shown as an example for description. In practice, a more excellent method such as the conjugate gradient method has to be used.

[Introduction of Nonnegative Condition]

In the embodiment, to introduce a condition that the solution does not become a negative value, the procedure shown in FIG. 46 is changed to the procedure shown in FIG. 47 (step 9b is newly added).

[Introduction of Condition that Image on Which Solution is Projected does not Exceed Reconstruction Input Projection Image]

In place of the equation (45), an object function shown by the following equation (48) is used.

$$h^T A^T Af + h^T A^T A\lambda h - h^T A^T g + h^T Pf + \lambda h^T Ph = 0 \quad (48)$$

$$\lambda h^T A^T Ah - \lambda h^T Ph = h^T A^T g - h^T A^T Af - h^T Pf$$

$$\lambda = \frac{h^T A^T g - h^T A^T Af - h^T Pf}{h^T A^T Ah - h^T Ph}$$

$$\lambda = \frac{(Ah)^T (g - Af) - h^T Pf}{|Ah|^2 - h^T Ph}$$

$$q(f) = \alpha_g \text{Positive}\left(\frac{1}{2} f^T A^T (Af - g)\right) +$$

$$\alpha_s \text{Negative}\left(\frac{1}{2} f^T A^T (Af - g)\right) + \frac{1}{2} f^T (Pf - A^T g)$$

$$= \frac{1}{2} f^T A^T (\alpha_g \text{Positive}(Af - g) +$$

$$\alpha_s \text{Negative}(Af - g)) + \frac{1}{2} f^T (Pf - A^T g)$$

where Positive(v) denotes a function that when the value of the element $v_i$ is a positive value, the value of the i-th element becomes $v_i$ and, when the value of the element $v_i$ is 0 or less, the value of the i-th element becomes 0. On the contrary, Negative(v) denotes a function that when the value of the element $v_i$ is 0 or less, the value of the i-th element becomes $v_i$ and, when the value of the element $v_i$ is a positive value, the value of the i-th element becomes 0. The equation (48) is equivalent to the equation (45) when $\alpha_g = \alpha_s = 1$. Typically, a value satisfying $\alpha_g > \alpha_s$ is used.

As a derived function of the equation (48), the following equation (49) is used.

$$\nabla q(f) = \alpha_g \text{Positive}(A^T(Af - g)) + \quad (49)$$

$$\alpha_s \text{Negative}(A^T(Af - g)) + Pf$$

$$= A^T(\alpha_g \text{Positive}(Af - g) +$$

$$\alpha_s \text{Negative}(Af - g)) + Pf$$

Af−g in the equation (48) denotes the difference between projection of the temporal solution and the input projection image. When the value satisfying $\alpha_g > \alpha_s$ is used, in the case where the projection of the temporal solution exceeds the input projection image, a larger coefficient is applied, the object function (48) becomes a larger value.

FIG. 48 shows an example where $\alpha_g=2$ and $\alpha_s=1$. Since a solution of decreasing the object function is selected in the optimizing process, as a result, a solution by which projection of the temporal solution does not largely exceed the input projection image is selected.

The procedure is as shown in FIG. 49. The characteristic point of the procedure is that, in calculation of the derived function in step 6b, a process of comparing projection of a temporal solution "hi" and an input projection image with each other and, according to the sign of each of the elements of Af−g, multiplying each of the elements of Af−g with a coefficient in which a positive value is larger is added. As step 6b changes, λ calculated in step 8 becomes indefinite. Consequently, it is desirable to add step 8b to correct λ to a more accurate value.

<Effect>

In the conditional repetitive reconstructing process of the embodiment, the condition regarding the lower limit that the solution is a nonnegative and the condition regarding the upper limit that the image on which the solution is projected does not exceed the reconstruction input projection image can be introduced, so that the solution can be regulated. For example, a condition is added such that the scattering radiation source distribution has a value close to 0 in a position in a subject corresponding to a region in which a scattering radiation image shows a value close to 0. Therefore, the tenth embodiment has an effect similar to that of the ninth embodiment. Further, a condition is added such that, also in a region where a scattering radiation image shows a predetermined value which is not 0, a value of projecting the scattering radiation source distribution is smaller than the value. In the tenth embodiment, a restriction severer than that in the ninth embodiment is given to the reconstruction. Therefore, the tenth embodiment produces an effect that the precision of reconstruction can be improved more than that in the ninth embodiment.

Eleventh Embodiment

In the tenth embodiment, a nonnegative condition can be given to a whole solution. However, in such a method, there is the case that the nonnegative condition does not function effectively. For example, in the case where only a part of scattering radiation sources has a large value as shown in FIG. 50A, an erroneous solution having a negative value tends to be derived around the part as shown in FIG. 50B. In this case, the solution can be improved by the nonnegative condition. However, in the case where an uniform scattering radiation source distribution is added to FIG. 50A as shown in FIG. 50C, in a reconstruction method similar to that of FIG. 50B, a solution does not become a negative value as shown in FIG. 50D. That is, even if the same error as that in FIG. 50B is included in the solution, since the uniform component is added, the solution does not become a negative value and the error cannot be corrected.

In the eleventh embodiment, a solution (distribution of scattering radiation sources) is expressed by synthesis of a plurality of distributions modeled. That is, an originally one solution is decomposed to a plurality of modeled solutions. After that, the condition of the second embodiment is given to each of the decomposed solutions. For example, even in the case where a uniform scattering distribution exists as shown in FIG. 50C, suitable image reconstruction is realized.

Synthesis of the solutions can be expressed by the following equation (50).

$$f = \sum_{j=1}^{M} m_j f^j = (f^1 \ldots f^M) m = Fm \quad (50)$$

In the equation (50), the solution is expressed by synthesis of M functions. A synthesis equation approximated only first R functions can be calculated by the following equation (51).

$$f = \sum_{j=1}^{R} m_j f^j = (f^1 \ldots f^R) m_R = F_R m_R \quad (51)$$

A distribution corresponding to small "j" in the decomposed solution distribution $f^j$ is set a wide area distribution, and $f^j$ is determined so that the distribution becomes a local distribution as j increases. Particularly, $f^0$ denotes an uniform distribution. It is sufficient to set so that all of the elements of $f^j$ have a value of 0 or larger.

The object function is expressed by the following equation (52) by substituting the equation (50) to the equation (48).

$$q(f) == \quad (52)$$
$$\frac{1}{2} m_R^T F_R^T A^T (\alpha_g \text{Positive}(AF_R m_R - g) + \alpha_s \text{Negative}(AF_R m_R - g)) +$$
$$\frac{1}{2} m_R^T F_R^T (P F_R m_R - A^T g)$$

As a derived function, the following equation (53) is used.

$$\nabla q(f) = F_R^T A^T (\alpha_g \text{Positive}(AF_R m_R - g) + \alpha_s \text{Negative}(AF_R m_R - g)) + F_R^T P F_R m_R \quad (53)$$

Since the value of $F_R m_R$ is synthesis of R solution distributions $f^j$, the calculating process for the object function and the derived function varies according to the value of R. When R is determined, mR is obtained by the method of the tenth embodiment. By calculating $F_R m_R$, a solution distribution can be obtained. In this case, A in the tenth embodiment has to be replaced with $AF_R$ of the eleventh embodiment.

In the eleventh embodiment, while gradually increasing R starting from 1, the reconstructing process is repetitively executed as shown in FIG. 52. As a projection image "g", the value of the reconstruction input image is set initially. Each time the process is repeated, a projection $Af_k$ of a solution $f_k$ is subtracted. In the step k in repetition, reconstruction is performed from a projection image subtracted in all of the preceding steps. $F^j$ has a wider distribution for small j. As the number of repetition increases, R increases. As the number of steps increases, a finer structure is reconstructed. As an example, a uniform distribution is estimated first. After that, a local distribution is estimated. In the second and subsequent steps, a projection image for the uniform distribution is eliminated from the projection image. Consequently, also at the time of estimating a local distribution in each of the subsequent steps as described first with the conceptual diagram, the nonnegative condition effectively works.

In the reconstructing process of the embodiment described above, in the example of FIG. 51A (the same as that of FIG. 50C), a solution is decomposed to an uniform component shown in FIG. 51B and a local component shown in FIG. 51C, a nonnegative condition is given to each of the components, and the image is reconstructed. Since the nonnegative condition is given, an error included in the solution is reduced as shown in FIGS. 51E and 51F. A solution finally obtained is a synthetic solution. Obviously, an error included in a final solution is reduced as shown in FIG. 51D.

The present invention is not directly limited to the foregoing embodiments. At the time of carrying out the invention, the components can be modified and embodied without departing from the gist. An example of a concrete modification is as follows.

For example, the functions in the embodiment can be also realized by installing a program for executing the process in a computer such as a work station and developing the program on a memory. The program which can make a computer execute the method can be stored in a recording medium such as a magnetic disk (floppy (registered trademark) disk, hard disk, or the like), optical disks (CD-ROM, DVD, or the like), a semiconductor memory, or the like and distributed.

By a proper combination of a plurality of components disclosed in the foregoing embodiments, various inventions can be generated. For example, some components may be eliminated from all of the components shown in the embodiments. Further, the components in different embodiments may be properly combined.

What is claimed is:

1. A radiotherapeutic system comprising:
a first irradiation unit which irradiates a subject with a radiotherapeutic beam;
a detection unit which detects scattering radiation from the subject, which occurs on the basis of the radiotherapeutic beam, in a plurality of positions and generates scattering radiation data;
a collimator which is arranged on the detection unit and causes the detection unit to detect the scattering radiation at a predetermined scattering angle θ in a range of $140° \leq θ < 180°$; and
an image reconstruction unit which reconstructs a radiation dose image indicative of a distribution of radiation dose in the subject on the basis of the detected scattering radiation data in the plurality of positions.

2. The radiotherapeutic system according to claim 1, wherein the detection unit includes a rotation unit which rotates a detection face of the detection unit around an axis of the radiotherapeutic beam as a center so as to keep an angle of the detection face to the axis of the radiotherapeutic beam.

3. The radiotherapeutic system according to claim 1, wherein the detection unit has a plurality of detectors disposed in the plurality of positions on a circumference using an axis of the radiotherapeutic beam as a center.

4. The radiotherapeutic system according to claim 1, wherein the reconstruction unit reconstructs radiation volume data by executing image reconstruction with respect to digital tomosynthesis technology using the scattering radiation data detected in the plurality of positions.

5. A radiotherapeutic system comprising:
a first irradiation unit which irradiates a subject with a radiotherapeutic beam;
a detection unit which detects scattering radiation from the subject, which occurs on the basis of the radiotherapeutic beam, in a plurality of positions and generates scattering radiation data;
a collimator which is arranged on the detection unit and causes the detection unit to detect the scattering radiation at a predetermined scattering angle θ; and
an image reconstruction unit which reconstructs a radiation dose image indicative of a distribution of radiation dose in the subject on the basis of the detected scattering radiation data in the plurality of positions,
wherein the image reconstruction unit reconstructs scattering radiation source image data showing a three dimensional distribution of the scattering radiation by using the scattering radiation data; and further comprises,
an image generation unit which converts the scattering radiation source image data to image data on absorption of radiation showing a three dimensional distribution of absorbed radiation dose; and
a display unit which displays the radiation dose image on the basis of the image data on absorption of radiation.

6. The radiotherapeutic system according to claim 5, wherein the image generation unit calculates density of voxels of an absorbed dose volume by averaging a density of at least one voxel in a corresponding form image.

7. The radiotherapeutic system according to claim 6, wherein the image generation unit calculates the density of the voxels on the basis of the corresponding form image obtained by capturing an image of the subject.

8. A radiotherapeutic system comprising:
a first irradiation unit which irradiates a subject with a radiotherapeutic beam;
a detection unit which detects scattering radiation from the subject, which occurs on the basis of the radiotherapeutic beam, in a plurality of positions and generates scattering radiation data:,
a collimator which is arranged on the detection unit and causes the detection unit to detect the scattering radiation at a predetermined scattering angle θ; and
an image reconstruction unit which reconstructs a radiation dose image indicative of a distribution of radiation dose in the subject on the basis of the detected scattering radiation data in the plurality of positions,
wherein the image reconstruction unit generates an absorbed dose volume subjected to attenuation correction on the basis of a spatial distribution of attenuation coefficients of radiation rays in an irradiated region in the subject irradiated with the radiotherapeutic beam and the scattering radiation data.

9. The radiotherapeutic system according to claim 8, wherein the image reconstruction unit executes the attenuation correction by calculating a total number of the attenuation coefficients corresponding to a region between a scattering radiation source plane defined by a center axis of the radiotherapeutic beam and perspective axis of the scattering radiation data and the detection unit and dividing the scattering radiation data by the total number of the attenuation coefficients.

10. The radiotherapeutic system according to claim 8, wherein the attenuation correction is executed by calculating a total number of the attenuation coefficients corresponding to a region between each of positions of the irradiated region and a detection position of the detection unit and dividing or multiplying backprojection data on the basis of the total number of the attenuation coefficients in each of the positions of the irradiated region.

11. The radiotherapeutic system according to claim 8, wherein the spatial distribution of the attenuation coefficients of the radiation rays is generated by using CT image data acquired by an X-ray CT apparatus.

12. The radiotherapeutic system according to claim 8, further comprising,
 a second irradiation unit which irradiates having an energy approximating to an energy of the scattering radiation from the subject; and
 a rotating mechanism which synchronously rotates the second irradiation unit and the detection unit while maintaining a projection axis of the second irradiation unit and the detection unit so that a rotational trajectory plane of the second irradiation unit and a rotational trajectory plane of the detection unit become parallel with or equivalent to each other,
 wherein the spatial distribution of the attenuation coefficients of the radiation rays is generated by making the second irradiation unit emit radiation having the energy close to the scattering radiation from the subject while the second irradiation unit is rotated by the rotating mechanism and using image data obtained in the plurality of positions by the detection unit.

13. The radiotherapeutic system according to claim 8, further comprising a calculation unit for calculating the spatial distribution of the attenuation coefficients of the radiation rays.

14. A radiotherapeutic system comprising:
 a first irradiation unit which irradiates a subject with a radiotherapeutic beam:,
 a detection unit which detects scattering radiation from the subject, which occurs on the basis of the radiotherapeutic beam, in a plurality of positions and generates scattering radiation data;
 a collimator which is arranged on the detection unit and causes the detection unit to detect the scattering radiation at a predetermined scattering angle θ; and
 an image reconstruction unit which reconstructs a radiation dose image indicative of a distribution of radiation dose in the subject on the basis of the detected scattering radiation data in the plurality of positions,
 wherein the image reconstruction unit generates a reconstruction image by receiving the scattering radiation data in which a scattering radiation source existing region is determined by a predetermined method and repeatedly executing a reconstruction process according to a predetermined condition and, using the reconstruction image, generating the radiation dose image indicative of the distribution of the radiation dose in the subject.

15. The radiotherapeutic system according to claim 14, wherein the image reconstruction unit repeatedly executes the reconstruction process in accordance with a condition that the reconstruction image generated in each of the reconstruction processes does not exceed the scattering radiation data which is entered in the reconstructing processes.

16. The radiotherapeutic system according to claim 14, wherein the image reconstruction unit repeatedly executes the reconstruction process in accordance with a condition that a value of the scattering radiation data which is entered is set to 0 in a region in which the scattering radiation has a negative value.

17. The radiotherapeutic system according to claim 14 wherein the image reconstruction unit repeatedly executes the reconstruction process in accordance with a condition that the scattering radiation data which is entered is set to 0 in a region which does not correspond to the scattering radiation source existing region.

18. A radiotherapeutic dose distribution measuring method comprising:
 irradiating a subject with a radiotherapeutic beam;
 detecting scattering radiation at a scattering angle θ in a range of $140° \leq θ < 180°$ from the subject, which occurs on the basis of the radiotherapeutic beam, in a plurality of positions and generates scattering radiation data; and
 reconstructing a radiation dose image indicative of a distribution of radiation dose in the subject on the basis of the detected scattering radiation data in the plurality of positions.

\* \* \* \* \*